(12) United States Patent
Hittinger et al.

(10) Patent No.: US 11,725,213 B2
(45) Date of Patent: Aug. 15, 2023

(54) POLYPEPTIDE AND YEAST CELL COMPOSITIONS AND METHODS OF USING THE SAME

(71) Applicant: Wisconsin Alumni Research Foundation, Madison, WI (US)

(72) Inventors: Chris Todd Hittinger, Madison, WI (US); EmilyClare Patricia Baker, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 10 days.

(21) Appl. No.: 17/341,224

(22) Filed: Jun. 7, 2021

(65) Prior Publication Data

US 2021/0340553 A1  Nov. 4, 2021

Related U.S. Application Data

(62) Division of application No. 16/378,106, filed on Apr. 8, 2019, now Pat. No. 11,028,402.

(60) Provisional application No. 62/654,021, filed on Apr. 6, 2018.

(51) Int. Cl.
| | |
|---|---|
| C12N 1/14 | (2006.01) |
| C12N 15/00 | (2006.01) |
| C12P 7/00 | (2006.01) |
| C12N 15/81 | (2006.01) |
| C12N 1/16 | (2006.01) |
| C07K 14/395 | (2006.01) |

(52) U.S. Cl.
CPC .............. *C12N 15/81* (2013.01); *C12N 1/16* (2013.01); *C12P 7/00* (2013.01); *C07K 14/395* (2013.01)

(58) Field of Classification Search
CPC .............. C12N 15/81; C12N 1/16; C12P 7/00
See application file for complete search history.

(56) References Cited

U.S. PATENT DOCUMENTS

| | | |
|---|---|---|
| 8,053,224 B2 | 11/2011 | Hatanaka et al. |
| 2016/0046952 A1 | 2/2016 | Hittinger |
| 2016/0340698 A1 | 11/2016 | Jung et al. |
| 2018/0127784 A1 | 5/2018 | Alexander |
| 2018/0155732 A1 | 6/2018 | Hittinger |

OTHER PUBLICATIONS

A0A0L8RLD5_SACEU. UnitProtKB Database. Feb. 15, 2017.
Alves SL, et al. Molecular analysis of maltotriose active transport and fermentation by *Saccharomyces cerevisiae* reveals a determinant role for the AGT1 permease. Appl Environ Microbiol. 2008;74(5):1494-501. pmid:18203856.
Barnett J. A., 1992 Some controls on oligosaccharide utilization by yeasts: The physiological basis of the Kluyver effect. FEMS Microbiol. Lett. 100: 371-378.
Barrett M. P., et al., 1999 Structure and function of facultative sugar transporters. Curr. Opin. Cell Biol. 11: 496-502.
Bilinski CA, et al. Developments in sporulation and breeding of brewer's yeast. Yeast. 1989;5(6):429-38.
Blount Z. D., et al., 2012 Genomic analysis of a key innovation in an experimental *Escherichia coli* population. Nature 489: 513-518.
Brickwedde A, et al. Evolutionary Engineering in Chemostat Cultures for Improved Maltotriose Fermentation Kinetics in *Saccharomyces pastorianus* Lager Brewing Yeast. Front Microbiol. 2017;8:1690. pmid:28943864.
Brickwedde A, et al. Structural, Physiological and Regulatory Analysis of Maltose Transporter Genes in *Saccharomyces eubayanus* CBS 12357T. Front Microbiol. 2018;9: 1786. pmid:30147677.
Briggs DE, et al. Metabolism of wort by yeast. Brewing: science and practice. Chapter 12. Abington Hall, Abington Cambridge CB1 6AH, England: Woodhead Publishing Limited; 2004.
Brouwers N, et al. In vivo recombination of *Saccharomyces eubayanus* maltose-transporter genes yields a chimeric transporter that enables maltotriose fermentation. bioRxiv. 2018; 428839.
Charron MJ, et al. The naturally occurring alleles of MAL1 in *Saccharomyces* species evolved by various mutagenic processes including chromosomal rearrangement. Genetics. 1988;120(1):83-93. pmid:2851483.
Cheng Q, et al. The maltose permease encoded by the MAL61 gene of *Saccharomyces cerevisiae* exhibits both sequence and structural homology to other sugar transporters. Genetics. 1989;123(3):477-84. pmid:2689282.
Cousseau F. E. M., et al., 2013 Characterization of maltotriose transporters from the *Saccharomyces eubayanus* subgenome of the hybrid *Saccharomyces pastorianus* lager brewing yeast strain Weihenstephan 34/70. Lett. Appl. Microbiol. 56: 21-29.
Day RE, et al. Characterization of the putative maltose transporters encoded by YDL247w and YJR160c. Yeast. 2002;19(12):1015-27. pmid:12210897.
Day RE, et al. Molecular analysis of maltotriose transport and utilization by *Saccharomyces cerevisiae*. Appl Environ Microbiol. 2002;68(11):5326-35. pmid:12406721.
Dietvorst J, et al. Maltotriose utilization in lager yeast strains: MTT1 encodes a maltotriose transporter. Yeast. 2005;22(10):775-88. pmid:16088872.

(Continued)

*Primary Examiner* — Yong D Pak

(74) *Attorney, Agent, or Firm* — Quarles & Brady, LLP

(57) ABSTRACT

Polypeptides comprising maltose/maltotriose transporters are provided. Additionally, polynucleotides, DNA constructs, and vectors encoding a maltose/maltotriose transporter, or yeast cells harboring such polynucleotides are provided. The yeast cell may be a *Saccharomyces eubayanus* cell modified to increase the expression or transport activity of a maltose/maltotriose transporter at the plasma membrane of the cell. Further, methods are provided for making a fermentation product by culturing any one of the yeast cells described herein with a fermentable substrate. Finally, methods are provided to select for and isolate maltotriose-utilizing strains of *Saccharomyces eubayanus*.

17 Claims, 9 Drawing Sheets

Specification includes a Sequence Listing.

(56) References Cited

OTHER PUBLICATIONS

Gibson B. R., et al., 2013 Comparative physiology and fermentation performance of Saaz and Frohberg lager yeast strains and the parental species *Saccharomyces eubayanus*. Yeast 30: 255-266.

Han E, et al. Characterization of AGT1 encoding a general a-glucoside transporter from *Saccharomyces*. Mol Microbiol. 1995;17(6):1093-107. pmid:8594329.

Horák J. Regulations of sugar transporters: insights from yeast. Curr Genet. 2013;59(1-2):1-31. pmid:23455612.

Jansen MLA, et al. Prolonged maltose-limited cultivation of *Saccharomyces cerevisiae* selects for cells with improved maltose affinity and hypersensitivity. Appl Environ Microbiol. 2004;70(4):1956-63. pmid:15066785.

Krogerus K, et al. Inheritance of brewing-relevant phenotypes in constructed *Saccharomyces cerevisiae* × *Saccharomyces eubayanus* hybrids. Microb Cell Fact. 2017;16(1):66. pmid:28431563.

Magalhães F, et al. Maltose and maltotriose utilisation by group I strains of the hybrid lager yeast *Saccharomyces pastorianus*. FEMS Yeast Res. 2016;16(5). pmid:27364826.

Nikulin J, et al. Alternative *Saccharomyces* interspecies hybrid combinations and their potential for low-temperature wort fermentation. Yeast. 2018;35: 113-127. pmid:28755430.

Rautio J., et al., 2003 Maltose Transport by Brewer's Yeasts in Brewer's Wort. J. Inst. Brew. 109: 251-261.

Salema-Oom M, et al. Maltotriose utilization by industrial *Saccharomyces* strains: characterization of a new member of the alpha-glucoside transporter family. Appl Environ Microbiol. 2005;71(9):5044-9. pmid:16151085.

Smit A, Dissertation. Maltotriose Transport in Yeast [Internet]. Stellenbosch University. 2007. Available: http://scholar.sun.ac.za/bitstream/handle/10019.1/21760/Smit_Maltotriose_1007.pdf?sequence=1&isAllowed=y.

Smit A, et al. The Thr505 and Ser557 residues of the AGT1-encoded alpha-glucoside transporter are critical for maltotriose transport in *Saccharomyces cerevisiae*. J Appl Microbiol. 2008;104: 1103-11. pmid:18179544.

Stambuk B. U., et al., 2006 Improvement of maltotriose fermentation by *Saccharomyces cerevisiae*. Lett. Appl. Microbiol. 43: 370-376.

Studer. Residue Mutations and their impact on protein structure and function: detecting beneficial and pathogenic changes. Biochem. J. (2013) 449, 581-594.

USPTO, Non-Final Office Action for U.S. Appl. No. 16/378,106, dated May 20, 2020. 27 pages.

Vidgren V, et al. Characterization and functional analysis of the MAL and MPH Loci for maltose utilization in some ale and lager yeast strains. Appl Environ Microbiol. 2005;71(12):7846-57. pmid:16332759.

Vidgren V, et al. Characterization of the *Saccharomyces bayanus*-type AGT1 transporter of lager yeast. J Inst Brew. 2012;118(2):148-51.

Vidgren V, et al. Improved fermentation performance of a lager yeast after repair of its AGT1 maltose and maltotriose transporter genes. Appl Environ Microbiol. 2009;75(8):2333-45. pmid:19181838.

Vidgren V, et al. The temperature dependence of maltose transport in ale and lager strains of brewer's yeast. FEMS Yeast Res. 2010;10(4):402-11. pmid:20402791.

Wang J.-J., et al., 2010 Construction of an industrial brewing yeast strain to manufacture beer with low caloric content and improved flavor. J. Microbiol. Biotechnol. 20: 767-74.

Wang X., et al., 2002 Intracellular maltose is sufficient to induce MAL gene expression in *Saccharomyces cerevisiae*. Eukaryot. Cell 1: 696-703.

Yamakawa S, et al. Repeated batch fermentation from raw starch using a maltose transporter and amylase expressing diploid yeast strain. Appl Microbiol Biotechnol. 2010;87(1):109-15. pmid:20180115.

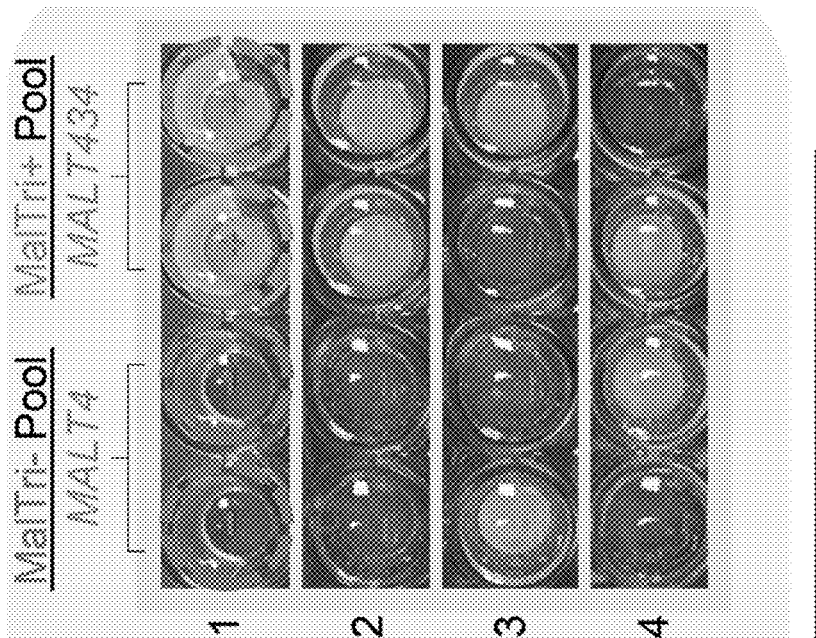
FIG. 3A
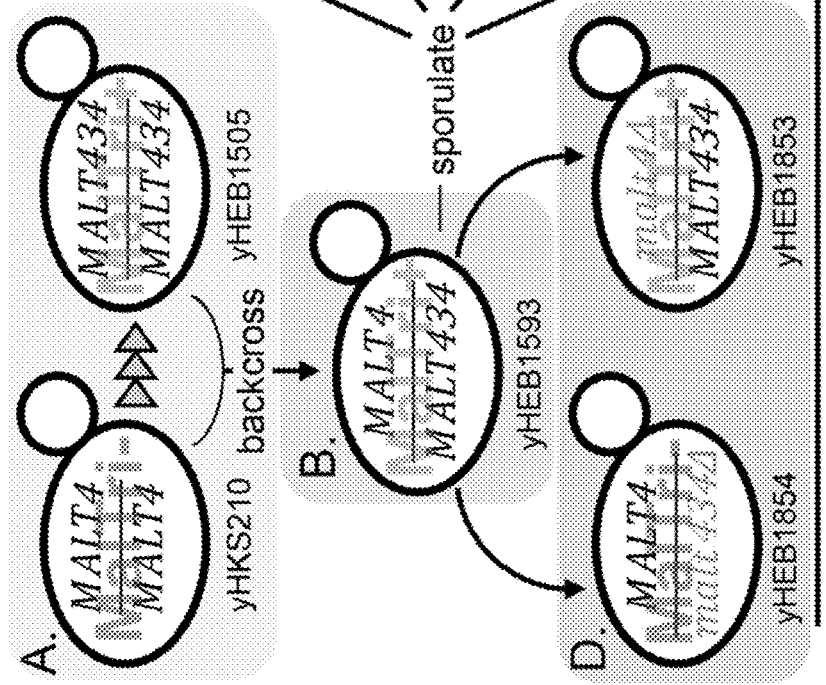
FIG. 3C
FIG. 3B
FIG. 3D

| Strain | Description | Initial OD | Day 3 |
|---|---|---|---|
| yHKS210* | Wild admixture strain | 0.22 (+/-0.01) | 0.68 (+/-0.06) |
| yHKS210 | Wild admixture strain | 0.14 (+/-0.02) | 0.39 (+/- 0.01) |
| yHEB1505 | Single-colony isolate of yHKS210 evolved in maltotriose | 0.16 (+/-0.02) | 1.46 (+/- 0.01) |
| yHEB1593 | yHKS210 x yHEB1505 | 0.12 (+/-0.01) | 1.24 (+/- 0.02) |
| yHEB1854 | yHEB1593 MALT4/malt434Δ | 0.13 (+/-0.01) | 0.39 (+/- 0.01) |
| yHEB1853 | yHEB1593 malt4Δ/MALT434 | 0.11 (+/-0.01) | 1.33 (+/- 0.04) |

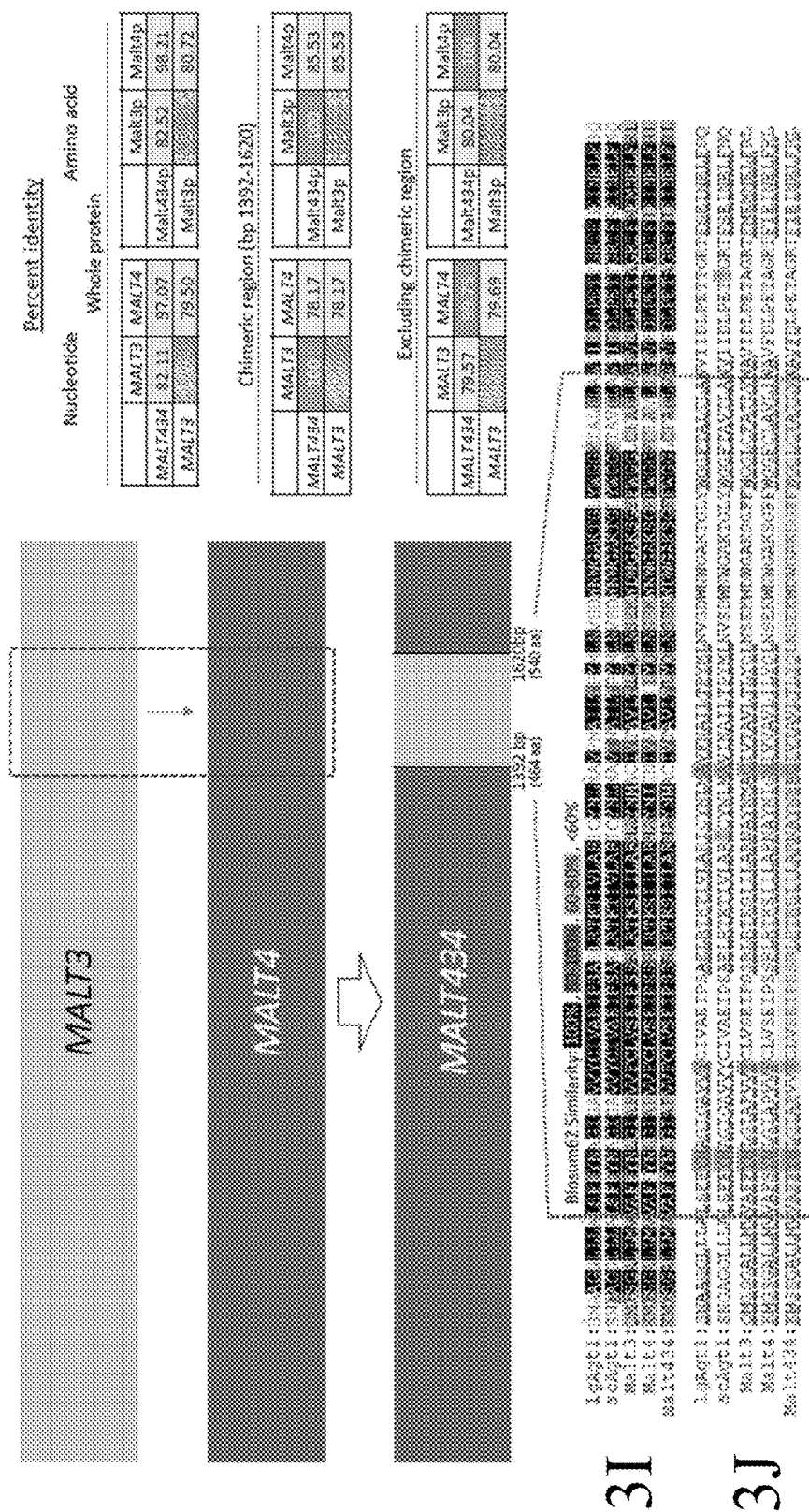

FIG. 5D

| Strain | Plasmid | Initial OD | Day 6 |
|---|---|---|---|
| yHKS210* | - | 0.19 (+/-0.04) | 0.52 (+/-0.03) |
| yHKS210 | - | 0.14 (+/-0.02) | 0.39 (+/-0.05) |
| yHEB1881 | MALT434 | 0.11 (+/-0.01) | 1.31 (+/-0.05) |
| yHRVM108* | - | 0.16 (+/-0.05) | 0.48 (+/-0.01) |
| yHRVM108 | - | 0.12 (+/-0.03) | 0.46 (+/-0.03) |
| yHEB1878 | MALT434 | 0.12 (+/-0.01) | 1.46 (+/-0.04) |

POLYPEPTIDE AND YEAST CELL COMPOSITIONS AND METHODS OF USING THE SAME

CROSS-REFERENCE TO RELATED APPLICATIONS

This patent application is a divisional of U.S. patent application Ser. No. 16/378,106, filed Apr. 8, 2019, and issuing as U.S. Pat. No. 11,028,402 on Jun. 8, 2021, which claims the benefit of priority of U.S. Provisional Patent Application No. 62/654,021, filed Apr. 6, 2018, the entirety of each is incorporated herein by reference in its entirety.

STATEMENT REGARDING FEDERALLY SPONSORED RESEARCH

This invention was made with government support under 17-CRHF-0-6055 awarded by the USDA/NIFA, DEB1253634 awarded by the National Science Foundation and DE-FC02-07ER64494 awarded by the US Department of Energy. The government has certain rights in the invention.

SEQUENCE LISTING

This application includes an electronically submitted Sequence Listing in .txt format. The .txt file contains a sequence listing entitled "2019-06-19_960296-02391 SEQ Listing.txt" and was created on Jun. 19, 2019 and is 73,337 bytes in size. The Sequence Listing contained in this .txt file is part of the specification and is hereby incorporated herein in its entirety.

INTRODUCTION

Polypeptides capable of acting as maltotiose transporters and yeast cells comprising such polypeptides are provided. The resultant yeast cells are capable of growing on maltose and/or maltotriose which has wide-ranging applications.

Brewing yeasts operate at the nexus of science and industry, and there is considerable interest in the discovery and/or development of new strains of *Saccharomyces* (both pure species and hybrids) for commercial brewing and biofuel production (Gibson and Liti 2015; Krogerus et al. 2017a; Gibson et al. 2017; Peris et al. 2017; Hittinger et al. 2018; Denby et al. 2018). Special interest has been given to the development of *Saccharomyces eubayanus* for commercial brewing (Hebly et al. 2015; Krogerus et al. 2015, 2017a; Hittinger et al. 2018). As a hybrid with *S. cerevisiae, S. eubayanus* forms lager-brewing yeasts (Libkind et al. 2011), accounting for more than 90% of the total market and the emphasis on commercial development of this newly discovered addition to the genus *Saccharomyces* (Libkind et al. 2011). Most work in this area has focused on producing synthetic lager-brewing hybrids by mating *S. eubayanus* with *S. cerevisiae* (Hebly et al. 2015; Krogerus et al. 2015, 2016, 2017b; Mertens et al. 2015; Alexander et al. 2016; Nikulin et al. 2018), but there is considerable interest in developing brewing strains of pure *S. eubayanus* as well (Gibson et al. 2017; Hittinger et al. 2018).

A key consideration for any new brewing strain is its ability to rapidly and completely use brewing-related sugars, the most important being maltose, followed by maltotriose and glucose. Of these sugars, maltotriose is by far the most difficult to ferment (Briggs D. E., Brookes P. A., Stevens R. 2004; Eßlinger 2009), even though is comprises around 20% of fermentable sugars in wort (Meussdoerffer and Zarnkow 2009). Maltotriose is poorly utilized or completely unutilized by some brewing strains (Stambuk et al. 2006; Wang et al. 2010; Gibson et al. 2013; Magalhães et al. 2016), leading to large amounts of unconsumed sugar, lower amounts of ethanol, and a cloying flavor that is regarded as undesirable in most beer styles. So far, no strain of *S. eubayanus* isolated from nature has been reported to consume maltotriose (Gibson et al. 2013, 2017; Bing et al. 2014; Hebly et al. 2015; Peris and Langdon et al. 2016; Peris et al. 2014). Accordingly, there is a need in the art for new molecular tools that confer maltotriose utilization in, for example, yeast cells. Additionally, there is a need for new yeast strains, such as in *S. eubayanus*, which are capable of consuming maltotriose as the sole carbon source in a growth media.

SUMMARY

In one aspect, the present invention relates to polypeptides. The polypeptides may include at least 60%, 70%, 75%, 80%, 85%, 90%, 95%, 96%, 97%, 98%, 99% or more sequence identity to SEQ ID NO: 4 (MALT4) and include at least 1, 2, 3, 4, 5, 6, 7, 8, 9, 10, or 11 amino acid substitution(s) to SEQ ID NO: 4 (MALT4) at position(s) S468, I503, G504, N505, V508, I512, N522, F534, L536, V538, or I540; or a functional fragment of the polypeptide thereof. Suitably, the polypeptide may include at least 60%, 70%, 75%, 80%, 85%, 90%, 95%, 96%, 97%, 98%, 99% or 100% sequence identity to either SEQ ID NO: 1 (MALT434) or SEQ ID NO: 2 (MALT433 Chimeric Protein), or a functional fragment of the polypeptide thereof.

In another aspect, polynucleotides encoding any of the polypeptides disclosed herein are provided.

In still another aspect, DNA constructs are provided. The DNA constructs may include a promoter operably linked to any one of the polynucleotides described herein. Alternatively, the DNA constructs may include a heterologous promoter operably linked to a polypeptide having at least 60%, 70%, 75%, 80%, 85%, 90%, 95%, 96%, 97%, 98%, 99% or 100% sequence identity to SEQ ID NO: 6 (1gAGT1), SEQ ID NO: 7 (ncAGT1), SEQ ID NO: 8 (AGT1), or SEQ ID NO: 15 (scAGT1), or a functional fragment of the polypeptide thereof.

In a further aspect, vectors, including any one of the DNA constructs or polynucleotides described herein, are provided. The vectors may include vectors for YACs, plasmids, or vectors for homologous recombination.

In another aspect, yeast cells are provided. The yeast cells may include any one of the polypeptides described herein, any one of the polynucleotides described herein, any one of the DNA constructs described herein, or any one of the vectors described herein. Additionally, yeast cells of the present invention may include yeast cells modified to increase, as compared to a control yeast cell, the expression or maltose/maltotriose transport activity of a maltose/maltotriose transporter polypeptide. In some embodiments, the yeast cell may be a *Saccharomyces eubayanus* cell modified to increase, as compared to a control *Saccharomyces eubayanus* cell, the expression or maltose/maltotriose transport activity of a maltose/maltotriose transporter polypeptide at the plasma membrane of the *Saccharomyces eubayanus* cell.

In still another aspect, the present invention relates to methods for making a fermentation product. The methods may include culturing any one of the yeast cells described herein with a fermentable substrate to produce the fermentation product.

In yet another aspect, methods are provided to select for and isolate maltotriose-utilizing strains of *Saccharomyces eubayanus*.

BRIEF DESCRIPTION OF THE DRAWINGS

FIG. 3A is a schematic of the directed evolution of yHKS210, which was originally unable to use maltotriose (MalTri−). After continuous culturing on maltotriose with a small amount of added glucose, yHKS210 evolved the ability to consume maltotriose (MalTri+). FIG. 3B is a schematic depicting the origins of strain yHEB1593, which is a backcross between yHKS210 and yHEB1505, was also MalTri+. FIG. 3C shows how yHEB1593 was sporulated to test the inheritance of maltotriose utilization. The panel shows a subset of tetrads screened growing on SC+2% maltotriose. Examples of MalTri− spores in Tetrad 1 are circled in red (Left top row), and MalTri+ examples are circled in green (right top row). Whole genome sequencing of MalTri+ and MalTri− pools showed that maltotriose utilization perfectly correlated with the presence/absence of MALT434. FIG. 3D is a schematic of the reciprocal hemizygosity test of the MALT4/MALT434 locus in the backcross strain yHEB1593. FIG. 3G shows a schematic of the origin of MALT434. FIG. 3H shows tables highlighting the percent nucleotide and amino acid identities between the whole protein-coding sequences of MALT3, MALT4, and MALT434, only the chimeric region, and the non-chimeric part of the protein. FIGS. 3I-3J show segments of the alignment of the chimeric region between Malt3 (SEQ ID NO: 5), Malt4 (SEQ ID NO: 4), Malt434 (SEQ ID NO: 1), scAgt1 (SEQ ID NO: 15), and lgAgt1 (SEQ ID NO: 6). The region highlighted in yellow in the Malt434 sequence indicates the chimeric region. The regions underlined with a red dashed line are predicted transmembrane domains. The amino acids highlighted in red are predicted maltose binding residues. The residues highlighted in blue were experimentally found to be important for maltotriose transport by Smit et al. 2008.

FIG. 5D is a table of initial and day-six $OD_{600}$ (OD) measurements of parent strains and strains carrying the MALT434 expression plasmid grown in SC media with maltotriose as the sole carbon and doxycycline to induce plasmid expression. N=3, standard deviation in parentheses. The control was grown in SC+0.04% glucose+doxycycline to reflect the approximate amount of growth expected from contamination with other carbon sources when using 98% pure maltotriose.

DETAILED DESCRIPTION

Figures 1A, 1B:
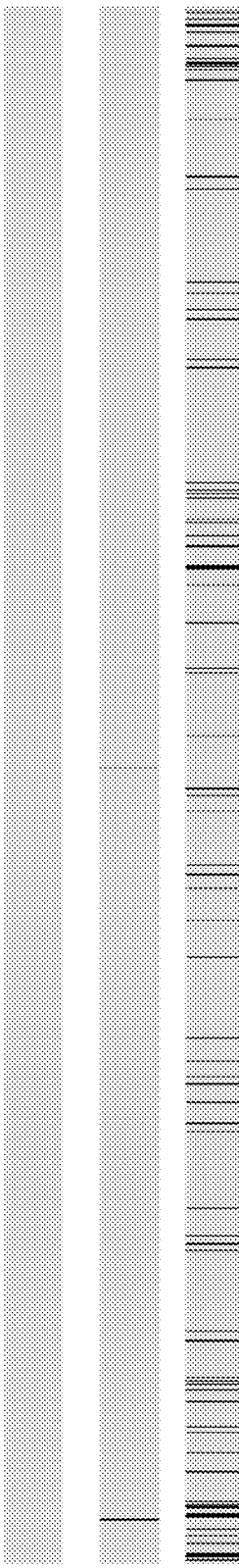
FIG. 1A shows tables highlighting the nucleotide (nuc) and amino acid (aa) percent identities between members of the AGT1 family. Darker colors indicate greater sequence similarity.
FIG. 1B shows multiple sequence alignment between tbAGT1, lgAGT1, and ncAGT1. Black lines indicate nucleotide differences.

Here, the present inventors in the non-limiting Examples used directed evolution to identify strains of *S. eubayanus* that can consume maltotriose or maltose as the sole carbon source in a growth media. The present inventors repeatedly passaged wild strains of *S. eubayanus* for hundreds of generations in 0.1% glucose (so that cells would divide and accumulate mutations) and 2% maltotriose or 2% maltose (to select for advantageous mutations). After directed evolution, the inventors identified strains that evolved the ability to consume maltotriose as the sole carbon source. They further show that in one of their evolved strains this trait is stable, genetically inherited, and maps to a single genetic locus that encodes a novel chimeric MALT3/MALT4 protein. This strain is descended from a wild isolate from Sheboygan, Wis. (yHKS210) that could not originally consume maltotriose, but could consume maltose.

The present inventors also identified six *S. eubayanus* strains (yHEB1585-90) that evolved the ability to consume both maltose and maltotriose. These strains are descended from strain yHRVM108, a wild isolate from Durham, N.C., that could not originally consume either maltose or maltotriose. By identifying these strains and demonstrating that the parent strain contains a gene encoding a maltotriose transporter capable of conferring maltotriose transport when overexpressed in *S. eubayanus*, the inventors have discovered that increasing the expression of AGT1 (alpha-glucoside transporter) or AGT1-related proteins in, for example,

*S. eubayanus* cells, confers the ability to consume maltotriose or maltose as the sole carbon source.

Based on their directed evolution studies, the present inventors demonstrate that increasing the expression or maltose/maltotriose transport activity of maltose/maltotriose transporter proteins in yeast cells, such as *S. eubayanus* cells, is sufficient to allow those yeast cells to consume maltotriose or maltose as the sole carbon source.

Polypeptides

In one aspect, the present invention relates to polypeptides. The polypeptides may include at least 60%, 70%, 75%, 80%, 85%, 90%, 95%, 96%, 97%, 98%, 99% or more sequence identity to SEQ ID NO: 4 (MALT4) and include at least 1, 2, 3, 4, 5, 6, 7, 8, 9, 10, or 11 amino acid substitution(s) to SEQ ID NO: 4 (MALT4) at position(s) S468, I503, G504, N505, V508, I512, N522, F534, L536, V538, or I540; or a functional fragment of the polypeptide thereof.

The polypeptides may include at least 60%, 70%, 75%, 80%, 85%, 90%, 95%, 96%, 97%, 98%, 99% or more sequence identity to SEQ ID NO: 4 (MALT4) and include at least 1, 2, 3, 4, 5, 6, 7, 8, 9, 10, or 11 amino acid substitution(s) to SEQ ID NO: 4 (MALT4) selected from the group consisting of S468F, S468Y, S468W, I503M, I503S, I503C, I503T, G504A, G504V, G504L, G504I, N505C, N505S, N505T, N505M, V508T, V508S, V508C, V508M, I512T, I1512S, I512C, I512M N522D, N522E, F534L, F534I, F534V, F534G, F534A, L536F, L536Y, L536W, V538T, V538S, V538C, V538M, I540V, I540G, I540A, I540L, and I540I.

In some embodiments, the polypeptide may include at least 60%, 70%, 75%, 80%, 85%, 90%, 95%, 96%, 97%, 98%, 99% or more sequence identity to SEQ ID NO: 4 (MALT4) and may include at least 1, 2, 3, 4, 5, 6, 7, 8, 9, 10, or 11 amino acid substitution(s) to SEQ ID NO: 4 (MALT4) selected from the group consisting of S468F, I503M, G504A, N505C, V508T, I512T, N522D, F534L, L536F, V538T, and I540V.

Suitably, the polypeptide may include at least 60%, 70%, 75%, 80%, 85%, 90%, 95%, 96%, 97%, 98%, 99% or 100% sequence identity to any one of SEQ ID NO: 1 (MALT434), SEQ ID NO: 2 (MALT433 Chimeric Protein), or SEQ ID NO: 3 (MALT334 Chimeric Protein), or a functional fragment of the polypeptide thereof.

As used herein, the terms "protein" or "polypeptide" or "peptide" may be used interchangeably to refer to a polymer of amino acids. A "polypeptide" as contemplated herein typically comprises a polymer of naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). The proteins contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation, lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a non-enzymatic attachment of sugars, enzymatic addition such as polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine) are also contemplated.

The polypeptides provided herein are evolved polypeptides representing substitution mutants of the wild-type polypeptide. The polypeptides disclosed herein may include "mutant" polypeptides and variants thereof. As used herein the term "wild-type" is a term of the art understood by skilled persons and means the typical form of an organism, strain, gene or characteristic as it occurs in nature as distinguished from mutant or variant forms. As used herein, a "variant" refers to a polypeptide molecule having an amino acid sequence that differs from a reference protein or polypeptide molecule. A variant may have one or more insertions, deletions, or substitutions of an amino acid residue relative to a reference molecule. A variant may include a fragment of a reference molecule. For example, a polypeptide variant molecule may have one or more insertions, deletions, or substitution of at least one amino acid residue relative to the mutant polypeptides described herein.

The amino acid sequence of the "wild-type" proteins from yeast are presented as SEQ ID NO: 4 (MALT4), SEQ ID NO: 5 (MALT3), SEQ ID NO: 6 (1gAGT1), SEQ ID NO: 7 (ncAGT1), SEQ ID NO: 8 (AGT1), and SEQ ID NO: 15 (scAGT1). Some of the amino acid sequences for evolved mutant polypeptides disclosed herein are provided as SEQ ID NO: 1 (MALT434), SEQ ID NO: 2 (MALT433 Chimeric Protein), and SEQ ID NO: 3 (MALT334 Chimeric Protein). These sequences may be used as reference sequences.

The polypeptides provided herein may be full-length polypeptides (i.e., SEQ ID NOS: 1-8, 15) or may be functional fragments of the full-length polypeptide. As used herein, a "fragment" or "functional fragment" is a portion of an amino acid sequence that is identical in sequence to but shorter in length than a reference sequence. A fragment may comprise up to the entire length of the reference sequence, minus at least one amino acid residue. For example, a fragment may comprise from 5 to 155 contiguous amino acid residues of a reference polypeptide, respectively. In some embodiments, a fragment may comprise at least 5, 10, 15, 20, 25, 30, 40, 50, 60, 70, 80, 90, 100, or 150 contiguous amino acid residues of a reference polypeptide. Fragments may be preferentially selected from certain regions of a molecule. The term "at least a fragment" encompasses the full-length polypeptide. A fragment of a polypeptide may comprise or consist essentially of a contiguous portion of an amino acid sequence of the full-length polypeptide (SEQ ID NOS: 1-8, 15). A fragment may include an N-terminal truncation, a C-terminal truncation, or both truncations relative to the full-length polypeptide. Preferably, a fragment of a polypeptide includes amino acid residues corresponding to amino acid residues 468, 503, 504, 505, 508, 512, 522, 534, 536, 538, or 540 of SEQ ID NO: 4 (MALT4).

The polypeptides disclosed herein may be useful for a variety of reasons. For example, polypeptides which contain the substitutions noted above can be used inter alia for raising antibodies. Such polypeptides are typically less than full-length proteins. Preferably such residues are at least 6, 7, 8, 9, 10, 11, 12, 13, 14, 15, 17, 19, 21, 23, 25, 30, 40, 50 or more residues in length. As an example, if the polypeptide is 6 residues in length, than it can comprise residues including the substitution site. Sufficient residues are desired to form a good immunogen or blocking antigen for use in assays. It may be desirable to conjugate or genetically fuse additional sequences to the polypeptide, for example, to boost immunogenicity, to enhance purification, to facilitate production or expression, or to facilitate detection. Any sequences as are convenient may be used for these or other purposes. The size of these additional sequences may vary greatly, but typically will be at least 2, 4, 6, or 8 amino acid residues in length. Suitably the additional sequences will be less than 100, 90, 80, 70, 60, 50, 40, 30, 20, or 10 amino acids in length.

The polypeptides are also useful for conferring maltotriose utilization to yeast cells such as, without limitation, *S. eubayanus* cells.

A "deletion" in a polypeptide refers to a change in the amino acid sequence that results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide).

"Insertions" and "additions" in a polypeptide refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A variant of a polypeptide may have N-terminal insertions, C-terminal insertions, internal insertions, or any combination of N-terminal insertions, C-terminal insertions, and internal insertions.

Regarding polypeptides, the phrases "percent identity," "% identity," and "% sequence identity" refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

As described herein, variants of the polypeptides disclosed herein may have 60%, 70%, 75%, 80%, 85%, 90%, 95%, 96%, 97%, 98%, 99%, or 100% amino acid sequence identity relative to a reference molecule (e.g., relative to SEQ ID NOS: 1-8, 15). Suitably the MALT protein variants include the MALT4 substitution mutations identified herein.

Polypeptide sequence identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70, or at least 150 contiguous residues. Such lengths are exemplary only, and it is understood that any fragment length supported by the sequences shown herein, in the tables, figures, or Sequence Listing, may be used to describe a length over which percentage identity may be measured.

The amino acid sequences of the polypeptide variants as contemplated herein may include conservative amino acid substitutions relative to a reference amino acid sequence. For example, a variant or derivative polypeptide may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The amino acid sequences of the polypeptide variants as contemplated herein may include modifications made apparent by a sequence alignment of the polypeptides disclosed herein and other polypeptides. A person of ordinary skill in the art may easily align the polypeptides disclosed herein with other polypeptides from, for example, other species to determine what additional variants (i.e. substitutions, insertions, deletions, etc.) could be made to the polypeptides. For example, a person of ordinary skill in the art would appreciate that modifications in a reference polypeptide (i.e., SEQ ID NOS: 1-8, 15) could be based on alternative amino acid residues that occur at the corresponding position in other homologous polypeptides from other species or strains.

The disclosed polypeptides, mutants, or variants described herein may have one or more functional or biological activities exhibited by a reference polypeptide (e.g., one or more functional or biological activities exhibited by SEQ ID NOS: 1-8). For example, the disclosed polypeptides, mutants, variants, or derivatives thereof may have increased maltotriose transport activity or localization to a particular part a cell.

Polynucleotides

In another aspect, polynucleotides encoding any of the polypeptides disclosed herein are also provided. The terms "polynucleotide," "polynucleotide sequence," "nucleic acid," and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

Isolated polynucleotides homologous to the polynucleotides described herein are also provided. Those of skill in the art also understand the degeneracy of the genetic code and that a variety of polynucleotides can encode the same polypeptide. In some embodiments, the polynucleotides may be codon-optimized for expression in a particular cell such as, without limitation, a yeast cell. While particular nucleotide sequences, which are found in yeasts, are disclosed herein any nucleotide sequences may be used which encode a desired form of the substituted polypeptides described herein. Thus non-naturally occurring sequences may be used. These may be desirable, for example, to enhance expression in heterologous expression systems of polypeptides or proteins. Computer programs for generating degenerate coding sequences are available and can be used for this purpose as well as other means.

In some embodiments, the polynucleotide may include at least 60%, 70%, 75%, 80%, 85%, 90%, 95%, 96%, 97%, 98%, 99% or 100% to SEQ ID NO: 9 (MALT434 polynucleotide sequence).

The isolated polynucleotides or polypeptides provided herein may be prepared by methods available to those of skill in the art. Isolated indicates that the polynucleotides or proteins are not in their naturally occurring state. Such preparations may be cell-free preparations. The polynucleotide or polypeptides may be extracted from the cells by breaking the cell membrane and optionally removing non-desired components. The polypeptides may be made as secreted polypeptides and further isolated using means known to those of skill in the art. Alternatively, desired proteins or nucleic acids can be purified using sequence-specific reagents, including but not limited to oligonucleotide probes, primers, and antibodies. Techniques for isolating cell-free preparations are well known in the art, and any that are convenient can be used. The term "substantially isolated or purified" refers to polypeptides or polynucleotides that are removed from their natural environment, and are at least 60% free, preferably at least 75% free, and more preferably at least 90% free, even more preferably at least 95% free from other components with which they are naturally associated.

DNA Constructs

In still another aspect, DNA constructs are provided. The DNA constructs may include a promoter operably linked to any one of the polynucleotides described herein. The promoter may be a heterologous promoter or an endogenous promoter associated with the polypeptide described herein.

Additionally, the DNA constructs may include a heterologous promoter operably linked to a polypeptide having at least 60%, 70%, 75%, 80%, 85%, 90%, 95%, 96%, 97%, 98%, 99% or 100% sequence identity to SEQ ID NO: 6 (1gAGT1), SEQ ID NO: 7 (ncAGT1), SEQ ID NO: 8 (AGT1), or SEQ ID NO: 15 (scAGT1), or a functional fragment of the polypeptide thereof.

As used herein, the term "DNA construct" refers to recombinant DNA polynucleotides which may be single-stranded or double-stranded and may represent the sense or the antisense strand. Recombinant polynucleotides are polynucleotides formed by laboratory methods that include polynucleotide sequences derived from at least two different natural sources or they may be synthetic. Constructs thus may include new modifications to endogenous genes introduced by, for example, genome-editing technologies. Constructs may also include recombinant polynucleotides created using, for example, recombinant DNA methodologies.

The DNA constructs provided herein may be prepared by methods available to those of skill in the art. Notably each of the DNA constructs claimed are recombinant molecules and as such do not occur in nature. Generally, the nomenclature used herein and the laboratory procedures utilized in the present invention include molecular, biochemical, and recombinant DNA techniques that are well known and commonly employed in the art. Standard techniques available to those skilled in the art may be used for cloning, DNA and RNA isolation, amplification, and purification. Such techniques are thoroughly explained in the literature.

As used herein, the terms "heterologous promoter," "promoter," "promoter region," or "promoter sequence" refer generally to transcriptional regulatory regions of a gene, which may be found at the 5' or 3' side of the polynucleotides described herein, or within the coding region of the polynucleotides, or within introns in the polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease Si), as well as protein binding domains (consensus sequences) responsible for the binding of RNA polymerase.

In some embodiments, the disclosed polynucleotides are operably connected to the promoter. As used herein, a polynucleotide is "operably connected" or "operably linked" when it is placed into a functional relationship with a second polynucleotide sequence. For instance, a promoter is operably linked to a polynucleotide if the promoter is connected to the polynucleotide such that it may effect transcription of the polynucleotides. In various embodiments, the polynucleotides may be operably linked to at least 1, at least 2, at least 3, at least 4, at least 5, or at least 10 promoters.

Heterologous promoters useful in the practice of the present invention include, but are not limited to, constitutive, inducible, temporally-regulated, developmentally regulated, chemically regulated, tissue-preferred and tissue-specific promoters. The heterologous promoter may be a yeast, fungal, or bacterial promoter. In yeast cells, typical promoters include, without limitation, galactose inducible promoters (i.e., GAL1) and doxycycline-inducible promoters. Other promoters include the T3, T7, and SP6 promoter sequences, which are often used for in vitro transcription of RNA. Those of skill in the art are familiar with a wide variety of additional promoters for use in various cell types.

Vectors

In a further aspect, vectors, including any one of the DNA constructs or polynucleotides described herein, are provided. The term "vector" is intended to refer to a polynucleotide capable of transporting another polynucleotide to which it has been linked. In some embodiments, the vector may be a "plasmid," which refers to a circular double-stranded DNA loop into which additional DNA segments may be ligated. Certain vectors are capable of autonomous replication in a host cell into which they are introduced (e.g., yeast vectors having an origin of replication). Other vectors can be integrated into the genome of a host cell upon introduction into the host cell, and thereby are replicated along with the host genome, such as some viral vectors or transposons. Yeast artificial chromosomes or YACS represent another suitable vector for use herein. Vectors may carry genetic elements, such as those that confer resistance to certain drugs or chemicals.

Yeast Cells

In another aspect, yeast cells are provided. The yeast cells may include any one of the polypeptides described herein, any one of the polynucleotides described herein, any one of the DNA constructs described herein, or any one of the vectors described herein.

The "yeast cells" disclosed herein may be, without limitation, ascomycetes and fungi that lack fruiting bodies or experience yeast phases of their life cycles. Suitable yeast species may be from the family Saccharomycetaceae. In some embodiments, the yeast species are from the genus *Saccharomyces*. Suitable *Saccharomyces* species may include, without limitation, *Saccharomyces eubayanus, Saccharomyces cerevisiae, Saccharomyces paradoxus, Saccha-* romyces mikatae, Saccharomyces arboricola, Saccharomyces kudriavzevii, Saccharomyces jurei, and Saccharomyces uvarum. Suitable Saccharomyces species may also include any taxonomic synonyms of these species or any newly discovered species to be members of the genus Saccharomyces.

In some embodiments, the yeast cell may be selected from unevolved yeast strains such as, without limitation, yHKS210, yHRVM108, FM1318, CRUB 1568$^T$=PYCC 6148$^T$=CBS 12357$^T$. These strains may be modified with the compositions and according to the methods disclosed herein.

In some embodiments, the yeast cell may be an evolved yeast strain such as, without limitation, yHEB1505, yHEB1506, yHEB1585, yHEB1586, yHEB1587, yHEB1588, yHEB1589, or yHEB1590.

The yeast cells of the present invention may be modified to increase, as compared to a control yeast cell, the expression or maltose/maltotriose transport activity of a maltose/maltotriose transporter polypeptide. Based on their directed evolution studies, the present inventors demonstrate that increasing the expression or maltose/maltotriose transport activity of maltose/maltotriose transporter proteins in yeast cells is sufficient to allow those yeast cells to consume maltotriose or maltose as the sole carbon source.

The present inventors conjecture that the findings from their directed evolution studies suggest that increasing the expression or maltose/maltotriose transport activity of a maltose/maltotriose transporter protein at the plasma membrane of a yeast cell would allow the yeast cell to consume maltotriose or maltose as the sole carbon source. In other words, yeast cells have the enzymes and other proteins necessary to use maltotriose or maltose as a carbon source internally, but some yeast cells may lack the ability to grow on maltotriose or maltose because the cells lack the ability to transport the maltotriose or maltose across the plasma membrane of the yeast cell. Accordingly, in some embodiments, the modified yeast cells may have increased expression or increased maltose/maltotriose transport activity of the maltose/maltotriose transporter polypeptide, as compared to a control yeast cell, at the plasma membrane of the yeast cell.

The increased maltose/maltotriose transport activity or expression of the maltose/maltotriose transporter polypeptide is relative to a "control yeast cell." A "control yeast cell" is a yeast cell that has not been modified as described herein. Exemplary control yeast cells may include, without limitation, the unevolved yeast strains used by the inventors in the non-limiting Examples, such as FM1318, CRUB 1568$^T$=PYCC 6148$^T$=CBS 12357$^T$, yHKS210, or yHRVM108.

As used herein, "maltose/maltotriose transport activity" refers to the ability of a maltose/maltotriose transporter polypeptide to transport maltose or maltotriose across a membrane. In some embodiments, the maltose/maltotriose transport activity of the maltose/maltotriose transporter polypeptide is increased by at least 30%, 40%, 50%, 55%, 60%, 65%, 70%, 75%, 80%, 85%, 90%, 95%, 100%, 150%, 200%, 300%, 500% or 1000% as compared to a control yeast cell.

As used herein, the term "expression" may refer either to the levels of an RNA encoding a protein in a cell or the levels of the protein in a cell. In some embodiments, the expression of the maltose/maltotriose transporter polypeptide is increased by at least 30%, 40%, 50%, 55%, 60%, 65%, 70%, 75%, 80%, 85%, 90%, 95%, 100%, 150%, 200%, 300%, 500% or 1000% as compared to a control yeast cell.

The yeast cells may be modified to increase as compared to a control yeast cell the maltose/maltotriose transport activity or expression of a maltose/maltotriose transporter polypeptide. As used herein, the terms "modified" or "modifying" refer to using any laboratory methods available to those of skill in the art including, without limitation, directed evolution, genetic engineering techniques (i.e. CRISPR/Cas techniques or gene overexpression technologies), traditional breeding/selection techniques, or forward genetic techniques to affect the maltose/maltotriose transport activity or expression of a maltose/maltotriose transporter polypeptide. It will be readily apparent to one of ordinary skill in the art that there are multiple potential ways to increase the maltose/maltotriose transport activity or expression of a maltose/maltotriose transporter polypeptide, by modifying the gene encoding the maltose/maltotriose transporter polypeptide, for example, introducing targeted mutations, by modifying a mRNA (or levels thereof) encoding the maltose/maltotriose transporter polypeptide, for example, gene overexpression techniques.

In some embodiments, the yeast cell may be modified to increase the expression or maltose/maltotriose transport activity of a maltose/maltotriose transporter polypeptide by introducing into the yeast cell, using for example techniques known in the art, any one of the polypeptides described herein, any one of the polynucleotides described herein, any one of the DNA constructs described herein, or any one of the vectors described herein or via combinations thereof. For example the expression of the maltose/maltotriose transporter may be increased and the activity of the maltose/maltotriose transporter may also be increased by combining the mutations in the polypeptides described herein.

The yeast may also be modified to introduce a hypermorphic mutation(s) in a polynucleotide (i.e., gene) encoding the maltose/maltotriose transporter polypeptide. A "hypermorphic mutation" is an alteration in a gene that results in an increased level of activity, or in which the wild-type gene product is expressed at an increased level. It will be readily apparent to those of skill in the art that a variety of hypermorphic mutations may be introduced (using, for example, directed evolution, CRISPR/Cas or other genome engineering techniques) into a polynucleotide encoding the maltose/maltotriose transporter polypeptide described herein to arrive at embodiments of the present invention. For example, a person of ordinary skill may introduce alterations (i.e., substitutions or deletions) into the promoter of a gene encoding a maltose/maltotriose transporter polypeptide described herein that result in additional expression of the maltose/maltotriose transporter polypeptide. Still further modifications contemplated herein include mutations that impact one or more of the domains of the maltose/maltotriose transporter polypeptide.

As used herein, a "maltose/maltotriose transporter polypeptide" may include any polypeptide that can transport maltose or maltotriose across a membrane. Suitable maltose/maltotriose transporter polypeptides may include, without limitation, AGT1 or AGT-like (alpha-glucoside transporter), MTT1/MTY1, or MPH polypeptides. In some embodiments, the maltose/maltotriose transporter protein may include a polypeptide having at least 60%, 70%, 75%, 80%, 85%, 90%, 95%, 96%, 97%, 98%, 99% or 100% sequence identity to SEQ ID NO: 6 (1gAGT1), SEQ ID NO: 7 (ncAGT1), SEQ ID NO: 8 (AGT1), or SEQ ID NO: 15 (scAGT1), or a functional fragment of the maltose/maltotriose transporter protein thereof.

In some embodiments, the yeast cell may be a Saccharomyces eubayanus cell modified to increase, as compared to a control *Saccharomyces eubayanus* cell, the expression or maltose/maltotriose transport activity of a maltose/maltotriose transporter polypeptide at the plasma membrane of the *Saccharomyces eubayanus* cell.

Methods for Making a Fermentation Product

In a still further aspect, the present invention relates to methods for making a fermentation product. The methods may include culturing any one of the yeast cells described herein with a fermentable substrate to produce the fermentation product.

As used herein, "culturing" refers to mixing the yeast cells into any medium including a fermentable substrate.

The fermentable substrate may include maltose or maltotriose. In some embodiments, the fermentable substrate may include wort or malt extract.

The fermentation product may be a beer product, a wine product, an alcoholic beverage, a biochemical, or a biofuel. In some embodiments, the fermentation product is a lager beer.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1—Old and New Maltotriose Transporters in *Saccharomyces eubayanus*

Previous studies have shown that the primary hindrance to maltotriose utilization in *Saccharomyces* is the inability of cells to transport the sugar across the plasma membrane (Wang et al. 2002; Rautio and Londesborough 2003). In yeasts that are capable of maltotriose consumption, the sugar is taken up by a small number maltose transporters encoded by genes in the MALT family (Han et al. 1995; Dietvorst et al. 2005; Salema-Oom et al. 2005; Brown et al. 2010). While a number of transporters in this family have been characterized that can carry maltose and other sugars (Brown et al. 2010), maltotriose transporters are more rare, reflecting the general difficultly of transporting higher molecular weight sugars, such as dextrins and starch (Barnett 1992; Briggs D. E., Brookes P. A., Stevens R. 2004 p. 123,125). Here we characterize native MALT genes found in *S. eubayanus* for their ability to enable the transport of maltotriose and describe a novel chimeric maltotriose transporter that resulted from directed evolution of *S. eubayanus* for maltotriose consumption.

Materials and Methods

Strains

All strains discussed in this paper are listed in Table 1. Briefly, FM1318 is a monosporic derivative of the type strain of *S. eubayanus* (CRUB 1568$^T$=PYCC 6148$^T$=CBS 12357$^T$), which was isolated from Patagonia (Libkind et al.

2011). yHRVM108 was isolated from Durham, N.C. and is closely related to the *S. eubayanus* strains that hybridized with *S. cerevisiae* to give rise to lager-brewing yeasts (Peris & Langdon et al., 2016). yHKS210 was isolated from Sheboygan, Wis. and is an admixture between populations A and B of *S. eubayanus* (Peris et al. 2014). Of these strains, FM1318 and yHKS210 grew well on maltose, but did not grow on maltotriose. yHRVM108 grew sluggishly on maltose and did not grow on maltotriose (Table 1). yHAB47 is synonymous with Weihenstephan 34/70 (Peris & Langdon et al., 2016), a representative of the Frohberg or Group II (Magalhães et al. 2016) lineage of lager-brewing hybrids. CDFM21L.1 is a strain of *S. eubayanus* isolated from Tibet (Bing et al. 2014) and closely related to yHRVM108. Of known *S. eubayanus* strains, CDFM21L.1 is the most genetically similar to the *S. eubayanus* parents of lager-brewing hybrids.

TABLE 1

Strains and plasmids used in this Example

| Strain | Species | Background | Relavent genotype | MAL | MalTri | Description | Source |
|---|---|---|---|---|---|---|---|
| FM1318 | *S. eubayanus* | — | — | + | − | monosporic derivative of the type strain of *S. eubayanus* | Libkind & Hittinger et al. (*PNAS*,2011) |
| yHRVM108 | *S. eubayanus* | — | — | (+/−) | − | Member of the holoartic subpopulation population of isolated from Durham, North Carolina | Peris & Langdon et al. (*PLOS Genetics*,2016) |
| yHKS210 | *S. eubayanus* | — | MALT4/ MALT4 | + | − | Admixture of *S. eubayanus* populations A and B isolated from Sheboygan, Wisconsin | Peris et al. (*Molecular Ecology*, 2014) |
| yHEB1403 | *S. eubayanus* | yHKS210 | — | + | + | Sample taken from the 86th passage of yHKS210. | This study |
| yHEB1505 | *S. eubayanus* | yHKS210 | MALT434/ MALT434 | + | + | single colony isolate taken from the evolution of yHKS210 in maltotriose after 86 passages. | This study |
| yHEB1506 | *S. eubayanus* | yHKS210 | — | + | + | single colony isolate taken from the evolution of yHKS210 in maltotriose after 86 passages | This study |
| yHEB1593 | *S. eubayanus* | yHKS210 × yHEB1505 | MALT434/ MALT4 | + | + | Backcross between yHEB1505 and yHKS210 | This study |
| yHEB1853 | *S. eubayanus* | yHKS210 × yHEB1505 | MALT434/ malt4Δ:: NatMX | + | + | yHEB1593 with original MALT4 allele replaced with NatMX marker | This study |
| yHEB1854 | *S. eubayanus* | yHKS210 × yHEB1505 | malt434Δ:: NatMX/ MALT4 | + | − | yHEB1593 with chimeric MALT434 allele replaced with NatMX marker | This study |
| yHEB1881 | *S. eubayanus* | yHKS210 | MALT4/ MALT4 [pBM5155- MALT434] | + | + | yHKS210 with pBM5155 based plasmid for MALT434 expression | This study |
| yHEB1878 | *S. eubayanus* | yHRVM108 | [pBM5155- MALT434] | + | + | yHRVM108 with pBM5155 based plasmid for MALT434 expression | This study |
| yHEB1870 | *S. eubayanus* | yHRVM108 | [pBM5155- MALT1] | (+/−) | − | yHRVM108 with pBM5155 based plasmid for MALT1 expression | This study |

TABLE 1-continued

Strains and plasmids used in this Example

| Strain | Species | Background | Relavent genotype | MAL | MalTri | Description | Source |
|---|---|---|---|---|---|---|---|
| yHEB1872 | S. eubayanus | yHRVM108 | [pBM5155-MALT3] | (+30/−) | − | yHRVM108 with pBM5155 based plasmid for MALT3 expression | This study |
| yHEB1877 | S. eubayanus | yHRVM108 | [pBM5155-MALT2/4] | (+/−) | − | yHRVM108 with pBM5155 based plasmid for MALT2/4 expression | This study |
| yHEB1885 | S. eubayanus | yHRVM108 | [pBM5155-IgAGT1] | + | + | yHRVM108 with pBM5155 based plasmid for AGT1 from lager brewing yeast expression | This study |
| yHEB1882 | S. eubayanus | yHKS210 | [pBM5155-IgAGT1] | + | + | yHKS210 with pBM5155 based plasmid for expression of the lager allele of AGT1 | This study |
| yHEB1883 | S. eubayanus | yHRVM108 | [pBM5155-ncAGT1] | + | + | yHRVM108 with pBM5155 based plasmid for expression of the North Carolinian Allele of AGT1 | This study |
| yHEB1884 | S. eubayanus | yHRVM108 | [pBM5155-IgAGT1] | + | + | yHRVM108 with pBM5155 based plasmid for expression of the lager brewing yeast allele of AGT1. | This study |
| yHAB47 | S. eubayanus × S. cerevisiae | — | — | + | + | Weihenstephan 34/70; Frohberg lineage of lager brewing yeast hybrids *(Magalhães et al. 2016) | Peris & Langdon et al. (*PLOS Genetics*, 2016) |
| yHEB1585 | S. eubayanus | yHRVM108 | — | + | + | single colony isolate taken from replicate A of the evolution of yHRVM108 in maltose after 86 passages. | This study |
| yHEB1586 | S. eubayanus | yHRVM108 | — | + | + | single colony isolate taken from replicate A of the evolution of yHRVM108 in maltose after 86 passages. | This study |
| yHEB1587 | S. eubayanus | yHRVM108 | — | + | + | single colony isolate taken from replicate A of the evolution of yHRVM108 in maltose after 86 passages. | This study |
| yHEB1588 | S. eubayanus | yHRVM108 | — | + | + | single colony isolate taken from replicate B of the evolution of yHRVM108 in maltose after 86 passages. | This study |
| yHEB1589 | S. eubayanus | yHRVM108 | — | + | + | single colony isolate taken from replicate B of the evolution of yHRVM108 in maltose after 86 passages. | This study |
| yHEB1590 | S. eubayanus | yHRVM108 | — | + | + | single colony isolate taken from replicate B of the evolution of yHRVM108 in maltose after 86 passages. | This study |

TABLE 1-continued

Strains and plasmids used in this Example

| Strain | Species | Background | Relavent genotype | MAL | MalTri | Description | Source |
|---|---|---|---|---|---|---|---|
| yHEB1778 | S. eubayanus | yHRVM108 | — | + | − | Single-colony isolate taken from replicate C of the evolution of yHRVM108 in maltose after 86 passages. | This study |
| yHEB1779 | S. eubayanus | yHRVM108 | — | + | − | Single-colony isolate taken from replicate C of the evolution of yHRVM108 in maltose after 86 passages. | This study |
| yHEB1780 | S. eubayanus | yHRVM108 | — | + | − | Single-colony isolate taken from replicate C of the evolution of yHRVM108 in maltose after 86 passages. | This study |
| pBM5155 | plasmid | — | — | na | na | plasmid for doxycycline inducible gene expression (Gen Bank KT725394.1) | Alexander et al. 2016 (Fungal Genet. Biol) |
| pHEB7 | plasmid | — | — | na | na | pBM5155 with ncAGT1 gap repaired into the NotI site | This study |
| pHEB11 | plasmid | — | — | na | na | pBM5155 with lgAGT1 gap repaired into the NotI site | This study |
| pHEB16 | plasmid | — | — | na | na | pBM5155 with MALT1 gap repaired into the NotI site | This study |
| pHEB17 | plasmid | — | — | na | na | pBM5155 with MALT3 gap repaired into the NotI site | This study |
| pHEB18 | plasmid | — | — | na | na | pBM5155 with MALT4 gap repaired into the NotI site | This study |
| pHEB19 | plasmid | — | — | na | na | pBM5155 with MALT434 gap repaired into the NotI site | This study |

Identification of MALT Genes

Previously, we identified four genes with homology to the genes encoding the maltose transporters of S. cerevisiae and lager-brewing hybrids in the genome assembly of FM1318 published by Baker et al. 2015. These genes were previously designated MALT1-4. Only a partial contig was available for MALT4 in this assembly, but a BLAST (Altschul et al. 1997) search of the Okuno et al. 2016 assembly of the type strain of S. eubayanus (of which FM1318 is a monosporic derivative) allowed us to annotate the full-length sequence of MALT4. MALT4 has 99.7% identity to MALT2 at the nucleotide level and 100% identity at the amino acid level. The regions from 900 bp downstream of MALT2 and MALT4 and upstream to the ends of chromosomes V and XVI (regions of approximately 12 kb in the Okuno et al. 2016 assembly), respectively, share 99.1% nucleotide identity. The 10 kb outside of this region only share 49.8% nucleotide identity. Thus, MALT2 and MALT4 are close paralogs that are likely related by a recent subtelomeric duplication and/or translocation event.

Reads for homologs of AGT1 were retrieved using the functional AGT1 sequence from lager yeast (lgAGT1) as the query sequence (Nakao et al. 2009) in a BLAST search of the SRA databases of NCBI for yHRVM108 (SRR2586159) and CDFM21 L.1(SRR1507225). All reads identified in the BLAST searches were downloaded and assembled using the de novo assembler in Geneious v. 9.0.3 http://www.geneious.com, Kearse et al., 2012). The homologs identified in yHRVM108 and CDFM21L.1 were designated ncAGT1 (for North Carolinian AGT1) and tbAGT1 (for Tibetan AGT1) respectively. The presence and sequence of ncAGT1 in yHRVM108 was further verified by PCR amplification and Sanger sequencing (Table 2). CDFM21L.1 was not available at the time of this work for further verification of the presence of tbAGT1.

TABLE 2

Oligonucleotides used in this Example

| Name | Sequence | Description |
|---|---|---|
| oHECPB75 | TATAGACACGCAAACACAAATACACACACTAA ATTAATGAAGGGATTATCCTCATTAATA (SEQ ID NO: 17) | amplifies MTT1 for cloning into pBM5155 over NotI site by gap repair |
| oHECPB76 | TCAAGAAATTCGCTTATTTAGAAGTGGCGCGA ATTCACTATCATTTGTTCACAACAGATG (SEQ ID NO: 18) | amplifies MTT1 for cloning into pBM5155 over NotI site by gap repair |
| oHECPB77 | CACGCAAACACAAATACACACACTAAATTAAT GAAAAATATACTTTCGCTGGTAGGAAGA (SEQ ID NO: 19) | amplifies IgAGT1 for cloning into pBM5155 over NotI site by gap repair |
| oHECPB78 | CAAGAAATTCGCTTATTTAGAAGTGGCGCGAA TTCACTATCATAACGCCTGTTGACTCGC (SEQ ID NO: 20) | amplifies IgAGT1 for cloning into pBM5155 over NotI site by gap repair |
| oHECPB104 | ACACGCAAACACAAATACACACACTAAATT AATGAAGAATATCATTTCGCTGGTAAGAA G (SEQ ID NO: 21) | amplifies ncAGT1 for cloning into pBM5155 over NotI site by gap repair |
| oHECPB105 | GAAATTCGCTTATTTAGAAGTGGCGCGAA TTCACTATTATAATGCCTGCTGACTCATGCT (SEQ ID NO: 22) | amplifies ncAGT1 for cloning into pBM5155 over NotI site by gap repair |
| oHECPB124 | CCTATGCTTCTGAAGTTTGC (SEQ ID NO: 23) | primer to confirm sequence of IgAGT1 and ncAGT1 in pBM5155 |
| oHECPB125 | CCTGCCAAACCAAGACAG (SEQ ID NO: 24) | primer to confirm sequence of IgAGT1 and ncAGT1 in pBM5155 |
| oHECPB128 | GCTTGTTTATGTTGGGTCGGTC (SEQ ID NO: 25) | primer to confirm sequence of MTT1 in pBM5155 |
| oHECPB129 | GACCGACCCAACATAAACAAGC (SEQ ID NO: 26) | primer to confirm sequence of MTT1 in pBM5155 |
| oHECPB138 | ACACGCAAACACAAATACACACACTAAATTAA TGAAGGGTCTATCCTCAATGATAAATAG (SEQ ID NO: 27) | amplifies MALT4 (and or MALT2) from *S. eubayanus* for cloning into pBM5155 over NotI site by gap repair |
| oHECPB139 | CGCTTATTTAGAAGTGGCGCGAATTCACTATC AATCCATTAGAGATGGGGTGCTTTGCTC (SEQ ID NO: 28) | amplifies MALT4 (and or MALT2) from *S. eubayanus* for cloning into pBM5155 over NotI site by gap repair |
| oHECPB140 | CACGCAAACACAAATACACACACTAAATTAAT GAAGGGTCTATCTTCAATATTGAATAGA (SEQ ID NO: 29) | amplifies MALT1 from *S. eubayanus* for cloning into pBM5155 over NotI site by gap repair |
| oHECPB141 | CGCTTATTTAGAAGTGGCGCGAATTCACTATC AAATCGTAAGAGATGGGGTAGTTAATTC (SEQ ID NO: 30) | amplifies MALT1 from *S. eubayanus* for cloning into pBM5155 over NotI site by gap repair |
| oHECPB142 | CACGCAAACACAAATACACACACTAAATTAAT GAAGGGCTTATCCTCACTGATAAACAGA (SEQ ID NO: 31) | amplifies MALT3 from *S. eubayanus* for cloning into pBM5155 over NotI site by gap repair |
| oHECPB143 | CGCTTATTTAGAAGTGGCGCGAATTCACTATC ATAAATTCGTAATAGATGGTGTGCTTCG (SEQ ID NO: 32) | amplifies MALT3 from *S. eubayanus* for cloning into pBM5155 over NotI site by gap repair |
| oHECPB156 | ATATTATGGTAGATATGACCTTTACG (SEQ ID NO: 33) | primer to confirm sequence of MALT2/4 in pBM5155 |
| oHECPB157 | GGTTGATTTCATCAGAGATTGCTTTGG (SEQ ID NO: 34) | primer to confirm sequence of MALT2/4 in pBM5155 |
| oHECPB158 | CGTAAAGGTCATATCTACCATAATAT (SEQ ID NO: 35) | primer to confirm sequence of MALT2/4 in pBM5155 |
| oHECPB159 | CCAATGTCTGACTGTGTCTTATGCCTC (SEQ ID NO: 36) | primer to confirm sequence of MALT2/4 in pBM5155 |
| oHECPB160 | GAGGCATAAGACACAGTCAGACATTGG (SEQ ID NO: 37) | primer to confirm sequence of MALT2/4 in pBM5155 |

TABLE 2-continued

Oligonucleotides used in this Example

| Name | Sequence | Description |
|---|---|---|
| oHECPB161 | CTGTCTTGGTTTGGCAGG (SEQ ID NO: 38) | primer to confirm sequence of IgAGT1 and ncAGT1 in pBM5155 |
| oHECPB162 | CTGTGAAAGTTTAGGGATGATTGCGG (SEQ ID NO: 39) | primer to confirm sequence of MALT1 in pBM5155 |
| oHECPB163 | CCGCAATCATCCCTAAACTTTCACAG (SEQ ID NO: 40) | primer to confirm sequence of MALT1 in pBM5155 |
| oHECPB164 | CCTGTATATGTTGGATCGGTCAAAC (SEQ ID NO: 41) | primer to confirm sequence of MALT1 in pBM5155 |
| oHECPB165 | GTTTGACCGATCCAACATATACAGG (SEQ ID NO: 42) | primer to confirm sequence of MALT1 in pBM5155 |
| oHECPB166 | CCTTTGGCTTTAAGATACTACC (SEQ ID NO: 43) | primer to confirm sequence of MALT3 in pBM5155 |
| oHECPB167 | GGTAGTATCTTAAAGCCAAAGG (SEQ ID NO: 44) | primer to confirm sequence of MALT3 in pBM5155 |
| oHECPB168 | GGATGCTCTGATACTCACGG (SEQ ID NO: 45) | primer to confirm sequence of MALT3 in pBM5155 |
| oHECPB169 | CCGTGAGTATCAGAGCATCC (SEQ ID NO: 46) | primer to confirm sequence of MALT3 in pBM5155 |
| oHECPB170 | GGARAGTGATACCTTATCATCTGCTGCGCTAA GAGTCAAGATCTGTTTAGCTTGCCTT (SEQ ID NO: 47) | amplifies MX-driven drug markers with overhangs to the MALT4 and MALT2 loci for allele replacement by homologous recombination |
| oHECPB171 | ACTCAAAAAAAATTCCAAAAGCTATTAGGTAA CTGAGCTCGTTTTCGACACTGGAT (SEQ ID NO: 48) | amplifies MX-driven drug markers with overhangs to the MALT4 and MALT loci for allele replacement by homologous recombination |
| oHECPB172 | CGATATTTCCGCCGCAGCCCGAG (SEQ ID NO: 49) | specifically amplifies the MALT2 locus when used with primers oHECPB159 or oHECPB156 |
| oHECPB173 | CTTAGTAGCAGCGACATATTCAAG (SEQ ID NO: 50) | specifically amplifies the MALT4 locus when used with primers oHECPB159 or oHECPB156 |
| oHCT770 | AACTCTTGTTTTCTTCTTTTCTCTAAA (SEQ ID NO: 51) | amplifies genes inserted over NotI site in pBM5155 |
| oHCT771 | GGGACCTAGACTTCAGGTTGTC (SEQ ID NO: 52) | amplifies genes inserted over NotI site in pBM5155 |

Directed Evolution

Directed evolution was initiated by growing parent strains overnight in liquid YPD medium (1% yeast extract, 2% peptone, 2% glucose). One mL of maltotriose or maltose medium was inoculated with enough overnight culture to give an $OD_{600}$ reading of ~0.1 as measured with an IMPLEN OD600 DiluPhotometer™. Evolution in maltotriose was conducted in synthetic complete (SC) medium (0.17% yeast nitrogen base, 0.5% ammonium sulfate, 0.2% complete drop out mix) with 2% maltotriose and 0.1% glucose. The addition of 0.1% glucose ensured enough growth that mutations could occur and be selected for through the ensuing generations. Directed evolution of yHRVM108 in maltose was carried out in SC with 2% maltose. Because yHRVM108 grew so poorly in maltose alone, an additional 0.1% glucose was supplemented into its medium; after increased growth was observed around generation 110 for replicate A, from which strains yHEB1585-1587 are derived, and around generation 80 for replicate B, from which strains yHEB1588-90 were derived, subsequent generations of yHRVM108 directed evolution in maltose for these replicates was conducted with 2% maltose only. The directed evolution of each strain was carried out in triplicate. Samples were grown on a culture wheel at room temperature (22° C.) and diluted 1:10 into fresh media every 3-4 days. Samples of each evolution replicate were taken every other passage and placed into long-term storage by mixing 700 uL of culture with 300 uL of 50% glycerol in a cryotube and storing it at −80° C. The number of doublings between passages was estimated from cell counts during the second and third passages. Evolution was carried out for a total of 100 passages. Strains that could not use the primary carbon source in adaptive evolution medium underwent approximately one cell division per day on average.

Sporulation and Backcrossing

To induce sporulation, strains were grown to saturation, washed twice, and then resuspended in 200 μL liquid sporulation (spo) medium (1% potassium acetate, 0.5% zinc acetate). 30 µL of this suspension was added to 1.5 mL of spo medium and incubated on a culture wheel at room temperature. Cultures were checked for sporulation after 2-5 days. Tetrads were dissected using a Singer SporePlay. For backcrossing, tetrads of the strains to be crossed were dissected on a single YPD plate. A spore from one parent was placed in close proximity to a spore from the other parent; they were observed over several hours for mating and zygote formation. Transformations of the diploid $F_1$ backcross strain for gene knockouts were carried out as described below in the section describing the construction of gene expression plasmids.

Construction of Gene Expression Plasmids

Genes encoding transporters of interest were cloned via gap repair into the NotI site of plasmid pBM5155 (GenBank KT725394.1), which contains the complete machinery necessary for doxycycline induction of genes cloned into this site (Alexander et al. 2016). Transformation was carried out using standard lithium acetate transformation (Daniel Gietz and Woods 2002) with modifications to optimize transformation in *S. eubayanus*. Specifically, transformation reactions were heat shocked at 34° C. After 55 minutes, 100% ethanol was added to 10% total volume, and the reactions heat shocked for another 5 minutes before they were allowed to recover overnight and plated to selective media the next day. When necessary, plasmids were recovered and amplified in *Escherichia coli* for transformation into multiple strains. The sequences of genes encoding transporters cloned into pBM5155 were verified by Sanger sequencing. *S. eubayanus* MALT1, MALT3, and MALT4 were amplified from FM1318, lgAGT1 was amplified from yHAB47, and ncAGT1 was amplified from yHRVM108. Primers used for plasmid construction and sequence verification are listed in Table 2.

Growth Assays

Growth was measured in liquid media in 96-well plates using $OD_{600}$ measurements on a FLUOstar Omega microplate reader. To test the abilities of single-colony isolates of yHKS210 evolved in maltotriose to grow in maltotriose, strains were grown overnight in liquid YPD and washed. Yeast was inoculated into wells to give an initial $OD_{600}$ reading of ~0.1-0.2. To test the ability of single-colony isolates of yHRVM108 evolved in maltose to use maltose and maltotriose, a single colony was used to inoculate both SC+2% maltose and SC+2% maltotriose media. For assays testing the growth of strains carrying MALT genes expressed on an inducible plasmid, strains were grown to saturation, washed twice, resuspended in liquid SC without added carbon, and starved for 24 hours. The next day, strains were diluted in SC without added carbon to $OD_{600}$=1.9+/−0.05 to ensure that all cultures had approximately the same starting concentration. 15 µL of each diluted culture was added to 235 µL of the test medium. Three technical replicates, randomly distributed on a 96-well plate to control for position effects, were carried out for each strain. Strains were tested in SC with 2% added carbon source and 50 ng/mL doxycycline to induce plasmid gene expression. To control for growth from the small amount of non-maltotriose sugar in 98% pure maltotriose, the parent strains of yHRVM108 and yHKS210 were also tested in SC medium+0.04% glucose, reflecting the approximate amount of other carbon sources expected in SC medium+2% maltotriose.

Bulk-Segregant Analysis

As described above, 60 spores from 15 fully viable tetrads of strain yHEB1593 (F1 of yHKS210×yHEB1505) were dissected and individually screened for their ability to grow in SC+2% maltotriose. F2 segregants that could grow in maltotriose were classified as MalTri$^+$, and those that could not were classified as MalTri$^-$. Each F2 segregant was then individually grown to saturation in liquid YPD. The saturated cultures were spun down, the supernatant removed, and enough cells resuspended in liquid SC medium to give an $OD_{600}$ measurement of between 1.9 and 1.95. Strains were pooled based on their ability to grow in maltotriose, leading to a MalTri$^+$ pool and a MalTri$^-$ pool. To pool, 1 mL of each strain dilution was added to the appropriate pool of cells and vortexed to mix. A phenol-chloroform extraction was used to isolate gDNA from the segregant pools. The gDNA was sonicated and ligated to Illumina TruSeq-style dual adapters and index sequencing primers using the NEBNext® DNA Library Prep Master Mix Set for Illumina® kit following the manufacturer's instructions. The paired-end libraries were sequenced on an Illumina MiSeq instrument, conducting a 2×250 bp run.

Analysis of Bulk-Segregant Whole-Genome Sequencing Reads

To identify fixed differences between the meiotic segregant pools, whole-genome assemblies were made for the MalTri$^-$ group of segregants using the meta-assembler iWGS with default settings (Zhou et al. 2016). The final de novo genome assembly of the MalTri$^-$ pool was made by DISCOVAR (Weisenfeld et al. 2014) in iWGS. This assembly was used for reference-based genome assembly and variant calling using reads from the MalTri$^+$ pool following the protocol described in Peris and Langdon et al. 2016. Assemblies of the putative chimeric maltotriose transporter were retrieved from the MalTri$^+$ pool of reads using the program HybPiper (Johnson et al. 2016). Briefly, HybPiper uses a BLAST search of read sequences to find reads that map to a query sequence; it then uses the programs Exonerate (Slater and Birney 2005) and SPAdes (Bankevich et al. 2012) to assemble the reads into contigs. The sequence and genomic location of the chimeric transporter was further verified by PCR amplification and Sanger sequencing (Table 2).

Phylogenetic and Protein Mutation Prediction Analyses

Figure 2:
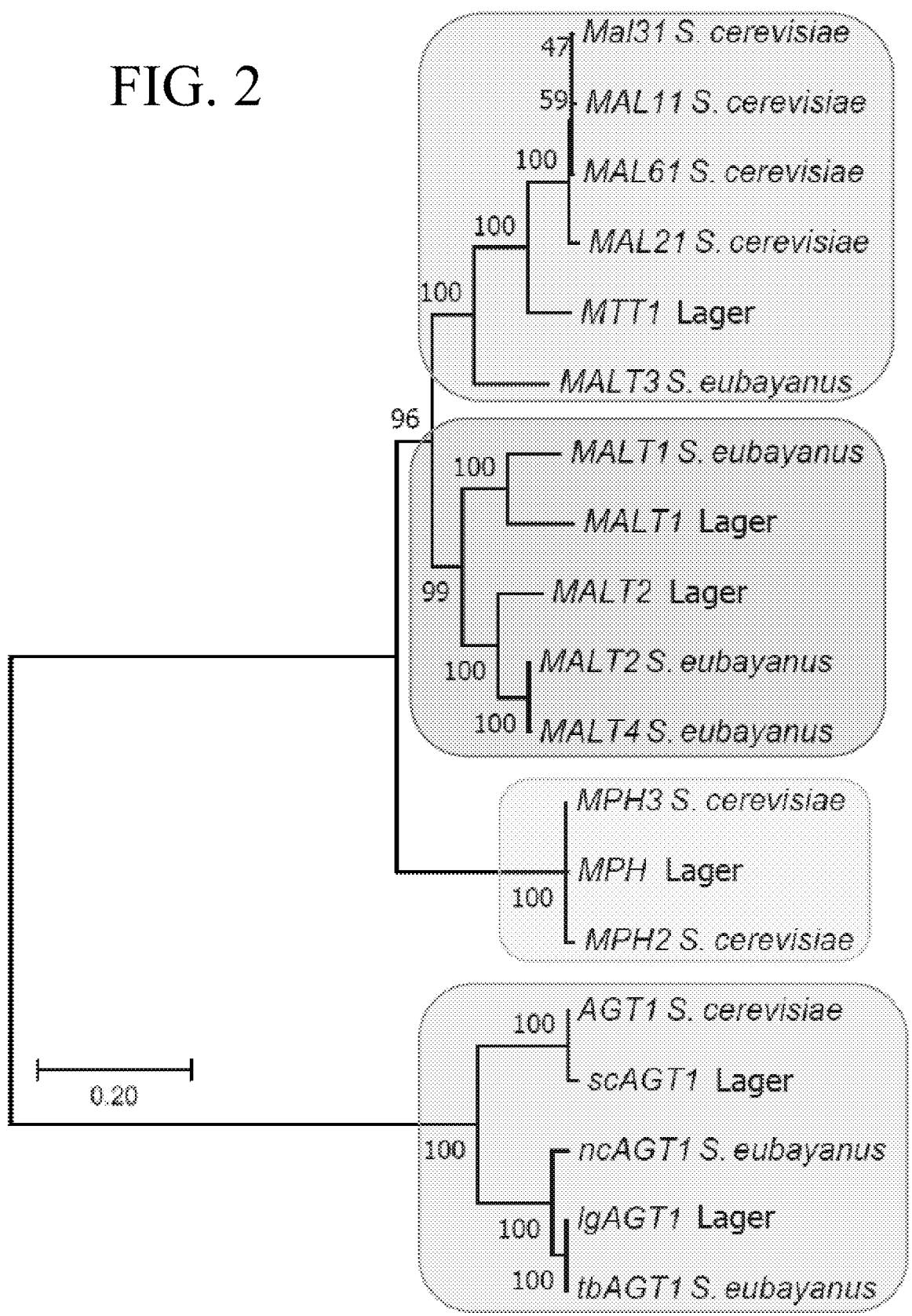
FIG. 2 shows a ML phylogenetic tree of MALT genes described in *S. cerevisiae, S. eubayanus*, and lager-brewing hybrids. The scale bar equals the number of nucleotide substitutions per site.

Multiple sequence alignments between the proteins encoded by the MALT genes were carried out using MUSCLE (Edgar 2004), as implemented in Geneious v.9.0.3 http://www.geneious.com, Kearse et al., 2012). Phylogenetic relationships were determined using codon alignments. Codon alignments were made using PAL2NAL (Suyama, Torrents, & Bork, 2006; http://www.bork.embl.de/pal2nal/) to convert the MUSCLE alignments of amino acid sequences to nucleotide alignments. A phylogenetic tree of nineteen MALT genes from *S. eubayanus*, *S. cerevisiae*, and lager-brewing yeasts was made as described in Baker et al. 2015 using MEGA v.6. All genes used in the phylogenetic analysis are as follows. MAL21, MAL31, and MAL61 from *S. cerevisiae*; MALT1 and MALT3 from *S. eubayanus*; MALT1, MALT2 and MPH from lager-brewing yeast; MPH2 and MPH3 from *S. cerevisiae*; AGT1 (MAL11 in Baker et al. 2015) from *S. cerevisiae*; scAGT1 (Weihen-MAL11-CB in Baker et al. 2015); and lgAGT1 (Weihen-MAL11-CA in Baker et al. 2015) were retrieved as previously described in Baker et al. 2015. Sequences for MALT2 and MALT4 were retrieved from the genome assembly of CBS12357 from Okuno et al. 2016. MALT11 was retrieved from the genome assembly of *S. cerevisiae* strain YJM456 (Strope et al. 2015). Sequences for tbAGT1 and ncAGT1 were retrieved as described above. MALT11 and AGT1 are both α-glucoside transporters located at the *MAL1* locus in *S. cerevisiae* and as such are considered alleles of each other (Charron and Michels 1988; Han et al. 1995). Their shared genomic location notwithstanding, MALT11 and AGT1 are not phylogenetically closely related, with MAL11 clustering with other MALx1 type transporters (FIG. 2). In addition, while AGT1 can support maltotriose transport, MAL11, like other MALx1 genes, cannot (Han et al. 1995; Brown et al. 2010). Despite their dissimilarity, AGT1 is recorded in the *Saccharomyces* Genome Database as MAL11 since the reference strain carries the AGT1 allele at the MAL1 locus (Vidgren et al. 2005, 2009). For this reason MAL11 is often used to refer to AGT1 (Brown et al. 2010; Baker et al. 2015; Brickwedde et al. 2017). For clarity, here we use MAL11 to only refer to the MALx1 like allele and AGT1 to the distinct maltotriose transporting allele.

Protein structure predictions for MALT3, MALT4, lgAGT1, and scAGT1 were carried out using the I-TASSER server, and the structure prediction of MALT434 was carried out using the command line version of I-TASSER (https://zhanglab.ccmb.med.umich.edu/I-TASSER/,Roy, Kucukural, & Zhang, 2010; Yang et al., 2015; Zhang, 2008). The potential impact of the single residue difference between lgAGT1 and tbAGT1 was analyzed by two different methods. Prediction of the change in free energy ($\Delta\Delta G$) was carried out using the STRUM server (Quan et al. 2016). A $\Delta\Delta G$ score of $<+/-0.5$ was considered to be unlikely to affect function (Bromberg and Rost 2009). Homology-based predictions were made using SIFT (Ng and Henikoff 2001a, 2002, 2003, 2006; Kumar et al. 2009). The SIFT Related Sequences analysis was done using the amino acid sequences of MALT genes in the phylogenetic analysis above. Several SIFT analyses were also carried out using the SIFT Sequence analysis program. This analysis operates using the same principle as the SIFT Related Sequences analysis, but rather than being supplied by the user, homologous sequences were provided by a PSI-BLAST search of the indicated protein database. The SIFT Sequence analyses were carried out using default settings and the following databases NCBI nonredundant 2011 March, 2UniRef90 2011 April, 3UniProt-SwissProt 57.15 2011 April
Results
Maltotriose Transporters in *S. eubayanus*

Previously, we identified four genes in the *S. eubayanus* genome assembly with homology to genes encoding known maltose transporters (MALT genes) (Baker et al. 2015). The complete sequence of one transporter, MALT4, was not present in the Baker et al. assembly but was found in another assembly for the type strain of *S. eubayanus* (Okuno et al. 2016). MALT4 encodes an identical amino acid sequence to MALT2, and these genes are likely related by a recent subtelomeric duplication and/or translocation event (see Material and Methods). Because of their identical amino acid sequences, we refer to these genes jointly as MALT2/4. To determine if they could enable maltotriose transport, MALT1, MALT3, and MALT2/4 were individually overexpressed using an inducible promoter in the *S. eubayanus* strain yHRVM108, a strain of *S. eubayanus* isolated from North Carolina that is unable to grow on maltotriose and, unlike other strains of *S. eubayanus*, has sluggish growth on maltose. None of these genes were able to confer growth on maltotriose when overexpressed (Table 3).

TABLE 3

| Strain | Background | Transporter | Initial OD | Day 3 | Day 6 |
|---|---|---|---|---|---|
| yHRVM108* | North Carolinian strain | — | 0.16 (+/−0.05) | 0.39 (+/−0.02) | 0.48 (+/−0.01) |
| yHRVM108 | North Carolinian strain | — | 0.12 (+/−0.03) | 0.47 (+/−0.00) | 0.46 (+/−0.03) |
| yHEB1870 | yHRVM108 | MALT1 | 0.13 (+/−0.03) | 0.43 (+/−0.04) | 0.58 (+/−0.04) |
| yHEB1877 | yHRVM108 | MALT2/4 | 0.11 (+/−0.00) | 0.39 (+/−0.01) | 0.57 (+/−0.02) |
| yHEB1872 | yHRVM108 | MALT3 | 0.13 (+/−0.01) | 0.41 (+/−0.00) | 0.62 (+/−0.5) |
| yHEB1883 | yHRVM108 | ncAGT1 | 0.11 (+/−0.01) | 0.54 (+/−0.07) | 1.34 (+/−0.10) |
| yHEB1884 | yHRVM108 | lgAGT1 | 0.10 (+/−0.00) | 0.42 (+/−0.07) | 0.94 (+/−0.09) |

Growth on SC + 2% maltotriose (98% pure) of strains expressing MALT genes on a doxycycline-inducible plasmid. N = 3, standard deviation in parentheses.
*Control grown in SC + 0.04% glucose + doxycycline to reflect the approximate amount of growth expected from contamination with other carbon sources when using 98% pure maltotriose.

Although none of the transporters found in the type strain of *S. eubayanus* were able to support growth on maltotriose, there is compelling evidence from lager-brewing yeasts for the existence of maltotriose transporters within the greater *S. eubayanus* population (Dietvorst et al. 2005; Nakao et al. 2009; Vidgren et al. 2010; Cousseau et al. 2013; Baker et al. 2015). Of particular interest are the alleles of AGT1. Two versions of AGT1 are present in the genomes of lager-brewing yeasts. One, which we call scAGT1 (*S. cerevisiae*-AGT1), was donated by the *S. cerevisiae* parent of lager yeasts but is probably non-functional due to a nonsense mutation early in its sequence (Vidgren et al. 2005; Nakao et al. 2009; Magalhães et al. 2016). The other AGT1, which we call lgAGT1 (lager-AGT1), was proposed to be of *S. eubayanus* origin based on its sequence divergence from scAGT1 and its location near *S. eubayanus* genomic regions (Nakao et al. 2009). Both lgAGT1 and scAGT1, like other AGT1 alleles (Han et al. 1995; Day et al. 2002b; Vidgren et al. 2005), can transport both maltose and maltotriose (Dietvorst et al. 2005; Vidgren et al. 2009; Vidgren and Londesborough 2012; Cousseau et al. 2013). Thus far, full-length sequences closely related to this lgAGT1 have not been described in any strain of *S. eubayanus*, but contigs containing the partial sequence of a gene with high similarity to lgAGT1 were recovered from an assembly of the genome of CDFM21L.1, a Tibetan isolate of *S. eubayanus* (Hebly et al. 2015).

To recover a full-length sequence of lgAGT1 from *S. eubayanus* genome sequence, the nucleotide sequence of lgAGT1 was used as query sequence in an SRA-BLAST against Illumina reads deposited in NCBI for CDFM21L.1 (Bing et al. 2014) and the closely related strain yHRVM108 (Peris and Langdon et al. 2016). Both CDFM21L.1 and yHRVM108 belong to the Holarctic subpopulation of *S. eubayanus* and are close relatives of the strains of *S. eubayanus* that hybridized with *S. cerevisiae* to form lager-brewing yeasts (Peris and Langdon et al. 2016). From the reads that mapped to lgAGT1, two full-length genes with high sequence identity to lgAGT1 were assembled and designated tbAGT1 and ncAGT1, for Tibetan-AGT1 and North Carolinian-AGT1, respectively (FIGS. 1A-1B).

There are two single nucleotide polymorphisms (SNPs) between the full-length sequence of tbAGT1 and lgAGT1, one of which results in a non-synonymous substitution (FIG. 1B). This single-residue change probably has no impact on the function of tbAGT1 compared to lgAGT1 since it occurs near the N-terminus and outside of any predicted transmembrane domains (FIG. 51). In addition, analyses of the predicted effect of this substitution in lgAGT1 using STRUM and SIFT mutant protein prediction software (Ng and Henikoff 2001b; Quan et al. 2016) suggest that this single substitution is unlikely to significantly impact the structure or function of the protein (Table 4).

TABLE 4

| STRUM[a] | Related Sequences[c] | SIFT[b] NCBI[1] | Sequence[d] UniRef90[2] | SwissProt[3] |
|---|---|---|---|---|
| −0.4 | 1.00 | 1.00 | 0.57 | 1.00 |
| # of sequences analyzed | 19 | 59 | 18 | 8 |

Results of mutation prediction analyses for E18V, the sole non-synonymous substitution in the lgAGT1 protein-coding sequence, relative to tbAGT1.
[a]predicted ΔΔG (<0.5 likely no change in function, Bromberg and Rost 2009)
[b]provides amino acid probablity score (<0.5 predicted to be deleterious)
[c]sequences used for for SIFT analysis are the same as used for the phylogenetic analysis (FIG. 2)
[d]sequences used for analysis provided by a PSI-BLAST of the indicated protein database
Protein Databases:
[1]NCBI nonredundant 2011 Mar,
[2]UniRef90 2011 Apr,
[3]UniProt-SwissProt 57.15 2011 Apr In contrast to tbAGT1, ncAGT1 has 95% sequence identity with lgAGT1, with non-synonymous differences distributed throughout the sequence (FIGS. 1A-1B). Despite the presence of ncAGT1, the yHRVM108 wild type strain grows poorly on maltose and is unable to grow in maltotriose, raising the question of whether the ability to transport maltotriose has been conserved between ncAGT1 and lgAGT1. Interestingly, and in contrast to all MALT genes found in the Patagonian type strain of *S. eubayanus*, overexpression of ncAGT1 in yHRVM108 conferred growth in maltotriose (Table 3), suggesting that insufficient ncAGT1 gene expression, rather than protein function, is likely the main reason for the inability of yHRVM108 to grow on maltotriose.

Phylogenetic Relationship Among Maltose Transporters

Lager-brewing yeasts inherited maltose/maltotriose transporters from both their *S. cerevisiae* and their *S. eubayanus* parents. To put the relationship between *S. eubayanus*, *S. cerevisiae*, and lager transporters into a phylogenetic perspective, a gene tree was constructed for these three groups of MALT genes (FIG. 2). Consistent with previous analyses of MALT genes in *Saccharomyces* (Brown et al. 2010), the current set of MALT genes analyzed fell into 3 major clades. MPH genes, encoding maltose transporters native to *S. cerevisiae* but also present in some lager yeasts (Day et al. 2002a; Vidgren et al. 2005), formed their own small clade. The clade containing the largest number of genes was made up of MALT1-4 from *S. eubayanus*, MALx1 genes from *S. cerevisiae*, and the lager-specific gene MTT1 (Dietvorst et al. 2005; Salema-Oom et al. 2005; Baker et al. 2015). This clade was further subdivided into a group containing only *S. eubayanus* transporter genes and their closely related lager homologs, as well as a second group consisting of MALx1 genes, MTT1, and MALT3.

The final major clade was significantly divergent from the other two groups. This clade consisted of the AGT1 genes and was further split between the AGT1 genes from *S. cerevisiae* and the AGT1 genes from *S. eubayanus*. AGT1 genes isolated from lager yeasts were found in both subclades.

Evolution of Maltotriose Consumption

Since yHRVM108 already contains a functional maltotriose transporter, we decided to see if it could readily evolve maltotriose consumption. We also decided to try to evolve maltotriose utilization in FM1318 (Libkind et al. 2011) and in yHKS210 (Peris et al. 2014), strains that lack transporters capable of conferring maltotriose utilization, even when overexpressed (Table 3). A search of the available genome sequence reads for FM1318 and yHKS210 indicated that neither of these strains contain AGT1 homologs. Since none of these strains can grow on maltotriose, a small amount of glucose was also added to the media to permit a limited number of cell divisions to allow for mutation and selection to occur. Each strain was setup in triplicate and evolved by serial passaging in liquid media. Strains that could not use the primary carbon source in the directed evolution medium underwent approximately one cell division per day on average.

Over the course of 100 passages, representing approximately 3,150 cell divisions in total between all the strains and replicates, only a single replicate evolved the ability to grow in maltotriose. Surprisingly, it was not a replicate of yHRVM108, but one of yHKS210 that evolved maltotriose consumption. Two single-colony isolates (yHEB1505-6) from this replicate were isolated and confirmed to be able to grow on maltotriose without added glucose (FIG. 3A, Table 5).

TABLE 5

| Strain | Background | Evolved in | Initial OD | Day 3 | Day 6 |
|---|---|---|---|---|---|
| yHKS210* | Admixture strain | — | 0.22 (+/−0.01) | 0.68 (+/−0.07) | 0.60 (+/−0.04) |
| yHKS210 | Admixture strain | — | 0.14 (+/−0.02) | 0.41 (+/−0.01) | 0.39 (+/−0.05) |
| yHEB1505 | yHKS210 | maltotriose | 0.16 (+/−0.01) | 1.46 (+/−0.01) | 1.82 (+/−0.03) |
| yHEB1506 | yHKS210 | maltotriose | 0.15 (+/−0.01) | 1.44 (+/−0.02) | 1.76 (+/−0.09) |
| yHRVM108* | North Carolinian strain | — | 0.22 (+/−0.01) | 0.47 (+/−0.01) | 0.48 (+/−0.03) |
| yHRVM108 | North Carolinian strain | — | 0.12 (+/−0.03) | 0.47 (+/−0.00) | 0.46 (+/−0.03) |
| yHEB1585 | yHRVM108 | maltose | 0.12 (+/−0.03) | 0.79 (+/−0.01) | 1.28 (+/−0.06) |
| yHEB1586 | yHRVM108 | maltose | 0.12 (+/−0.03) | 0.81 (+/−0.05) | 1.31 (+/−0.07) |

TABLE 5-continued

| Strain | Background | Evolved in | Initial OD | Day 3 | Day 6 |
|---|---|---|---|---|---|
| yHEB1587 | yHRVM108 | maltose | 0.11 (+/−0.01) | 0.77 (+/−0.01) | 1.32 (+/−0.06) |
| yHEB1588 | yHRVM108 | maltose | 0.13 (+/−0.00) | 0.44 (+/−0.01) | 0.82 (+/−0.10) |
| yHEB1589 | yHRVM108 | maltose | 0.12 (+/−0.01) | 0.56 (+/−0.01) | 0.87 (+/−0.05) |
| yHEB1590 | yHRVM108 | maltose | 0.11 (+/−0.03) | 0.58 (+/−0.01) | 1.00 (+/−0.03) |

Growth on maltotriose of single-colony isolates from adaptive evolution experiments. Strains were evolved with either maltotriose or maltose as the primary carbon source (2%) with 0.1% added glucose. N = 3.
*Control grown in SC + 0.04% glucose to reflect the approximate amount of growth expected from contamination with other carbon sources when using 98% pure maltotriose.

Figures 3E, 3F:
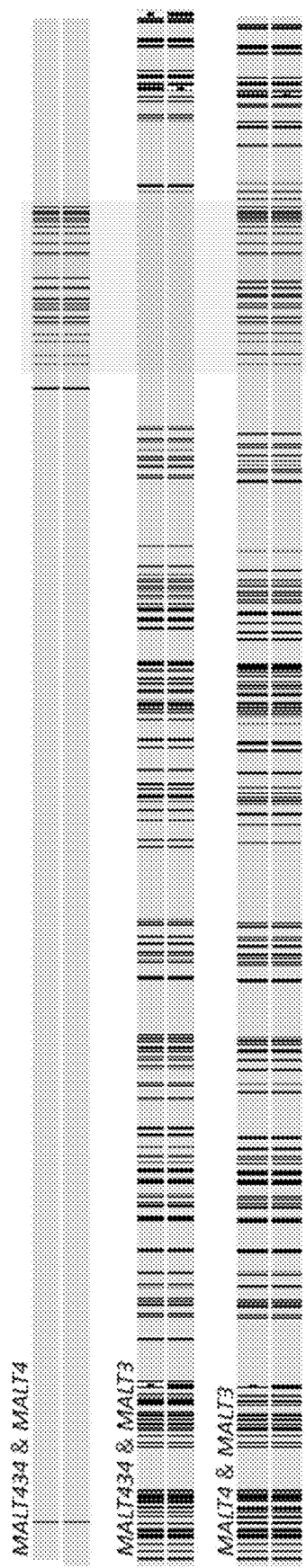
FIG. 3E is a table of initial and day-three OD600 (OD) readings of yHKS210, yHEB1505, yHEB1593, yHEB1853, and yHEB1854 on SC+2% maltotriose as the sole carbon source. N=3, standard deviation in parentheses. The control was grown in SC+0.04% glucose to reflect the approximate amount of growth expected from contamination with other carbon sources when using 98% pure maltotriose.
FIG. 3F shows pairwise alignments between MALT3, MALT4, and MALT434. The highlighted region indicates the sequence that was exchanged in MALT4. MALT3 and MALT4 sequences are from strain FM1318, while MALT434 sequences are from strain yHEB1505, an evolved MalTri+ descendent of yHKS210; differences outside of the chimeric region existed in the yHKS210 parent strain.

To determine the genetic architecture of maltotriose utilization, we setup an $F_1$ backcross between yHEB1505 and the parent strain (yHKS210), producing strain yHEB1593, a putative heterozygote capable of growth on maltotriose (FIGS. 3B and 3E). In a test of 15 fully viable tetrads, maltotriose utilization segregated in a perfect 2:2 manner (FIG. 3C). These results suggest that the ability of the evolved strain to use maltotriose was conferred by a dominant mutation at a single genetic locus. We performed bulk-segregant analysis (Brauer et al. 2006; Segrè et al. 2006; Ehrenreich et al. 2010) using strains derived from the F2 spores, dividing them between those that could (MalTri$^+$) and those that could not (MalTri$^-$) use maltotriose (FIG. 3C), with a total of 30 strains in each category. Twelve 1-kb regions were identified as containing fixed differences between the MalTri$^+$ and MalTri$^-$ strains. Of these regions, eight mapped to genes encoding ribosomal proteins and most likely represent assembly artefacts due to the presence of many closely related paralogs. Three other regions contained fixed changes between the MalTri$^+$ and MalTri$^-$ groups but had no clear relationship to carbon metabolism. The final 1-kb region mapped to the MALT4 locus of FM1318. The coding sequence of MALT4 from the MalTri$^+$ group contained 54 SNPs relative to the MALT4 allele found in FM1318. Four of these SNPs were synonymous differences that were present in yHKS210 before the start of directed evolution. The remaining 50 SNPs occurred within a single 230-bp region. Of these, 11 were predicted to lead to non-synonymous changes (FIGS. 3F and 3H). Closer inspection revealed that the changes within the 230-bp region were the result of a recombination event between MALT4 and MALT3, creating a chimeric gene (FIGS. 3F-H), likely through ectopic gene conversion. We call this chimeric MALT4 gene MALT434 after the arrangement of sequences from its parent genes. The sequence of MALT3 was not impacted by this mutation event.

Figures 5A, 5B, 5C:
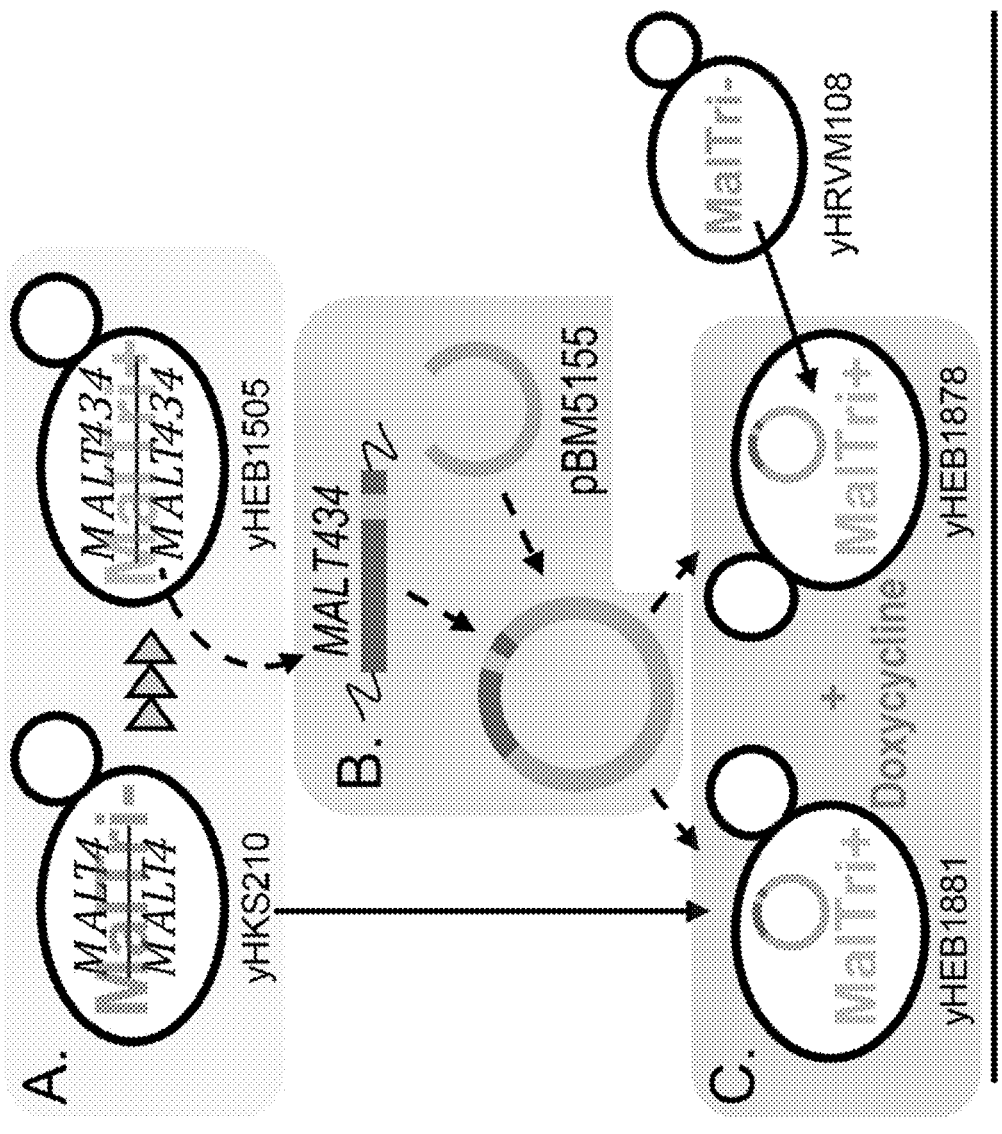
FIG. 5A is a schematic of the directed evolution of non-maltotriose utilizing strain (MalTri−), yHKS210, to maltotriose utilizing (MalTri+) strain, yHEB1505, by serial passing on maltotriose containing media (same as FIG. 3A).
FIG. 5B is a schematic of the insertion of MALT434 into vector pBM5155 for doxycycline-inducible heterologous expression in MalTri− strains.
FIG. 5C is a schematic of the transformation of MALT434 expression plasmid in MalTri− *S. eubayanus* strains yHKS210 and yHRVM108.

To confirm that MALT434 was the causative locus of maltotriose utilization, we replaced MALT434 with the NatMX marker in the heterozygous F1backcross strain (FIG. 3D), leaving only the original non-chimeric MALT4 gene. This knockout eliminated that strain's ability to utilize maltotriose (FIG. 3E), demonstrating that MALT434 is required for maltotriose utilization. Conversely, replacing the parental, non-chimeric allele of MALT4 in the heterozygous $F_1$ backcross strain had no impact on maltotriose utilization. Furthermore, overexpression of MALT434 in both the unevolved parent, yHKS210, and in the yHRVM108 background (FIG. 5) supported growth in maltotriose, demonstrating that its overexpression is sufficient to confer maltotriose utilization (Table 3). These results confirm that the mutant MALT434 gene encodes a functional maltotriose transporter.

Figure 4:
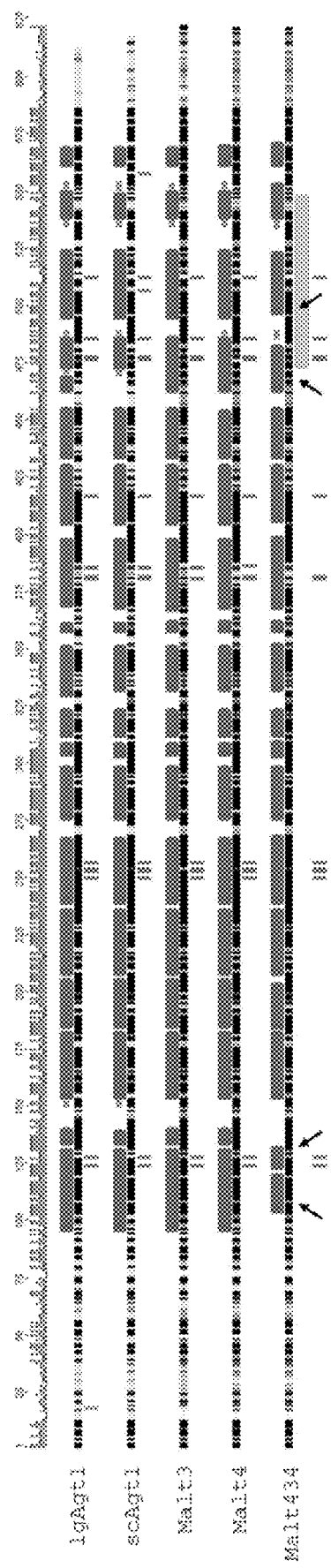
FIG. 4 shows a protein structural alignment between Malt3, Malt4, Malt434, scAgt1, and lgAgt1. The purple blocks represent predicted alpha helices, and the orange lines represent predicted beta strands. Red ticks mark predicted maltose binding sites. Blue ticks mark residues found to be important for maltotriose transport by Smit et al. 2008. Green ticks mark the location of the single non-synonymous substitution between lgAGT1 and tbAGT1. Arrows point to alpha helices in Malt434, whose predicted sizes are reduced compared to other transporters in the alignment.

It was surprising that a sequence from MALT3 permitted MALT4 to now encode a maltotriose transporter because neither MALT3 nor MALT4 supported maltotriose utilization on their own (Table 3). Malt3 and Malt4 share about 80% amino acid identity overall and 85% amino acid identity in the chimeric region specifically (FIG. 3H). Most residues in the chimeric region had high similarity between Malt3 and Malt4, as measured by Blosum62 similarity matrix (FIG. 3I) (Henikoff and Henikoff 1992), but there were a handful of low similarity amino acids as well. To gain insight into what changes may be driving the new functionality of MALT434, we used I-TASSER (Zhang 2008; Roy et al. 2010; Yang et al. 2015) to predict the protein structure of Malt3, Malt4, and Malt434. I-TASSER predicts a proteins' structure based on its homology to proteins whose structures have already been solved. I-TASSER determined that Malt3, Malt4, and Malt434 all had homology with members of the Major Facilitator Superfamily (MFS) of transporters, consistent with other studies on the structure of maltose transporters in Saccharomyces (Cheng and Michels 1989; Han et al. 1995; Barrett et al. 1999; Yan 2015). Based on these protein structure predictions, the structure of the chimeric region is likely conserved between Malt3 and Malt4. I-TASSER predicted that the chimeric region encompasses one full transmembrane domain and parts of two other transmembrane domains (FIG. 3J). I-TASSER also predicted that this region contains four maltose-binding sites. These same domains and predicted binding residues were identified within Malt434 as well. Interestingly, I-TASSER predicted that two of the alpha helices in the chimeric region were shorter in Malt434 than in the parent proteins. Towards the N-terminal end of the protein, another two alpha helices were also predicted to be shortened in Malt434 relative to its parents (FIG. 4). The regions covered by these alpha helices were otherwise predicted to be conserved between both Malt3 and Malt4, as well as the phylogenetically more distant maltotriose transporters lgAgt1 and scAgt1 (FIG. 3J, FIG. 4). Slightly decreasing the amount of structure in the protein by shortening these key alpha helices could have increased the overall flexibility of the protein, potentially making it easier to accommodate maltotriose, which contains an extra glucose moiety relative to maltose.

Figure 6:
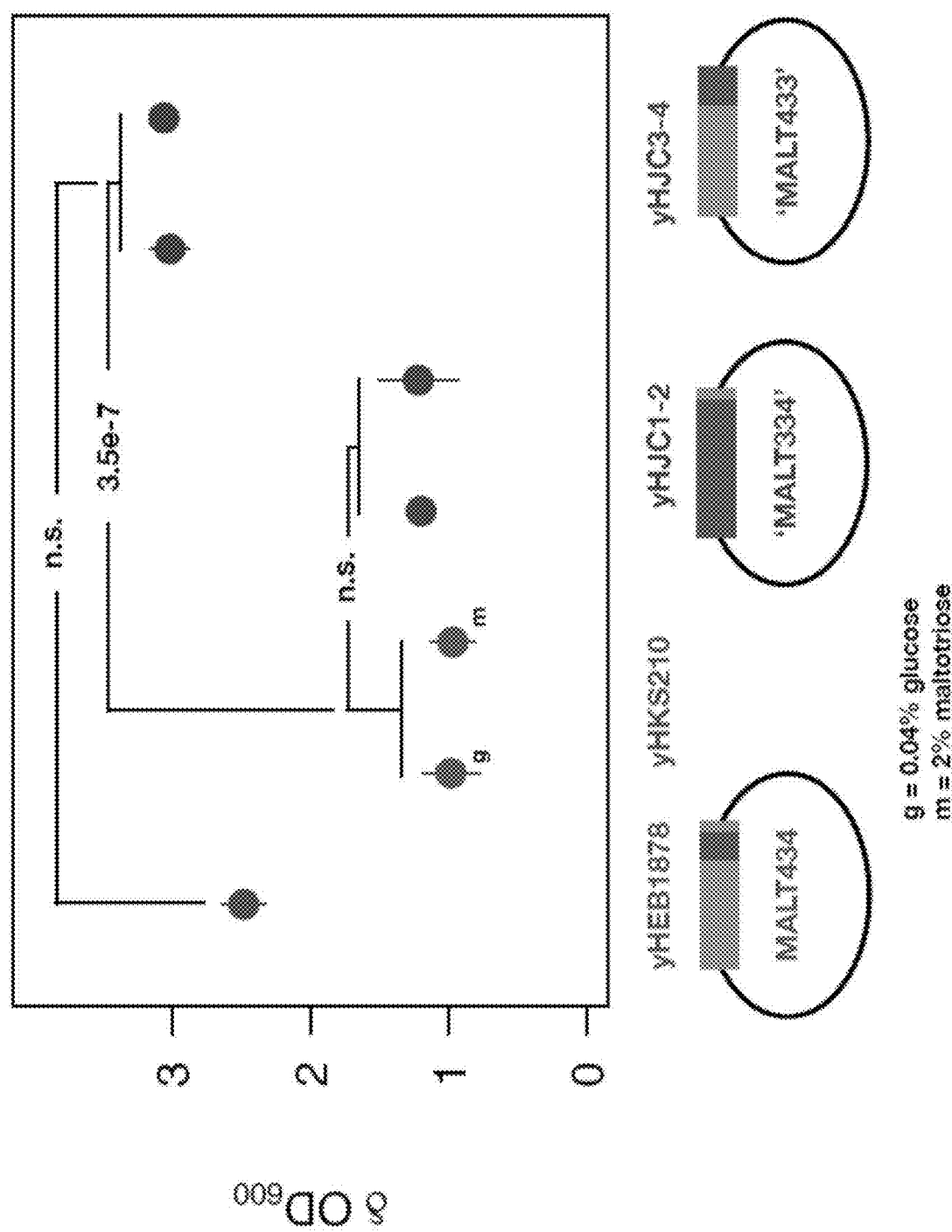
FIG. 6 is a graph showing growth of the chimeric MALT constructs the change in OD 600 over 7 days of growth of *S. eubayanus* strains expressing MALT434 (yHEB1878), MALT334 (yHJC1-2), or MALT433 (yHJC3-4) from an inducible vector in 2% maltotriose medium, compared to *S. eubayanus* lacking heterologous transporter expression (yHKS210) grown in 2% maltotriose and 0.04% glucose. Points and bars show the mean+/−standard error of three technical replicates randomly distributed on a 96-well plate. p-values from two-sided t test.

In a further attempt to define the portion of MALT434 that is critical for growth on maltotriose, we tested a further set of strains expressing MALT434 (yHEB1878), MALT334 (yHJC1-2) and MALT 433 (yHJC3-4). The results are shown in FIG. 6. Strain yHKS210 served as the wild-type control which was unable to grow on maltotrise. These strains allow a direct comparison between the MALT434 which confers maltotriose transport and allows for growth on maltotriose with the related chimeric proteins all having the same region from MALT 3 that MALT 434 has. The MALT334 strain was not capable of growing on or utilizing maltotriose any better than the wild-type strain, whereas the MALT433 strain was capable of utilizing maltotriose similar to MALT434. Thus the N-terminal portion of MALT4 seems necessary for maltotriose utilization. The C-terminus can be derived from either parent polypeptide.

Discussion

A Chimeric Path to Novel Substrate Utilization

We found that a chimeric protein constituted a novel maltotriose transporter, despite the fact that neither of the parent proteins was able to transport maltotriose. Since the MALT3 region recombined into MALT4 was not able to support maltotriose in its native background, epistatic interactions with other sequence(s) in MALT4 must be important for this gain of function. Comparison of predicted protein structures suggested that several alpha helices may be shortened in Malt434 compared to the parent proteins. The regions covered by these helices were otherwise predicted to be conserved, even out to the distantly related Malt transporters lgAgt1 and scAgt1 (FIG. 2, FIG. 3J, FIG. 4). The predicted shortening of some alpha helices within the chimeric protein compared to both its parents suggests that recombining the MALT3 region into MALT4 may have decreased the overall rigidity of the encoded chimeric protein, allowing it to accommodate bulkier substrates, such as maltotriose.

A previous study characterizing residues important for transporting maltotriose in scAgt1 found two residues that were important for its ability to transport maltotriose, while not affecting its ability to transport maltose (Smit et al. 2008). One of these residues lies within the chimeric region we observed in Malt434, and the other is 10 amino acid residues downstream (FIG. 3J). As the overall structure of maltose/maltotriose transporters is conserved (Cheng and Michels 1989; Han et al. 1995; Barrett et al. 1999; Yan 2015), the area in and around the chimeric region in Malt434 may itself be important for substrate specificity.

Replacement of the MALT4 sequence in this region with sequence from MALT3 may then have facilitated maltotriose transport in two ways. First, the mutation may have increased the overall flexibility of the encoded transporter, allowing it to accommodate the larger maltotriose molecule. Second, it could also have specifically altered an important substrate interface for better interaction with maltotriose, possibly by also making this region more flexible. Testing these biophysical and structural models will require future experiments, such as solving the crystal structures for Malt3, Malt4, and Malt434 as complexes with maltose and/or maltotriose.

Challenges of Evolving Maltotriose Utilization

Based on the results of our directed evolution experiments, which led to a single novel maltotriose transporter, the evolution of a protein that can transport maltotriose seems to be relatively rare, much rarer than one would expect if it could have been achieved with a single point mutation. The drastic mutation required to convert MALT4 into a gene encoding a maltotriose transporter and the phylogenetic placement of the rare known maltotriose transporters suggest that maltotriose transporters are generally difficult to evolve. Of the known MALT genes, only MTT1 and the AGT1 clade encode maltotriose transporters (Han et al. 1995; Dietvorst et al. 2005; Salema-Oom et al. 2005; Vidgren and Londesborough 2012). Other MALT genes described in S. eubayanus were not found to be able to encode maltotriose transporters (Table 3), and no MALx1-type genes are known to encode maltotriose transporters (Horák 2013). MAL11 is sometimes described as being able to transport maltotriose (Brown et al. 2010; Baker et al. 2015; Brickwedde et al. 2017), but this discrepancy is the result of confusion over the naming of AGT1 in S288C and has been noted before (see Materials and Methods and Vidgren et al. 2005, 2009).

But what of the evolution of expression of a maltotriose transporter that was already present? Initially, we anticipated that it would be simple for yHRVM108 to evolve the ability to utilize maltotriose because we knew it already contained a transporter whose expression allows for strong maltotriose utilization in the parent background (Table 3). However, over the course of 100 passages, representing around 1,050 generations in yHRVM108, no maltotriose-utilizing lineage of yHRVM108 arose. While evolving yHRVM108 under our maltotriose selection regime was not successful, we were surprised to find an alternative and indirect selection regime could evolve maltotriose utilization in this background. When we began directed evolution of S. eubayanus to maltotriose, we also started another directed evolution experiment to try and improve yHRVM108's sluggish growth in maltose. Here, all three replicates of yHRVM108 eventually evolved the ability to grow rapidly on maltose. On average, single-colony isolates from these replicates grew four times as fast as the unevolved parent over two days in maltose (Table 6). Interestingly, isolates from the first two replicates that gained the ability to grow on maltose also gained the ability to utilize maltotriose (Table 5), despite never being exposed to maltotriose during the course of directed evolution.

TABLE 6

| Strain | Background | Evolved in | Initial OD | Day 2 |
|---|---|---|---|---|
| yHRVM108* | North Carolinian strain | — | 0.22 (+/−0.01) | 0.43 (+/−0.00) |
| yHRVM108 | North Carolinian strain | — | 0.15 (+/−0.03) | 0.37 (+/−0.02) |
| yHEB1585 | yHRVM108 | maltose | 0.16 (+/−0.02) | 1.49 (+/−0.01) |
| yHEB1586 | yHRVM108 | maltose | 0.14 (+/−0.01) | 1.48 (+/−0.01) |
| yHEB1587 | yHRVM108 | maltose | 0.16 (+/−0.01) | 1.49 (+/−0.02) |
| yHEB1588 | yHRVM108 | maltose | 0.17 (+/−0.01) | 1.40 (+/−0.01) |
| yHEB1589 | yHRVM108 | maltose | 0.18 (+/−0.01) | 1.46 (+/−0.03) |
| yHEB1590 | yHRVM108 | maltose | 0.18 (+/−0.01) | 1.43 (+/−0.04) |

Growth on maltose of single-colony isolates. Isolated from adaptive evolution of yHRVM108 on 2% maltose + 0.1% glucose. N = 3.
*Control grown in SC + 0.04% glucose to reflect the approximate amount of growth expected from contamination with other carbon sources when using 98% pure maltotriose.

The fact that maltotriose consumption independently evolved at least twice under directed evolution for maltose utilization suggests that our maltotriose selection regime itself may have played a role in restraining evolution. In other experiments to evolve Saccharomyces yeasts to carbon limitation or maltotriose consumption, the parent strains already had some capacity to use the supplied carbon source (Dunham et al. 2002; Brickwedde et al. 2017). For our experiments, this was true for directed evolution for maltose utilization, but it was not the case for directed evolution for maltotriose utilization.

Upregulation of MAL genes first requires maltose (or presumably maltotriose) to enter the cell (Wang et al. 2002). In the absence of glucose, at least one of the MALT transporters is ostensibly expressed at some level to allow this to occur (Wang et al. 2002). As yHRVM108 is unable to grow in maltotriose (Table 5), it seems unlikely that appreciable ncAGT1 is expressed. Nonetheless, under the maltose evolution conditions, cells started with some limited capacity to take up maltose, presumably from another MALT that was expressed, and thereby likely induced expression of MAL genes. Any regulatory mutations that loosened negative regulation or enhanced induction of ncAGT1 and other MALT genes in the absence of glucose and the presence of maltose would have been favored by selection (Horák 2013). As a result, relatively simple changes may have been sufficient to allow for ncAGT1 expression during evolution in maltose. Such changes would have been selected for since expression of ncAGT1 could help increase maltose uptake.

However, during evolution in maltotriose, the MAL genes would have remained repressed since no maltose was present in the culture medium. As a consequence, rarer (and never observed) mutations might have been necessary to achieve expression of ncAGT1 in maltotriose. In retrospect, what appeared to be a simple request, to turn on the ncAGT1 gene in the condition being selected for, may in fact have been quite difficult by simple mutations, whereas our indirect selection regime on maltose proved more effective.

REFERENCES

Alexander W. G., Peris D., Pfannenstiel B. T., Opulente D. A., Kuang M., et al., 2016 Efficient engineering of marker-free synthetic allotetraploids of *Saccharomyces*. Fungal Genet. Biol. 89: 10-17.

Altschul S., Madden T. L., Schïffer A. A., Zhang J., Zhang Z., et al., 1997 Gapped BLAST and PSI-BLAST: a new generation of protein database search programs. Nucleic Acids Res. 25: 3389-3402.

Baker E., Wang B., Bellora N., Peris D., Hulfachor A. B., et al., 2015 The Genome Sequence of *Saccharomyces eubayanus* and the Domestication of Lager-Brewing Yeasts. Mol. Biol. Evol. 32: 2818-2831.

Bankevich A., Nurk S., Antipov D., Gurevich A. A., Dvorkin M., et al., 2012 SPAdes: A New Genome Assembly Algorithm and Its Applications to Single-Cell Sequencing. J. Comput. Biol. 19: 455-477.

Barnett J. A., 1992 Some controls on oligosaccharide utilization by yeasts: The physiological basis of the *Kluyver* effect. FEMS Microbiol. Lett. 100: 371-378.

Barrett M. P., Walmsleyt A. R., Gould G. W., 1999 Structure and function of facultative sugar transporters. Curr. Opin. Cell Biol. 11: 496-502.

Bing J., Han P.-J., Liu W.-Q., Wang Q.-M., Bai F.-Y., 2014 Evidence for a Far East Asian origin of lager beer yeast. Curr. Biol. 24: R380-1.

Brauer M. J., Christianson C. M., Pai D. A., Dunham M. J., 2006 Mapping novel traits by array-assisted bulk segregant analysis in *Saccharomyces cerevisiae*. Genetics 173: 1813-6.

Brickwedde A., Broek M. van den, Geertman J.-M. A., Magalhães F., Kuijpers N. G. A., et al., 2017 Evolutionary Engineering in Chemostat Cultures for Improved Maltotriose Fermentation Kinetics inSaccharomyces pastorianusLager Brewing Yeast. Front. Microbiol. 8: 1690.

Briggs D. E., Brookes P. A., Stevens R. B. C. A., 2004 *Brewing: science and practice*. Woodhead Publishing Limited, Abington Hall, Abington Cambridge CB1 6AH, England.

Bromberg Y., Rost B., 2009 Correlating protein function and stability through the analysis of single amino acid substitutions. BMC Bioinformatics 10 Suppl 8: S8.

Brown C. a, Murray A. W., Verstrepen K. J., 2010 Rapid Expanion and Functional Divergence of Subtelomeric Gene Families in Yeasts. Curr. Biol. 20: 895-903.

Charron M. J., Michels C. A., 1988 The naturally occurring alleles of MAL1 in *Saccharomyces* species evolved by various mutagenic processes including chromosomal rearrangement. Genetics 120: 83-93.

Cheng Q., Michels C. A., 1989 The maltose permease encoded by the MAL61 gene of *Saccharomyces cerevisiae* exhibits both sequence and structural homology to other sugar transporters. Genetics 123.

Cousseau F. E. M., Alves S. L., Trichez D., Stambuk B. U., 2013 Characterization of maltotriose transporters from the *Saccharomyces eubayanus* subgenome of the hybrid *Saccharomyces pastorianus* lager brewing yeast strain Weihenstephan 34/70. Lett. Appl. Microbiol. 56: 21-29.

Daniel Gietz R., Woods R. A., 2002 Transformation of yeast by lithium acetate/single-stranded carrier DNA/polyethylene glycol method. Methods Enzymol. 350: 87-96.

Day R. E., Higgins V. J., Rogers P. J., Dawes I. W., 2002a Characterization of the putative maltose transporters encoded by YDL247w and YJR160c. Yeast 19: 1015-1027.

Day R. E., Rogers P. J., Dawes I. W., Higgins V. J., 2002b Molecular analysis of maltotriose transport and utilization by *Saccharomyces cerevisiae*. Appl. Environ. Microbiol. 68: 5326-35.

Denby C. M., Li R. A., Vu V. T., Costello Z., Lin W., et al., 2018 Industrial brewing yeast engineered for the production of primary flavor determinants in hopped beer. Nat. Commun. 9: 965.

Dietvorst J., Londesborough J., Steensma H. Y., 2005 Maltotriose utilization in lager yeast strains: MTT1 encodes a maltotriose transporter. Yeast 22: 775-788.

Dunham M. J., Badrane H., Ferea T., Adams J., Brown P. O., et al., 2002 Characteristic genome rearrangements in experimental evolution of *Saccharomyces cerevisiae*. Proc. Natl. Acad. Sci. 99: 16144-16149.

Edgar R. C., 2004 MUSCLE: multiple sequence alignment with high accuracy and high throughput. Nucleic Acids Res. 32: 1792-1797.

Ehrenreich I. M., Torabi N., Jia Y., Kent J., Martis S., et al., 2010 Dissection of genetically complex traits with extremely large pools of yeast segregants. Nature 464: 1039-1042. Eßlinger H. M., 2009 Fermentation, Maturation and Storage. In: Eßlinger HM (Ed.), *Handbook of brewing processes*, technology, markets, Weinheim (Germany), p. 209.

Gibson B. R., Storgårds E., Krogerus K., Vidgren V., 2013 Comparative physiology and fermentation performance of Saaz and Frohberg lager yeast strains and the parental species *Saccharomyces eubayanus*. Yeast 30: 255-266.

Gibson B., Liti G., 2015 *Saccharomyces pastorianus*: genomic insights inspiring innovation for industry. Yeast 32: 17-27.

Gibson B., Geertman J.-M. A., Hittinger C. T., Krogerus K., Libkind D., et al., 2017 New yeasts—new brews: modern approaches to brewing yeast design and development. FEMS Yeast Res. 17.

Han E., Cotty F., Sottas C., Jiang H., Michels C. A., 1995 Characterization of AGT1 encoding a general α-glucoside transporter from *Saccharomyces*. Mol. Microbiol. 17: 1093-1107.

Hebly M., Brickwedde A., Bolat I., Driessen M. R. M., Hulster E. A. F. de, et al., 2015 *Saccharomyces cerevi-* siae×*Saccharomyces eubayanus* interspecific hybrid, the best of both worlds and beyond. FEMS Yeast Res.

Henikoff S., Henikoff J. G., 1992 Amino acid substitution matrices from protein blocks. Biochemistry 89: 10915-10919.

Hittinger C. T., Steele J. L., Ryder D. S., 2018 Diverse yeasts for diverse fermented beverages and foods. Curr. Opin. Biotechnol. 49: 199-206.

Horák J., 2013 Regulations of sugar transporters: insights from yeast. Curr. Genet. 59: 1-31.

Johnson M. G., Gardner E. M., Liu Y., Medina R., Goffinet B., et al., 2016 HybPiper: Extracting coding sequence and introns for phylogenetics from high-throughput sequencing reads using target enrichment. Appl. Plant Sci. 4.

Kearse M., Moir R., Wilson A., Stones-Havas S., Cheung M., et al., 2012 Geneious Basic: An integrated and extendable desktop software platform for the organization and analysis of sequence data. Bioinformatics 28: 1647-1649.

Krogerus K., Magalhães F., Vidgren V., Gibson B., 2015 New lager yeast strains generated by interspecific hybridization. J. Ind. Microbiol. Biotechnol. 42: 769-778.

Krogerus K., Arvas M., Chiara M. De, Magalhães F., Mattinen L., et al., 2016 Ploidy influences the functional attributes of de novo lager yeast hybrids. Appl. Microbiol. Biotechnol. 100: 7203-22.

Krogerus K., Magalhães F., Vidgren V., Gibson B., 2017a Novel brewing yeast hybrids: creation and application. Appl. Microbiol. Biotechnol. 101: 65-78.

Krogerus K., Seppänen-Laakso T., Castillo S., Gibson B., 2017b Inheritance of brewing-relevant phenotypes in constructed *Saccharomyces cerevisiae*×*Saccharomyces eubayanus* hybrids. Microb. Cell Fact. 16: 66.

Kumar P., Henikoff S., Ng P. C., 2009 Predicting the effects of coding non-synonymous variants on protein function using the SIFT algorithm.

Libkind D., Hittinger C. T., Valêrio E., Gonçalves C., Dover J., et al., 2011 Microbe domestication and the identification of the wild genetic stock of lager-brewing yeast. Proc. Natl. Acad. Sci. U.S.A 108: 14539-14544.

Magalhães F., Vidgren V., Ruohonen L., Gibson B., 2016 Maltose and maltotriose utilisation by group I strains of the hybrid lager yeast *Saccharomyces pastorianus*. FEMS Yeast Res. 16.

Mertens S., Steensels J., Saels V., Rouck G. De, Aerts G., et al., 2015 A large set of newly created interspecific *Saccharomyces* hybrids increases aromatic diversity in lager beers. Appl. Environ. Microbiol. 81: 8202-14.

Meussdoerffer F., Zarnkow M., 2009 Starchy Raw Materials. In: *Handbook of brewing processes, technology*, markets, Weinheim (Germany), p. 58.

Nakao Y., Kanamori T., Itoh T., Kodama Y., Rainieri S., et al., 2009 Genome sequence of the lager brewing yeast, an interspecies hybrid. DNA Res. an Int. J. rapid Publ. reports genes genomes 16: 115-129.

Ng P. C., Henikoff S., 2001a Predicting deleterious amino acid substitutions. Genome Res. 11: 863-74.

Ng P. C., Henikoff S., 2001b Predicting deleterious amino acid substitutions. Genome Res. 11: 863-74.

Ng P. C., Henikoff S., 2002 Accounting for human polymorphisms predicted to affect protein function. Genome Res. 12: 436-46.

Ng P. C., Henikoff S., 2003 SIFT: Predicting amino acid changes that affect protein function. Nucleic Acids Res. 31: 3812-4.

Ng P. C., Henikoff S., 2006 Predicting the Effects of Amino Acid Substitutions on Protein Function. Annu. Rev. Genomics Hum. Genet 7: 61-80.

Nikulin J., Krogerus K., Gibson B., 2018 Alternative *Saccharomyces* interspecies hybrid combinations and their potential for low-temperature wort fermentation. Yeast 35: 113-127.

Okuno M., Kajitani R., Ryusui R., Morimoto H., Kodama Y., et al., 2016 Next-generation sequencing analysis of lager brewing yeast strains reveals the evolutionary history of interspecies hybridization. DNA Res. 23: dsv037.

Peris D., Sylvester K., Libkind D., Gonçalves P., Sampaio J. P., et al., 2014 Population structure and reticulate evolution of *Saccharomyces eubayanus* and its lager-brewing hybrids. Mol. Ecol. 23: 2031-2045.

Peris D., Langdon Q. K., Moriarty R. V., Sylvester K., Bontrager M., et al., 2016 Complex Ancestries of Lager-Brewing Hybrids Were Shaped by Standing Variation in the Wild Yeast *Saccharomyces eubayanus* (JC Fay, Ed.). PLOS Genet. 12: e1006155.

Peris D., Moriarty R. V., Alexander W. G., Baker E., Sylvester K., et al., 2017 Hybridization and adaptive evolution of diverse *Saccharomyces* species for cellulosic biofuel production. Biotechnol. Biofuels 10: 78.

Quan L., Lv Q., Zhang Y., 2016 STRUM: structure-based prediction of protein stability changes upon single-point mutation. Bioinformatics 32: 2936-2946.

Rautio J., Londesborough J., 2003 Maltose Transport by Brewer's Yeasts in Brewer's Wort. J. Inst. Brew. 109: 251-261.

Roy A., Kucukural A., Zhang Y., 2010 I-TASSER: a unified platform for automated protein structure and function prediction. Nat. Protoc. 5: 725-738.

Salema-Oom M., Valadão Pinto V., Gonçalves P., Spencer-Martins I., 2005 Maltotriose utilization by industrial *Saccharomyces* strains: characterization of a new member of the alpha-glucoside transporter family. Appl. Environ. Microbiol. 71: 5044-9.

Segrè A. V, Murray A. W., Leu J.-Y., 2006 High-Resolution Mutation Mapping Reveals Parallel Experimental Evolution in Yeast (K Wolfe, Ed.). PLoS Biol. 4: e256.

Slater G., Birney E., 2005 Automated generation of heuristics for biological sequence comparison. BMC Bioinformatics 6: 31.

Smit A., Moses S. G., Pretorius I. S., Cordero Otero R. R., 2008 The Thr505 and Ser557 residues of the AGT1-encoded alpha-glucoside transporter are critical for maltotriose transport in *Saccharomyces cerevisiae*. J. Appl. Microbiol. 104: 1103-11.

Stambuk B. U., Alves S. L., Hollatz C., Zastrow C. R., 2006 Improvement of maltotriose fermentation by *Saccharomyces cerevisiae*. Lett. Appl. Microbiol. 43: 370-376.

Strope P., Skelly D., Kozmin S., Mahadevan G., Stone E., et al., 2015 The 100-genomes strains, an *S. cerevisiae* resource that illuminates its natural phenotypic and genotypic variation and emergence as an opportunistic pathogen. Genome Biol. Evol.

Suyama M., Torrents D., Bork P., 2006 PAL2NAL: robust conversion of protein sequence alignments into the corresponding codon alignments. Nucleic Acids Res. 34: W609-W612. Vidgren V., Ruohonen L., Londesborough J., 2005 Characterization and functional analysis of the MAL and MPH Loci for maltose utilization in some ale and lager yeast strains. Appl. Environ. Microbiol. 71: 7846-57.

Vidgren V., Huuskonen A., Virtanen H., Ruohonen L., Londesborough J., 2009 Improved fermentation performance of a lager yeast after repair of its AGT1 maltose and maltotriose transporter genes. Appl. Environ. Microbiol. 75: 2333-45.

Vidgren V., Multanen J.-P., Ruohonen L., Londesborough J., 2010 The temperature dependence of maltose transport in ale and lager strains of brewer's yeast. FEMS Yeast Res. 10: 402-411.

Vidgren V., Londesborough J., 2012 Characterization of the *Saccharomyces bayanus*-type AGT1 transporter of lager yeast. J. Inst. Brew. 118: 148-151.

Wang X., Bali M., Medintz I., Michels C. A., 2002 Intracellular maltose is sufficient to induce MAL gene expression in *Saccharomyces cerevisiae*. Eukaryot. Cell 1: 696-703.

Wang J.-J., Wang Z.-Y., Liu X.-F., Guo X.-N., He X.-P., et al., 2010 Construction of an industrial brewing yeast strain to manufacture beer with low caloric content and improved flavor. J. Microbiol. Biotechnol. 20: 767-74.

Weisenfeld N. I., Yin S., Sharpe T., Lau B., Hegarty R., et al., 2014 Comprehensive variation discovery in single human genomes. Nat. Genet. 46: 1350-5.

Yan N., 2015 Structural Biology of the Major Facilitator Superfamily Transporters. Annu. Rev. Biophys. 44: 257-283.

Yang J., Yan R., Roy A., Xu D., Poisson J., et al., 2015 The I-TASSER Suite: protein structure and function prediction. Nat. Methods 12: 7-8.

Zhang Y., 2008 I-TASSER server for protein 3D structure prediction. BMC Bioinformatics 9: 40.

Zhou X., Peris D., Kominek J., Kurtzman C. P., Hittinger C. T., et al., 2016 in silico Whole Genome Sequencer & Analyzer (iWGS): A Computational Pipeline to Guide the Design and Analysis of de novo Genome Sequencing Studies. G3 (Bethesda). 6: 3655-3662.

We claim:

1. A DNA construct comprising a heterologous promoter operably linked to a polynucleotide encoding an alpha-glucoside transporter (AGT) polypeptide, wherein the AGT polypeptide has at least 95% sequence identity to SEQ ID NO: 7.

2. The DNA construct of claim 1, wherein the promoter is a yeast promoter.

3. A yeast cell comprising the DNA construct of claim 1.

4. A vector comprising the DNA construct of claim 1.

5. The vector of claim 4, wherein the vector comprises a plasmid.

6. A yeast cell comprising the vector of claim 4.

7. A yeast cell that expresses an alpha-glucoside transporter (AGT) polypeptide having at least 95% sequence identity to SEQ ID NO: 7, wherein the yeast cell has increased maltose/maltotriose transport activity as compared to a control yeast cell.

8. The yeast cell of claim 7, wherein the increased maltose/maltotriose transport activity is at the plasma membrane of the yeast cell.

9. The yeast cell of claim 7, wherein the yeast cell comprises a DNA construct comprising a heterologous promoter operably linked to a polynucleotide encoding the AGT polypeptide.

10. The yeast cell of claim 7, wherein the yeast cell comprises a vector comprising a DNA construct comprising a heterologous promoter operably linked to a polynucleotide encoding the AGT polypeptide.

11. The yeast cell of claim 7, wherein the yeast cell is from the genus *Saccharomyces*.

12. The yeast cell of claim 11, wherein the yeast cell is selected from the species consisting of *Saccharomyces eubayanus, Saccharomyces cerevisiae, Saccharomyces paradoxus, Saccharomyces mikatae, Saccharomyces arboricola, Saccharomyces kudriavzevii, Saccharomyces jurei,* and *Saccharomyces uvarum.*

13. The yeast cell of claim 7, wherein the yeast cell is a *Saccharomyces eubayanus* cell.

14. A method for making a fermentation product comprising culturing the yeast cells of claim 7 with a fermentable substrate to produce the fermentation product.

15. The method of claim 14, wherein the fermentable substrate comprises maltose or maltotriose.

16. The method of claim 14, wherein the fermentable substrate comprises wort or malt extract.

17. The method of claim 14, wherein the fermentation product is selected from the group consisting of a beer product, a wine product, an alcoholic beverage, a biochemical, and a biofuel.

* * * * *

UNITED STATES PATENT AND TRADEMARK OFFICE
CERTIFICATE OF CORRECTION

PATENT NO. : 11,725,213 B2
APPLICATION NO. : 17/341224
DATED : August 15, 2023
INVENTOR(S) : Chris Todd Hittinger et al.

It is certified that error appears in the above-identified patent and that said Letters Patent is hereby corrected as shown below:

In the Specification

Column 5, Line 27, "I1512S" should be --I512S--.

Column 5, Line 29, "V5385" should be --V538S--.

Column 10, Line 11, "Si" should be --S1--.

Column 26, Line 62, "MALT11" should be --MAL11--.

Column 26, Line 65, "MALT11" should be --MAL11--.

Column 27, Line 2, "MALT11" should be --MAL11--.

Column 30, Line 64, "(+/-0.03)" should be --(+/-0.00)--.

Column 30, Line 65, "(+/-0.03)" should be --(+/- 0.01)--.

Column 31, Line 56, "Fibackcross" should be --$F_1$ backcross--.

Signed and Sealed this
Seventh Day of November, 2023

*Katherine Kelly Vidal*
Katherine Kelly Vidal
*Director of the United States Patent and Trademark Office*

SEQUENCE LISTING

```
<160> NUMBER OF SEQ ID NOS: 52

<210> SEQ ID NO 1
<211> LENGTH: 613
<212> TYPE: PRT
<213> ORGANISM: Artificial Sequence
<220> FEATURE:
<223> OTHER INFORMATION: MALT434 Polypeptide Sequence MALT4 + MALT3
      portion

<400> SEQUENCE: 1

Met Lys Gly Leu Ser Ser Met Ile Asn Arg Lys Lys Cys Asn Gly Asn
1               5                   10                  15

Ser Ser Ser Ile Glu Thr Glu Gly Gly Phe Gly Ala Ala Glu Cys Asn
            20                  25                  30

Ser Ile Glu Leu Glu Glu Gln Gly Lys Lys Thr Asp Phe Asp Leu Ala
        35                  40                  45

His Leu Glu Tyr Gly Gln Gly Pro Ala Ala Leu Ser Glu Asn Asp Glu
    50                  55                  60

Val Thr Pro Asn Ile Leu Asp Ala Ala Gln Asp Ala Lys Glu Ala Asp
65                  70                  75                  80

Asp Ser Glu Arg Glu Met Pro Leu Met Thr Ala Leu Lys Thr Tyr Pro
                85                  90                  95

Lys Ala Ala Ala Trp Ser Leu Leu Val Ser Thr Thr Leu Ile Gln Glu
            100                 105                 110

Gly Tyr Asp Thr Ala Ile Leu Gly Ser Phe Tyr Ala Leu Pro Val Phe
        115                 120                 125

Gln Lys Lys Tyr Gly Ser Leu Asn Ala Arg Thr Gly Glu Trp Glu Ile
    130                 135                 140

Ser Val Ser Trp Gln Ile Gly Leu Cys Leu Cys Tyr Met Ala Gly Glu
145                 150                 155                 160

Ile Val Gly Leu Gln Leu Thr Gly Pro Ser Val Asp Leu Met Gly Asn
                165                 170                 175

Arg Tyr Thr Leu Ile Met Ala Leu Met Phe Leu Thr Ala Phe Ile Phe
            180                 185                 190

Ile Leu Tyr Phe Cys Lys Ser Leu Gly Met Ile Ala Ala Gly Gln Ala
        195                 200                 205

Leu Cys Gly Met Pro Trp Gly Cys Phe Gln Cys Leu Thr Val Ser Tyr
    210                 215                 220

Ala Ser Glu Ile Cys Pro Met Ala Leu Arg Tyr Tyr Leu Thr Thr Tyr
225                 230                 235                 240
```

Ser Asn Leu Cys Trp Leu Phe Gly Gln Leu Phe Ala Ala Gly Ile Met
            245                 250                 255

Lys Asn Ser Gln Asn Lys Tyr Ala Asp Ser Asp Leu Gly Tyr Thr Leu
            260                 265                 270

Pro Phe Ala Leu Gln Trp Ile Trp Pro Val Pro Leu Ala Ile Ala Ile
            275                 280                 285

Phe Phe Ala Pro Glu Ser Pro Trp Trp Leu Val Lys Lys Gly Arg Leu
            290                 295                 300

Glu Gln Ala Lys Arg Ser Leu Glu Arg Thr Leu Ser Gly Lys Gly Ala
305                 310                 315                 320

Glu Lys Glu Ser Leu Val Ala Met Glu Leu Asp Lys Ile Lys Met Thr
            325                 330                 335

Ile Glu Lys Glu Lys Lys Leu Ser Asp Asp Glu Gly Ser Tyr Leu Asp
            340                 345                 350

Cys Leu Arg Gly Lys Val Asn Arg Arg Thr Arg Ile Ala Cys Leu
            355                 360                 365

Cys Trp Ala Gly Gln Thr Val Cys Gly Ala Ser Leu Ile Gly Tyr Ser
            370                 375                 380

Thr Tyr Phe Tyr Glu Lys Ala Gly Val Ser Thr Glu Thr Ala Phe Thr
385                 390                 395                 400

Phe Ser Ile Ile Gln Tyr Cys Leu Gly Ile Ala Ala Thr Phe Leu Ser
            405                 410                 415

Trp Trp Ala Ser Lys Tyr Tyr Gly Arg Tyr Asp Leu Tyr Ala Cys Gly
            420                 425                 430

Leu Ala Phe Gln Thr Val Ile Leu Phe Ile Ile Gly Gly Leu Gly Cys
            435                 440                 445

Ser Asp Thr His Gly Ala Lys Met Gly Ser Gly Ala Leu Leu Met Val
            450                 455                 460

Val Ala Phe Phe Tyr Asn Leu Gly Ile Ala Pro Val Val Phe Cys Leu
465                 470                 475                 480

Val Ser Glu Ile Pro Ser Ser Arg Leu Arg Thr Lys Ser Ile Ile Leu
            485                 490                 495

Ala Arg Asn Ala Tyr Asn Met Ala Cys Ile Val Thr Ala Val Leu Thr
            500                 505                 510

Leu Tyr Gln Leu Asn Ser Glu Lys Trp Asp Trp Gly Ala Lys Ser Gly
            515                 520                 525

Phe Phe Trp Gly Gly Leu Cys Phe Ala Thr Leu Val Trp Ala Val Phe
            530                 535                 540

Asp Leu Pro Glu Thr Ala Gly Arg Thr Phe Ile Glu Ile Asn Glu Leu
545                 550                 555                 560

Phe Arg Leu Gly Val Pro Ala Arg Lys Phe Lys Ser Thr Lys Val Asp
            565                 570                 575

Pro Phe Ala Ala Ala Lys Ala Ile Ser Asp Glu Ile Asn His Lys Asp
            580                 585                 590

Pro Lys Glu Asp Met Lys Ala Ser Ala Glu Glu Arg Gly Gln Ser Thr
            595                 600                 605

Pro Ser Leu Met Asp
    610

<210> SEQ ID NO 2
<211> LENGTH: 613
<212> TYPE: PRT
<213> ORGANISM: Artificial Sequence
<220> FEATURE:

<223> OTHER INFORMATION: MALT433 Chimeric Protein with N-terminus MALT4 and C-terminus MALT3

<400> SEQUENCE: 2

```
Met Lys Gly Leu Ser Ser Met Ile Asn Arg Lys Lys Cys Asn Gly Asn
1               5                   10                  15

Ser Ser Ser Ile Glu Thr Glu Gly Phe Gly Ala Ala Glu Cys Asn
                20                  25                  30

Ser Ile Glu Leu Glu Glu Gln Gly Lys Lys Thr Asp Phe Asp Leu Ala
                35                  40                  45

His Leu Glu Tyr Gly Gln Gly Pro Ala Ala Leu Ser Glu Asn Asp Glu
            50                  55                  60

Val Thr Pro Asn Ile Leu Asp Ala Ala Gln Asp Ala Lys Glu Ala Asp
65                  70                  75                  80

Asp Ser Glu Arg Glu Met Pro Leu Met Thr Ala Leu Lys Thr Tyr Pro
                85                  90                  95

Lys Ala Ala Ala Trp Ser Leu Leu Val Ser Thr Thr Leu Ile Gln Glu
            100                 105                 110

Gly Tyr Asp Thr Ala Ile Leu Gly Ser Phe Tyr Ala Leu Pro Val Phe
            115                 120                 125

Gln Lys Lys Tyr Gly Ser Leu Asn Ala Arg Thr Gly Glu Trp Glu Ile
            130                 135                 140

Ser Val Ser Trp Gln Ile Gly Leu Cys Leu Cys Tyr Met Ala Gly Glu
145                 150                 155                 160

Ile Val Gly Leu Gln Leu Thr Gly Pro Ser Val Asp Leu Met Gly Asn
                165                 170                 175

Arg Tyr Thr Leu Ile Met Ala Leu Met Phe Leu Thr Ala Phe Ile Phe
            180                 185                 190

Ile Leu Tyr Phe Cys Lys Ser Leu Gly Met Ile Ala Ala Gly Gln Ala
            195                 200                 205

Leu Cys Gly Met Pro Trp Gly Cys Phe Gln Cys Leu Thr Val Ser Tyr
            210                 215                 220

Ala Ser Glu Ile Cys Pro Met Ala Leu Arg Tyr Tyr Leu Thr Thr Tyr
225                 230                 235                 240

Ser Asn Leu Cys Trp Leu Phe Gly Gln Leu Phe Ala Ala Gly Ile Met
                245                 250                 255

Lys Asn Ser Gln Asn Lys Tyr Ala Asp Ser Asp Leu Gly Tyr Thr Leu
            260                 265                 270

Pro Phe Ala Leu Gln Trp Ile Trp Pro Val Pro Leu Ala Ile Ala Ile
            275                 280                 285

Phe Phe Ala Pro Glu Ser Pro Trp Trp Leu Val Lys Lys Gly Arg Leu
            290                 295                 300

Glu Gln Ala Lys Arg Ser Leu Glu Arg Thr Leu Ser Gly Lys Gly Ala
305                 310                 315                 320

Glu Lys Glu Ser Leu Val Ala Met Glu Leu Asp Lys Ile Lys Met Thr
                325                 330                 335

Ile Glu Lys Glu Lys Lys Leu Ser Asp Asp Glu Gly Ser Tyr Leu Asp
            340                 345                 350

Cys Leu Arg Gly Lys Val Asn Arg Arg Thr Arg Ile Ala Cys Leu
            355                 360                 365

Cys Trp Ala Gly Gln Thr Val Cys Gly Ala Ser Leu Ile Gly Tyr Ser
            370                 375                 380

Thr Tyr Phe Tyr Glu Lys Ala Gly Val Ser Thr Glu Thr Ala Phe Thr
385                 390                 395                 400
```

```
Phe Ser Ile Ile Gln Tyr Cys Leu Gly Ile Ala Ala Thr Phe Leu Ser
                405                 410                 415

Trp Trp Ala Ser Lys Tyr Tyr Gly Arg Tyr Asp Leu Tyr Ala Cys Gly
            420                 425                 430

Leu Ala Phe Gln Thr Val Ile Leu Phe Ile Ile Gly Gly Leu Gly Cys
        435                 440                 445

Ser Asp Thr His Gly Ala Lys Met Gly Ser Gly Ala Leu Leu Met Val
    450                 455                 460

Val Ala Phe Phe Tyr Asn Leu Gly Ile Ala Pro Val Val Phe Cys Leu
465                 470                 475                 480

Val Ser Glu Ile Pro Ser Ser Arg Leu Arg Thr Lys Ser Ile Ile Leu
                485                 490                 495

Ala Arg Asn Ala Tyr Asn Met Ala Cys Ile Val Thr Ala Val Leu Thr
            500                 505                 510

Leu Tyr Gln Leu Asn Ser Glu Lys Trp Asp Trp Gly Ala Lys Ser Gly
        515                 520                 525

Phe Phe Trp Gly Gly Leu Cys Phe Ala Thr Leu Val Trp Ala Val Ile
    530                 535                 540

Asp Leu Pro Glu Thr Ala Gly Arg Thr Phe Met Glu Met Asn Glu Leu
545                 550                 555                 560

Phe Arg Leu Gly Ile Pro Ala Arg Lys Phe Lys Thr Thr Lys Val Asp
                565                 570                 575

Pro Phe Ala Ala Val Lys Ala Ala Lys Glu Ile Ala His Asn Asp Pro
            580                 585                 590

Lys Glu Asp Met Glu Thr Ser Met Val Glu Gly Gly Arg Ser Thr Pro
        595                 600                 605

Ser Ile Thr Asn Leu
    610

<210> SEQ ID NO 3
<211> LENGTH: 614
<212> TYPE: PRT
<213> ORGANISM: Artificial Sequence
<220> FEATURE:
<223> OTHER INFORMATION: MALT334 Chimeric Protein with N-terminus MALT3

<400> SEQUENCE: 3

Met Lys Gly Leu Ser Ser Leu Ile Asn Arg Lys Asn Lys Ile Asp
1               5                   10                  15

Ser Asn Ser Asn Glu Ile Glu Asn Gly Met Asn Ser Thr Asp Leu Asn
                20                  25                  30

Ser Ile Glu Met Gln Glu Gln Gly Lys Lys Ser Asp Phe Asp Leu Ser
            35                  40                  45

His Ile Glu Tyr Gly Gln Asp Ser Arg Val Pro Lys Asp Asp Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Leu Gln Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ser Phe Tyr Ala Leu Pro Val
        115                 120                 125

Phe Gln Lys Glu Tyr Gly Ser Leu Asn Ser Lys Thr Gly Glu Tyr Glu
    130                 135                 140
```

```
Ile Ser Val Ser Trp Gln Ile Gly Leu Ser Leu Cys Ile Val Ala Gly
145                 150                 155                 160

Glu Ile Val Gly Leu Gln Met Thr Gly Pro Phe Val Asp Tyr Met Gly
            165                 170                 175

Asn Arg Tyr Thr Leu Ile Val Ala Leu Phe Phe Leu Ala Ala Phe Thr
            180                 185                 190

Phe Ile Leu Tyr Phe Cys Lys Ser Leu Gly Met Ile Ala Val Gly Gln
        195                 200                 205

Val Leu Cys Gly Met Pro Trp Gly Cys Phe Gln Cys Leu Thr Val Ser
    210                 215                 220

Tyr Ala Ser Glu Ile Cys Pro Leu Ala Leu Arg Tyr Tyr Leu Thr Thr
225                 230                 235                 240

Tyr Ser Asn Leu Cys Trp Thr Phe Gly Gln Leu Phe Ala Ala Gly Ile
                245                 250                 255

Met Lys Asn Ser Gln Asn Lys Tyr Pro Asp Ser Asp Leu Gly Tyr Lys
        260                 265                 270

Leu Pro Phe Ala Leu Gln Trp Ile Trp Pro Leu Pro Leu Ala Ile Gly
        275                 280                 285

Ile Phe Phe Ala Pro Glu Ser Pro Trp Trp Leu Ile Lys Lys Gly Arg
290                 295                 300

Met Glu Gln Ala Lys Lys Ser Leu Glu Arg Thr Leu Ser Gly Lys Gly
305                 310                 315                 320

Pro Glu Lys Glu Leu Leu Val Ser Met Glu Leu Asp Lys Ile Lys Val
                325                 330                 335

Thr Ile Glu Lys Glu Gln Lys Met Ser Asp Ser Glu Gly Ser Tyr Trp
            340                 345                 350

Asp Cys Val Lys Asp Cys Ile Asn Arg Arg Thr Arg Ile Ala Cys
                355                 360                 365

Leu Cys Trp Ile Gly Gln Thr Thr Cys Gly Thr Gln Leu Ile Gly Tyr
    370                 375                 380

Ser Thr Tyr Phe Tyr Glu Lys Ala Gly Val Ser Thr Glu Thr Ala Phe
385                 390                 395                 400

Thr Phe Ser Ile Ile Gln Tyr Cys Leu Gly Ile Val Ala Thr Leu Leu
                405                 410                 415

Ser Trp Trp Ala Ser Lys Tyr Phe Gly Arg Phe Asp Leu Tyr Ala Phe
            420                 425                 430

Gly Leu Ala Ile Gln Thr Val Leu Leu Phe Ile Ile Gly Gly Leu Gly
        435                 440                 445

Cys Ser Asp Thr His Gly Ala Gln Met Gly Ser Gly Ala Leu Leu Met
    450                 455                 460

Val Val Ala Phe Phe Tyr Asn Leu Gly Ile Ala Pro Val Val Phe Cys
465                 470                 475                 480

Leu Val Ser Glu Ile Pro Ser Ser Arg Leu Arg Thr Lys Ser Ile Ile
                485                 490                 495

Leu Ala Arg Asn Ala Tyr Asn Met Ala Cys Ile Val Thr Ala Val Leu
            500                 505                 510

Thr Leu Tyr Gln Leu Asn Ser Glu Lys Trp Asp Trp Gly Ala Lys Ser
        515                 520                 525

Gly Phe Phe Trp Gly Gly Leu Cys Phe Ala Thr Leu Val Trp Ala Val
        530                 535                 540

Phe Asp Leu Pro Glu Thr Ala Gly Arg Thr Phe Ile Glu Ile Asn Glu
545                 550                 555                 560
```

```
Leu Phe Arg Leu Gly Val Pro Ala Arg Lys Phe Lys Ser Thr Lys Val
                565                 570                 575

Asp Pro Phe Ala Ala Lys Ala Ile Ser Asp Glu Ile Asn His Lys
            580                 585                 590

Asp Pro Lys Glu Asp Met Lys Ala Ser Ala Glu Glu Arg Glu Gln Ser
        595                 600                 605

Thr Pro Ser Leu Met Asp
        610

<210> SEQ ID NO 4
<211> LENGTH: 613
<212> TYPE: PRT
<213> ORGANISM: Saccharomyces eubayanus
<220> FEATURE:
<221> NAME/KEY: MISC_FEATURE
<222> LOCATION: (1)..(613)
<223> OTHER INFORMATION: FM1318 Malt4

<400> SEQUENCE: 4

Met Lys Gly Leu Ser Ser Met Ile Asn Arg Lys Lys Cys Asn Gly Asn
1               5                   10                  15

Ser Ser Ser Ile Glu Thr Glu Gly Gly Phe Gly Ala Ala Glu Cys Asn
            20                  25                  30

Ser Ile Glu Leu Glu Glu Gln Gly Lys Lys Thr Asp Phe Asp Leu Ala
        35                  40                  45

His Leu Glu Tyr Gly Gln Gly Pro Ala Ala Leu Ser Glu Asn Asp Glu
    50                  55                  60

Val Thr Pro Asn Ile Leu Asp Ala Ala Gln Asp Ala Lys Glu Ala Asp
65                  70                  75                  80

Asp Ser Glu Arg Glu Met Pro Leu Met Thr Ala Leu Lys Thr Tyr Pro
                85                  90                  95

Lys Ala Ala Ala Trp Ser Leu Leu Val Ser Thr Thr Leu Ile Gln Glu
            100                 105                 110

Gly Tyr Asp Thr Ala Ile Leu Gly Ser Phe Tyr Ala Leu Pro Val Phe
        115                 120                 125

Gln Lys Lys Tyr Gly Ser Leu Asn Ala Arg Thr Gly Glu Trp Glu Ile
    130                 135                 140

Ser Val Ser Trp Gln Ile Gly Leu Cys Leu Cys Tyr Met Ala Gly Glu
145                 150                 155                 160

Ile Val Gly Leu Gln Leu Thr Gly Pro Ser Val Asp Leu Met Gly Asn
                165                 170                 175

Arg Tyr Thr Leu Ile Met Ala Leu Met Phe Leu Thr Ala Phe Ile Phe
            180                 185                 190

Ile Leu Tyr Phe Cys Lys Ser Leu Gly Met Ile Ala Ala Gly Gln Ala
        195                 200                 205

Leu Cys Gly Met Pro Trp Gly Cys Phe Gln Cys Leu Thr Val Ser Tyr
    210                 215                 220

Ala Ser Glu Ile Cys Pro Met Ala Leu Arg Tyr Tyr Leu Thr Thr Tyr
225                 230                 235                 240

Ser Asn Leu Cys Trp Leu Phe Gly Gln Leu Phe Ala Ala Gly Ile Met
                245                 250                 255

Lys Asn Ser Gln Asn Lys Tyr Ala Asp Ser Asp Leu Gly Tyr Thr Leu
            260                 265                 270

Pro Phe Ala Leu Gln Trp Ile Trp Pro Val Pro Leu Ala Ile Ala Ile
        275                 280                 285

Phe Phe Ala Pro Glu Ser Pro Trp Trp Leu Val Lys Lys Gly Arg Leu
```

```
                 290                 295                 300
Glu Gln Ala Lys Arg Ser Leu Glu Arg Thr Leu Ser Gly Lys Gly Ala
305                 310                 315                 320

Glu Lys Glu Ser Leu Val Ala Met Glu Leu Asp Lys Ile Lys Met Thr
                325                 330                 335

Ile Glu Lys Glu Lys Lys Leu Ser Asp Asp Glu Gly Ser Tyr Leu Asp
                340                 345                 350

Cys Leu Arg Gly Lys Val Asn Arg Arg Thr Arg Ile Ala Cys Leu
            355                 360                 365

Cys Trp Ala Gly Gln Thr Val Cys Gly Ala Ser Leu Ile Gly Tyr Ser
            370                 375                 380

Thr Tyr Phe Tyr Glu Lys Ala Gly Val Ser Thr Glu Thr Ala Phe Thr
385                 390                 395                 400

Phe Ser Ile Ile Gln Tyr Cys Leu Gly Ile Ala Ala Thr Phe Leu Ser
                405                 410                 415

Trp Trp Ala Ser Lys Tyr Tyr Gly Arg Tyr Asp Leu Tyr Ala Cys Gly
            420                 425                 430

Leu Ala Phe Gln Thr Val Ile Leu Phe Ile Ile Gly Gly Leu Gly Cys
            435                 440                 445

Ser Asp Thr His Gly Ala Lys Met Gly Ser Gly Ala Leu Leu Met Val
450                 455                 460

Val Ala Phe Ser Tyr Asn Leu Gly Ile Ala Pro Val Val Phe Cys Leu
465                 470                 475                 480

Val Ser Glu Ile Pro Ser Ser Arg Leu Arg Thr Lys Ser Ile Ile Leu
                485                 490                 495

Ala Arg Asn Ala Tyr Asn Ile Gly Asn Ile Val Val Ala Val Leu Ile
            500                 505                 510

Leu Tyr Gln Leu Asn Ser Glu Lys Trp Asn Trp Gly Ala Lys Ser Gly
            515                 520                 525

Phe Phe Trp Gly Gly Phe Cys Leu Ala Val Leu Ile Trp Ala Val Phe
            530                 535                 540

Asp Leu Pro Glu Thr Ala Gly Arg Thr Phe Ile Glu Ile Asn Glu Leu
545                 550                 555                 560

Phe Arg Leu Gly Val Pro Ala Arg Lys Phe Lys Ser Thr Lys Val Asp
                565                 570                 575

Pro Phe Ala Ala Lys Ala Ile Ser Asp Glu Ile Asn His Lys Asp
            580                 585                 590

Pro Lys Glu Asp Met Lys Ala Ser Ala Glu Glu Arg Glu Gln Ser Thr
            595                 600                 605

Pro Ser Leu Met Asp
            610

<210> SEQ ID NO 5
<211> LENGTH: 614
<212> TYPE: PRT
<213> ORGANISM: Saccharomyces eubayanus
<220> FEATURE:
<221> NAME/KEY: MISC_FEATURE
<222> LOCATION: (1)..(614)
<223> OTHER INFORMATION: FM1318 Malt3

<400> SEQUENCE: 5

Met Lys Gly Leu Ser Ser Leu Ile Asn Arg Lys Lys Asn Lys Ile Asp
1               5                   10                  15

Ser Asn Ser Asn Glu Ile Glu Asn Gly Met Asn Ser Thr Asp Leu Asn
                20                  25                  30
```

```
Ser Ile Glu Met Gln Glu Gln Gly Lys Lys Ser Asp Phe Asp Leu Ser
            35                  40                  45

His Ile Glu Tyr Gly Gln Asp Ser Arg Val Pro Lys Asp Asp Asp Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Leu Gln Ala Leu Lys Thr Tyr
                85                  90                  95

Pro Lys Ala Ala Ala Trp Ser Leu Leu Val Ser Thr Thr Leu Ile Gln
                100                 105                 110

Glu Gly Tyr Asp Thr Ala Ile Leu Gly Ser Phe Tyr Ala Leu Pro Val
                115                 120                 125

Phe Gln Lys Glu Tyr Gly Ser Leu Asn Ser Lys Thr Gly Glu Tyr Glu
                130                 135                 140

Ile Ser Val Ser Trp Gln Ile Gly Leu Ser Leu Cys Ile Val Ala Gly
145                 150                 155                 160

Glu Ile Val Gly Leu Gln Met Thr Gly Pro Phe Val Asp Tyr Met Gly
                165                 170                 175

Asn Arg Tyr Thr Leu Ile Val Ala Leu Phe Phe Leu Ala Ala Phe Thr
                180                 185                 190

Phe Ile Leu Tyr Phe Cys Lys Ser Leu Gly Met Ile Ala Val Gly Gln
                195                 200                 205

Val Leu Cys Gly Met Pro Trp Gly Cys Phe Gln Cys Leu Thr Val Ser
                210                 215                 220

Tyr Ala Ser Glu Ile Cys Pro Leu Ala Leu Arg Tyr Tyr Leu Thr Thr
225                 230                 235                 240

Tyr Ser Asn Leu Cys Trp Thr Phe Gly Gln Leu Phe Ala Ala Gly Ile
                245                 250                 255

Met Lys Asn Ser Gln Asn Lys Tyr Pro Asp Ser Asp Leu Gly Tyr Lys
                260                 265                 270

Leu Pro Phe Ala Leu Gln Trp Ile Trp Pro Leu Pro Leu Ala Ile Gly
                275                 280                 285

Ile Phe Phe Ala Pro Glu Ser Pro Trp Trp Leu Ile Lys Lys Gly Arg
                290                 295                 300

Met Glu Gln Ala Lys Lys Ser Leu Glu Arg Thr Leu Ser Gly Lys Gly
305                 310                 315                 320

Pro Glu Lys Glu Leu Leu Val Ser Met Glu Leu Asp Lys Ile Lys Val
                325                 330                 335

Thr Ile Glu Lys Glu Gln Lys Met Ser Asp Ser Glu Gly Ser Tyr Trp
                340                 345                 350

Asp Cys Val Lys Asp Cys Ile Asn Arg Arg Thr Arg Ile Ala Cys
                355                 360                 365

Leu Cys Trp Ile Gly Gln Thr Thr Cys Gly Thr Gln Leu Ile Gly Tyr
                370                 375                 380

Ser Thr Tyr Phe Tyr Glu Lys Ala Gly Val Ser Thr Glu Thr Ala Phe
385                 390                 395                 400

Thr Phe Ser Ile Ile Gln Tyr Cys Leu Gly Ile Val Ala Thr Leu Leu
                405                 410                 415

Ser Trp Trp Ala Ser Lys Tyr Phe Gly Arg Phe Asp Leu Tyr Ala Phe
                420                 425                 430

Gly Leu Ala Ile Gln Thr Val Leu Leu Phe Ile Ile Gly Gly Leu Gly
                435                 440                 445
```

-continued

```
Cys Ser Asp Thr His Gly Ala Gln Met Gly Ser Gly Ala Leu Leu Met
    450                 455                 460
Val Val Ala Phe Phe Tyr Asn Leu Gly Ile Ala Pro Val Val Phe Cys
465                 470                 475                 480
Leu Val Ser Glu Ile Pro Ser Ser Arg Leu Arg Thr Lys Ser Ile Ile
                485                 490                 495
Leu Ala Arg Asn Ala Tyr Asn Met Ala Cys Ile Val Thr Ala Val Leu
            500                 505                 510
Thr Leu Tyr Gln Leu Asn Ser Glu Lys Trp Asp Trp Gly Ala Lys Ser
        515                 520                 525
Gly Phe Phe Trp Gly Gly Leu Cys Phe Ala Thr Leu Val Trp Ala Val
    530                 535                 540
Ile Asp Leu Pro Glu Thr Ala Gly Arg Thr Phe Met Glu Met Asn Glu
545                 550                 555                 560
Leu Phe Arg Leu Gly Ile Pro Ala Arg Lys Phe Lys Thr Thr Lys Val
                565                 570                 575
Asp Pro Phe Ala Ala Val Lys Ala Ala Lys Glu Ile Ala His Asn Asp
            580                 585                 590
Pro Lys Glu Asp Met Glu Thr Ser Met Val Glu Glu Gly Arg Ser Thr
        595                 600                 605
Pro Ser Ile Thr Asn Leu
    610

<210> SEQ ID NO 6
<211> LENGTH: 610
<212> TYPE: PRT
<213> ORGANISM: Unknown
<220> FEATURE:
<223> OTHER INFORMATION: yHAB47 lager hybrid lgAGT1

<400> SEQUENCE: 6

Met Lys Asn Ile Leu Ser Leu Val Gly Arg Lys Glu Asn Thr Pro Glu
1               5                   10                  15
Asp Val Thr Ala Asn Leu Ala Asp Thr Ser Ser Thr Thr Val Met Gln
            20                  25                  30
Ala Lys Asp Leu Val Ile Glu Asp Phe Glu Arg Lys Lys Asn Asp
        35                  40                  45
Ala Phe Glu Leu Asn His Leu Glu Leu Thr Thr Asn Ala Thr Gln Leu
    50                  55                  60
Ser Asp Ser Asp Glu Asp Lys Glu Asn Val Ile Arg Val Ala Glu Ala
65                  70                  75                  80
Thr Asp Asp Ala Asn Glu Ala Asn Asn Glu Lys Ser Met Thr Leu
                85                  90                  95
Arg Gln Ala Leu Arg Lys Tyr Pro Lys Ala Ala Leu Trp Ser Ile Leu
            100                 105                 110
Val Ser Thr Thr Leu Val Met Glu Gly Tyr Asp Thr Ala Leu Leu Ser
        115                 120                 125
Ala Leu Tyr Ala Leu Pro Val Phe Gln Arg Lys Phe Gly Thr Met Asn
    130                 135                 140
Ala Glu Gly Ser Tyr Glu Ile Thr Ser Gln Trp Gln Ile Gly Leu Asn
145                 150                 155                 160
Met Cys Val Leu Cys Gly Glu Met Ile Gly Leu Gln Ile Thr Thr Tyr
                165                 170                 175
Met Val Glu Phe Met Gly Asn Arg Tyr Thr Met Ile Thr Ala Leu Ser
            180                 185                 190
```

```
Leu Leu Thr Ala Tyr Ile Phe Ile Leu Tyr Tyr Cys Lys Ser Leu Ala
            195                 200                 205

Met Ile Ala Val Gly Gln Ile Leu Ser Ala Met Pro Trp Gly Cys Phe
    210                 215                 220

Gln Ser Leu Ala Val Thr Tyr Ala Ser Glu Val Cys Pro Leu Ala Leu
225                     230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
        275                 280                 285

Ala Pro Leu Ile Ile Gly Ile Phe Phe Ala Pro Glu Ser Pro Trp Trp
    290                 295                 300

Leu Val Arg Lys Asn Lys Ile Val Glu Ala Lys Lys Ser Leu Asn Arg
305                 310                 315                 320

Ile Leu Ser Gly Thr Val Thr Glu Lys Glu Ile Gln Val Asp Ile Thr
                325                 330                 335

Leu Lys Gln Ile Glu Met Thr Ile Glu Lys Glu Arg Leu Arg Ala Ser
            340                 345                 350

Lys Ser Gly Ser Phe Phe Ser Cys Phe Lys Gly Val Asp Gly Arg Arg
        355                 360                 365

Thr Arg Leu Ala Cys Leu Thr Trp Val Ala Gln Asn Ser Ser Gly Ala
    370                 375                 380

Val Leu Leu Gly Tyr Ser Thr Tyr Phe Phe Glu Arg Ala Gly Met Ala
385                 390                 395                 400

Thr Asp Lys Ala Phe Thr Phe Ser Leu Ile Gln Tyr Cys Leu Gly Leu
                405                 410                 415

Ala Gly Thr Leu Gly Ser Trp Val Ile Ser Arg Val Gly Arg Trp
            420                 425                 430

Thr Ile Leu Thr Tyr Gly Leu Ser Phe Gln Met Val Cys Leu Phe Ile
        435                 440                 445

Ile Gly Gly Met Gly Phe Ala Ser Gly Ser Ser Ala Ser Asn Ala Ala
    450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
            500                 505                 510

Phe Asn Ala Ile Leu Thr Pro Tyr Met Leu Asn Val Ser Asp Trp Asn
        515                 520                 525

Trp Gly Ala Lys Thr Gly Leu Tyr Trp Gly Gly Phe Thr Ala Leu Thr
    530                 535                 540

Leu Ala Trp Val Ile Ile Asp Leu Pro Glu Thr Thr Gly Arg Thr Phe
545                 550                 555                 560

Ser Glu Ile Asn Glu Leu Phe Ser Gln Gly Val Pro Ala Arg Lys Phe
                565                 570                 575

Ala Ser Thr Val Val Asp Pro Phe Gly Lys Arg Gly Leu Gln Asn Arg
            580                 585                 590

Pro Gln Val Asp Asn Ile Ile Asp Arg Phe Ser Ser Ala Ser Gln Gln
        595                 600                 605

Ala Leu
```

<210> SEQ ID NO 7
<211> LENGTH: 610
<212> TYPE: PRT
<213> ORGANISM: Saccharomyces eubayanus
<220> FEATURE:
<221> NAME/KEY: MISC_FEATURE
<222> LOCATION: (1)..(610)
<223> OTHER INFORMATION: yHRVM108 ncAGT1

<400> SEQUENCE: 7

```
Met Lys Asn Ile Ile Ser Leu Val Arg Arg Lys Gly Asn Thr Pro Glu
1               5                   10                  15

Asp Glu Thr Glu Asn Leu Glu Asp Thr Ser Ser Thr Thr Val Met Gln
            20                  25                  30

Ala Lys Asp Leu Asp Ile Glu Asp Phe Glu Arg Lys Lys Asn Asp
        35                  40                  45

Ala Phe Glu Leu Asn His Met Glu Leu Thr Thr Asn Ala Thr Gln Leu
    50                  55                  60

Gly Asp Ser Asp Gly Asp Asn Asp Asn Ala Ile Arg Val Ala Glu Ala
65                  70                  75                  80

Thr Asp Asp Ala Asn Glu Ala Asn Asn Glu Glu Lys Ser Met Thr Leu
                85                  90                  95

Arg Gln Ala Leu Arg Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
        115                 120                 125

Ala Leu Tyr Ala Leu Pro Val Phe Gln Arg Lys Phe Gly Thr Met Asn
    130                 135                 140

Ala Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Met Thr Thr Tyr
                165                 170                 175

Met Val Glu Phe Met Gly Asn Arg Tyr Thr Met Ile Met Ala Leu Phe
            180                 185                 190

Leu Leu Thr Ala Tyr Ile Phe Ile Leu Tyr Tyr Cys Lys Ser Leu Ala
        195                 200                 205

Met Ile Ala Val Gly Gln Ile Leu Ser Ala Met Pro Trp Gly Cys Phe
    210                 215                 220

Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asp
            260                 265                 270

Ser Asp Leu Gly Tyr Lys Leu Pro Phe Ala Leu Gln Trp Ile Trp Pro
        275                 280                 285

Ala Pro Leu Ile Ile Gly Ile Phe Phe Ala Pro Glu Ser Pro Trp Trp
    290                 295                 300

Leu Val Arg Lys Asn Lys Ile Val Glu Ala Lys Lys Ser Leu Asn Arg
305                 310                 315                 320

Ile Leu Ser Gly Thr Ala Thr Glu Lys Glu Ile Gln Val Asp Ile Thr
                325                 330                 335

Leu Lys Gln Ile Glu Met Thr Ile Glu Lys Glu Arg Leu Arg Ala Ser
            340                 345                 350
```

```
Glu Ser Gly Ser Phe Phe Ser Cys Phe Lys Gly Val Asp Gly Arg Arg
            355                 360                 365

Thr Arg Leu Ala Cys Leu Thr Trp Val Ala Gln Asn Ser Ser Gly Ala
        370                 375                 380

Val Leu Leu Gly Tyr Ser Thr Tyr Phe Glu Arg Ala Gly Met Asp
385                 390                 395                 400

Thr Asp Lys Ala Phe Thr Phe Ser Leu Ile Gln Tyr Cys Leu Gly Leu
                405                 410                 415

Ala Gly Thr Leu Cys Ser Trp Val Ile Ser Gly Arg Val Gly Arg Trp
            420                 425                 430

Thr Ile Leu Thr Tyr Gly Leu Ser Phe Gln Met Val Cys Leu Phe Ile
        435                 440                 445

Ile Gly Gly Met Gly Phe Ala Ser Gly Ser Ser Ala Ser Asn Ala Ala
        450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
            500                 505                 510

Phe Asn Ala Ile Leu Thr Pro Tyr Met Leu Asn Val Ser Asp Trp Asn
            515                 520                 525

Trp Gly Ala Lys Thr Gly Leu Tyr Trp Gly Gly Phe Thr Ala Leu Thr
        530                 535                 540

Leu Ala Trp Val Ile Ile Asp Leu Pro Glu Thr Thr Gly Arg Thr Phe
545                 550                 555                 560

Ser Glu Ile Asn Glu Leu Phe Asn Gln Gly Val Pro Ala Arg Lys Phe
                565                 570                 575

Ala Ser Thr Val Val Asp Pro Phe Gly Lys Ser Gly Leu Lys Asn Leu
            580                 585                 590

Pro Gln Val Asp Asp Ile Ile Asp Arg Ser Ser Ser Met Ser Gln Gln
        595                 600                 605

Ala Leu
    610

<210> SEQ ID NO 8
<211> LENGTH: 616
<212> TYPE: PRT
<213> ORGANISM: Saccharomyces cerevisiae
<220> FEATURE:
<221> NAME/KEY: MISC_FEATURE
<222> LOCATION: (1)..(616)
<223> OTHER INFORMATION: AGT1 from strain S288c

<400> SEQUENCE: 8

Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
                20                  25                  30

Gln Glu Val Phe Asn Thr Glu Asp Phe Glu Glu Gly Lys Lys Asp Ser
            35                  40                  45

Ala Phe Glu Leu Asp His Leu Glu Phe Thr Thr Asn Ser Ala Gln Leu
        50                  55                  60

Gly Asp Ser Asp Glu Asp Asn Glu Asn Val Ile Asn Glu Met Asn Ala
65                  70                  75                  80
```

```
Thr Asp Asp Ala Asn Glu Ala Asn Ser Glu Glu Lys Ser Met Thr Leu
                85                  90                  95

Lys Gln Ala Leu Leu Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
            115                 120                 125

Ala Leu Tyr Ala Leu Pro Val Phe Gln Arg Lys Phe Gly Thr Leu Asn
        130                 135                 140

Gly Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Gly
            180                 185                 190

Leu Leu Thr Ala Tyr Ile Phe Ile Leu Tyr Tyr Cys Lys Ser Leu Ala
        195                 200                 205

Met Ile Ala Val Gly Gln Ile Leu Ser Ala Ile Pro Trp Gly Cys Phe
210                 215                 220

Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
        275                 280                 285

Ala Pro Leu Met Ile Gly Ile Phe Phe Ala Pro Glu Ser Pro Trp Trp
290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Val Asp Leu Thr
                325                 330                 335

Leu Lys Gln Ile Glu Leu Thr Ile Glu Lys Glu Arg Leu Leu Ala Ser
            340                 345                 350

Lys Ser Gly Ser Phe Phe Asn Cys Phe Lys Gly Val Asn Gly Arg Arg
        355                 360                 365

Thr Arg Leu Ala Cys Leu Thr Trp Val Ala Gln Asn Ser Ser Gly Ala
        370                 375                 380

Val Leu Leu Gly Tyr Ser Thr Tyr Phe Glu Arg Ala Gly Met Ala
385                 390                 395                 400

Thr Asp Lys Ala Phe Thr Phe Ser Leu Ile Gln Tyr Cys Leu Gly Leu
                405                 410                 415

Ala Gly Thr Leu Cys Ser Trp Val Ile Ser Gly Arg Val Gly Arg Trp
            420                 425                 430

Thr Ile Leu Thr Tyr Gly Leu Ala Phe Gln Met Val Cys Leu Phe Ile
        435                 440                 445

Ile Gly Gly Met Gly Phe Gly Ser Gly Ser Ala Ser Asn Gly Ala
450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
```

|       |       |       | 500   |       |       | 505   |       |       | 510   |       |
|-------|-------|-------|-------|-------|-------|-------|-------|-------|-------|-------|
Ile Asn Ala Ile Leu Thr Pro Tyr Met Leu Asn Val Ser Asp Trp Asn
            515          520          525

Trp Gly Ala Lys Thr Gly Leu Tyr Trp Gly Gly Phe Thr Ala Val Thr
530          535          540

Leu Ala Trp Val Ile Ile Asp Leu Pro Glu Thr Thr Gly Arg Thr Phe
545          550          555          560

Ser Glu Ile Asn Glu Leu Phe Asn Gln Gly Val Pro Ala Arg Lys Phe
            565          570         575

Ala Ser Thr Val Val Asp Pro Phe Gly Lys Gly Lys Thr Gln His Asp
        580          585         590

Ser Leu Ala Asp Glu Ser Ile Ser Gln Ser Ser Ile Lys Gln Arg
            595          600         605

Glu Leu Asn Ala Ala Asp Lys Cys
            610          615

<210> SEQ ID NO 9
<211> LENGTH: 1842
<212> TYPE: DNA
<213> ORGANISM: Saccharomyces eubayanus
<220> FEATURE:
<221> NAME/KEY: misc_feature
<222> LOCATION: (1)..(1842)
<223> OTHER INFORMATION: yHEB1505 MALT434

<400> SEQUENCE: 9

| | | | | | |
|---|---|---|---|---|---|
| atgaagggtc | tatcctcaat | gataaataga | aagaagtgca | acggtaactc | gagttcaata | 60 |
| gagaccgaag | gtggcttcgg | cgccgctgaa | tgcaactcga | tagagttgga | ggagcaaggc | 120 |
| aaaaaaactg | attttgatct | tgcccatctt | gagtatggtc | agggcccagc | agcattaagc | 180 |
| gagaatgatg | aagtaacgcc | aaatattctc | gacgctgcgc | aggatgctaa | ggaggccgac | 240 |
| gatagtgaaa | gagagatgcc | gctcatgaca | gctttgaaaa | cgtatcccaa | agcagcggct | 300 |
| tggtcgttgt | tggtttccac | aacgctgatc | caggaaggtt | atgacaccgc | catcctcggc | 360 |
| tctttctatg | ccctacccgt | ctttcagaag | aagtacggct | ctctaaatgc | ccgtacagga | 420 |
| gaatgggaga | tttcggtatc | ttggcagatt | gggctgtgtt | tatgctacat | ggcaggagag | 480 |
| atcgtgggtt | tacagttgac | aggtccctcg | gtggatttga | tgggtaaccg | ctacacattg | 540 |
| attatggcgt | tgatgttctt | aactgccttc | atttttattc | tgtatttctg | taaaagttta | 600 |
| gggatgatcg | ctgcgggaca | ggcattgtgc | ggtatgccat | ggggttgttt | ccaatgtctg | 660 |
| actgtgtctt | atgcctctga | aatctgtcct | atggcgctga | ggtactacct | gacgacatat | 720 |
| tcgaatctgt | gctggttgtt | tggtcagctt | tttgctgcag | gcatcatgaa | aaattcccaa | 780 |
| aacaaatacg | cagactcgga | cttaggatat | acgctacctt | tgctttaca | gtggatctgg | 840 |
| cctgttcctc | tagcaatagc | gatattcttt | gcacctgaat | ccccatggtg | gttagtcaag | 900 |
| aaaggaagac | tagagcaggc | aaagaggtcg | ctcgaaagaa | cactaagcgg | taagggagcc | 960 |
| gagaaagaat | cactggtggc | catggaactg | gataaaatca | aaatgactat | agagaaggag | 1020 |
| aagaagctgt | cagacgatga | aggctcctat | ttggattgtc | tgaggggcaa | ggttaatcgg | 1080 |
| aggagaacga | gaatagcctg | tctgtgctgg | gccggtcaaa | ctgtttgtgg | tgcgtcacta | 1140 |
| ataggttact | caacttactt | ctacgagaaa | gccggtgtta | gcacggaaac | agcattcact | 1200 |
| tttagtatca | ttcaatactg | tctcggtatt | gctgcaacat | ttttatcctg | gtgggcctca | 1260 |
| aaatattatg | gtagatatga | cctttacgct | tgtggactgg | ccttccagac | cgttatactg | 1320 |

```
ttcattatag gcggtttggg atgctccgac actcacggtg ccaaaatggg aagtggcgct    1380
cttctaatgg tggtcgcctt cttttacaac ctggggattg ctcccgttgt cttttgctta    1440
gtttctgaaa taccatcctc gaggctaaga actaaatcaa ttattctggc tcgtaacgcc    1500
tataatatgg catgtatcgt aactgctgtc ctgacattgt accaattgaa ttcagaaaaa    1560
tgggattggg gtgcaaagtc aggcttcttc tgggggggac tatgttttgc gacgttagta    1620
tgggctgtct ttgatctgcc cgaaaccgca ggtagaacct ttattgaaat aaatgaacta    1680
tttagacttg gagttccagc aagaaaattc aagtcaacaa aagtggaccc atttgccgcc    1740
gccaaagcaa tctctgatga aatcaaccat aaagatccca aggaagatat gaaagcttcc    1800
gccgaggaga gagagcaaag cacccccatct ctaatggatt ga                      1842
```

<210> SEQ ID NO 10
<211> LENGTH: 1842
<212> TYPE: DNA
<213> ORGANISM: Saccharomyces eubayanus
<220> FEATURE:
<221> NAME/KEY: misc_feature
<222> LOCATION: (1)..(1842)
<223> OTHER INFORMATION: FM1318 Malt4

<400> SEQUENCE: 10

```
atgaagggtc tatcctcaat gataaataga aagaagtgca acggtaactc gagctcaata     60
gagaccgaag gcggcttcgg cgccgctgaa tgcaactcga tagagttgga ggagcaaggc    120
aaaaaaactg attttgatct tgcccatctt gagtatggtc agggcccagc agcattaagc    180
gagaatgatg aagtaacgcc aaatattctc gacgctgcgc aggatgctaa ggaggcagac    240
gatagtgaaa gagagatgcc gctcatgaca gctttgaaaa cgtatcccaa agcagcggct    300
tggtcgttgt tggtttccac aacgctgatc caggaaggtt atgacaccgc catcctcggc    360
tctttctatg ccctacccgt cttttcagaag aagtacggct ctctaaatgc ccgtacagga    420
gaatgggaga tttcggtatc ttggcagatt gggctgtgtt tatgctacat ggcaggagag    480
atcgtgggtt tacagttgac aggtccctcg gtggatttga tgggtaaccg ctacacattg    540
attatggcgt tgatgttctt aactgctttc atttttattc tgtatttctg taaaagttta    600
gggatgatcg ctgcgggaca ggcattgtgc ggtatgccat ggggttgttt ccaatgtctg    660
actgtgtctt atgcctctga aatctgtcct atggcgctga ggtactacct gacgacatat    720
tcgaatctgt gctggttgtt tggtcagctt tttgctgcag gcatcatgaa aaattcccaa    780
aacaaatacg cagactcgga cttaggatat acgctacctt tgctttaca gtggatctgg    840 cctgttcctc tagcaatagc gatattcttt gcacctgaat ccccatggtg gttagtcaag    900
aaaggaagac tagagcaggc aaagaggtcg ctcgaaagaa cactaagcgg taagggagcc    960
gagaaagaat cactggtggc catggaactg ataaaatca aatgactat agagaaggag    1020 aagaagctgt cagacgatga aggctcctat ttggattgtc tgaggggcaa ggttaatcgg    1080
aggagaacga gaatagcctg tctgtgctgg gccggtcaaa ctgtttgtgg tgcgtcacta    1140
ataggttact caacttactt ctacgagaaa gccggtgtta gcacggaaac agcattcact    1200
tttagtatca ttcaatactg tctcggtatt gctgcaacat ttttatcctg gtgggcctca    1260
aaatattatg gtagatatga cctttacgct tgtggactgg ccttccagac cgttatactg    1320
ttcattatag gcggtttggg atgctccgac actcacggtg ccaaaatggg aagtggcgct    1380
cttctaatgg tcgttgcgtt ctcatacaac ctggggattg cccctgtcgt ttttttgctta    1440 gtctctgaaa taccatcgtc gaggctgaga actaaatcga tcattttagc tcgtaatgcg    1500
```

| | |
|---|---:|
| tacaacatag gaaatatcgt agttgctgtt ttgattttgt accaactgaa ctctgagaaa | 1560 |
| tggaactggg gtgccaagtc aggcttttc tggggaggat tctgcctggc tgttttaatt | 1620 |
| tgggctgtct ttgatctgcc cgaaaccgca ggtagaacct ttattgaaat aaatgaacta | 1680 |
| tttagacttg gagttccagc aagaaaattc aagtcaacaa aagtggaccc atttgccgcc | 1740 |
| gccaaagcaa tctctgatga aatcaaccat aaagatccca aggaagatat gaaagcttcc | 1800 |
| gccgaggaga gagagcaaag cacccctcatct ctaatggatt ga | 1842 |

<210> SEQ ID NO 11
<211> LENGTH: 1845
<212> TYPE: DNA
<213> ORGANISM: Saccharomyces eubayanus
<220> FEATURE:
<221> NAME/KEY: misc_feature
<222> LOCATION: (1)..(1845)
<223> OTHER INFORMATION: FM1318 Malt3

<400> SEQUENCE: 11

| | |
|---|---:|
| atgaagggct tatcctcact gataaacaga aaaaaaaaca agattgactc taattcaaat | 60 |
| gagatcgaga acggcatgaa cagtaccgat ctcaactcga tcgagatgca ggaacaaggc | 120 |
| aagaaatctg actttgatct ttcccatatt gagtacggtc aagattcacg agtaccaaaa | 180 |
| gatgatgatg aggaagtccc agatcttctc gatgaggcta tgcaggatgc gaaggaggca | 240 |
| gacgaaagtg aaggggggat gccacttctg caagctttga aaacgtatcc caaagctgct | 300 |
| gcttggtcgc tattagtctc cacaacgctg attcaagaag ttatgatac tgccatcctc | 360 |
| ggatctttct atgctttgcc cgttttccag aaggaatatg gttctctgaa tagcaagaca | 420 |
| ggagaatatg aaatttcagt ttcttggcag attggtttat ctttatgtat tgtggcaggt | 480 |
| gagattgttg gtttacaaat gactggtcct tttgtagatt acatgggtaa tcgttacaca | 540 |
| ttgattgtgg cgttgttctt tttagccgct tcacttttta ttctgtattt ttgcaaaagt | 600 |
| ttgggtatga ttgccgtggg acaagtactg tgtggtatgc catggggttg tttccaatgt | 660 |
| ttgacagtct catatgcttc cgaaatctgt cctttggctt taagatacta cctgacaact | 720 |
| tattcaaact tgtgctggac ttttggccaa cttttttgctg ctggtattat gaaaaattcc | 780 |
| caaaacaagt acccagactc ggatttggga tataagctac catttgcttt acagtggatt | 840 |
| tggcctcttc ccctggcaat aggatatatc tttgcacctg aatctccatg gtggttgatc | 900 |
| aagaaaggga gaatggaaca ggcgaagaaa tcacttgaaa gaacattgag tggcaaggga | 960 |
| cctgagaaag aactgctggt gagtatgaa ctagataaaa tcaaagtgac tattgaaaaa | 1020 |
| gaacaaaaaa tgtcagattc agaagggtca tactgggatt gtgtgaagga ctgtatcaac | 1080 |
| cggagaagaa caagaatagc ttgtttatgt tggattggtc aaaccacttg tggtacacaa | 1140 |
| ctgataggat attcaaccta ttttacgaa aaggctggtg ttagcactga aacagcattc | 1200 |
| acttttagta ttattcaata ctgtcttggt attgttgcaa cacttctatc ctggtgggct | 1260 |
| tcaaagtatt ttgggagatt tgacctttac gcgttcggac tggccattca gactgtttta | 1320 |
| ctgtttatta taggaggtct gggatgctct gatactcacg gtgcccaaat gggaagtggc | 1380 |
| gctcttctaa tggtggtcgc cttcttttac aacctgggga ttgctcccgt tgtcttttgc | 1440 |
| ttagtttctg aaataccatc ctcgaggcta agaactaaat caattattct ggctcgtaac | 1500 |
| gcctataata tggcatgtat cgtaactgct gtcctgacat tgtaccaatt gaattcagaa | 1560 |
| aaatgggatt ggggtgcaaa gtcaggcttc ttctgggggg gactatgttt tgcgacgtta | 1620 |

```
gtatgggctg tcattgattt acccgaaact gccggtagaa cctttatgga aatgaacgaa    1680
ctatttagac tcggtattcc agcaagaaag ttcaagacga ctaaagtgga cccatttgcg    1740
gctgtcaaag cggctaaaga aattgctcat aatgatccca aggaagatat ggaaacttcc    1800
atggtggaag aagggcgaag cacaccatct attacgaatt tatga                    1845
```

<210> SEQ ID NO 12
<211> LENGTH: 1833
<212> TYPE: DNA
<213> ORGANISM: Unknown
<220> FEATURE:
<223> OTHER INFORMATION: yHAB47 lager hybrid lgAGT1

<400> SEQUENCE: 12

```
atgaaaaata tactttcgct ggtaggaaga aaggaaaata ccccagaaga tgtgacggcg      60
aatcttgcgg acacctcaag cactacagtt atgcaagcaa aggacttggt tattgaggac    120
tttgaagaac gaaagaaaaa cgatgcattt gagttgaatc acttggagct cactactaat    180
gcaacacagt taagcgattc tgatgaagac aaagaaaatg taatcagagt ggcagaagct    240
actgatgatg cgaacgaagc taataacgaa gagaagagca tgactttaag acaagctttg    300
cgaaaatatc caaaggcagc gctatggtct attttggtat ctactacgct tgttatggaa    360
ggttatgata ctgcactttt aagtgcactt tatgcattgc cagttttttca gaggaagttt    420 gggactatga atgcggaagg ctcctacgaa atcacttcgc agtggcaaat tggcttgaac    480
atgtgtgttc tttgtggtga atgattggt ctacagataa ccacttacat ggtcgagttc    540
atgggtaatc gttatacaat gattacggcg ctttctcttt tgactgctta tatctttatc    600
ctttactatt gcaagagttt ggccatgatt gctgtaggac aaattctttc ggctatgcca    660 tgggggttgct tccagagtct ggctgttacc tatgcttctg aagtttgccc cctggcattg    720
agatattaca tgaccagtta ctccaacatt tgttggttgt ttggtcaaat ttttgcttct    780
ggaatcatga aaaattccca ggagaatttg gaaaactccg acttaggtta caagttacca    840
ttcgccttac aatggatctg gcctgcaccc ttaattattg gtatcttttt cgctcctgag    900
tcgccttggt ggttggtaag aaagaataag atcgtggaag ccaaaaagtc tttgaacaga    960
attctgagtg cactgttac cgagaaggag atacaagtgg atattacttt gaagcaaatt   1020
gaaatgacca ttgagaagga aagacttcgg gcatccaaat cggggtcatt tttcagctgt   1080
ttcaagggag ttgatggaag aagaacgagg cttgcgtgtt tgacttgggt tgctcagaac   1140
agtagtggtg cagtattact tggttattcg acgtacttct ttgaaagagc aggcatggcc   1200
actgacaagg ccttcacttt ctcgctaatt caatactgtc ttggtttggc aggcacgctt   1260
ggttcctggg taatatctgg ccgtgttggt agatggacta tactgaccta tggtctttca   1320
ttccaaatgg tttgtctatt tatcattggc ggaatgggtt ttgcatccgg aagcagtgct   1380
agtaacgctg ctggtggcct actgcttgct ttatctttct tctataacgc gggtatcgga   1440
gctgtcgttt actgtattgt tgcagaaatc ccatccgcag aattaaggac caagaccatt   1500
gtgctggccc gtatttgcta caatctaatg gccgtcttca atgctattct aacgccctat   1560
atgcttaacg tgagcgactg gaactggggt gccaaaactg gtctatattg gggtggcttt   1620
accgcactca ctctggcttg ggtcattatt gatttgcccg agacaactgg cagaaccttt   1680
agcgaaatca atgaactttt cagtcaaggt gtccctgcta gaaaatttgc atctacagta   1740
gttgatccct ttggaaagag agggctacaa atcgtccgc aagttgataa cattattgac   1800
cggttctcaa gcgcgagtca acaggcgtta tga                                1833
```

<210> SEQ ID NO 13
<211> LENGTH: 1833
<212> TYPE: DNA
<213> ORGANISM: Saccharomyces eubayanus
<220> FEATURE:
<221> NAME/KEY: misc_feature
<222> LOCATION: (1)..(1833)
<223> OTHER INFORMATION: yHRVM108 ncAGT1

<400> SEQUENCE: 13

```
atgaagaata tcatttcgct ggtaagaaga aagggaaata ctccagaaga tgagacagaa      60
aatcttgaag acacttcaag cactacagtt atgcaagcaa aggacttgga tattgaggac     120
tttgaagaac ggaagaaaaa cgatgcattt gagttaaatc acatggagct cactactaat     180
gcaacacagt taggcgattc tgatggagac aacgataatg caatcagagt ggcagaagct     240
actgatgatg cgaacgaagc taacaacgaa gagaaaagca tgactttaag acaagctttg     300
cgaaaatatc caaaggcagc gctatggtct atttggtat ctactacgct tgttatggaa      360
ggttatgata ccgcacttct aagtgcgctt tatgcattgc cagttttca gaggaagttc      420
gggactatga atgcggaagg ctcctacgaa atcacttcgc agtggcaaat tggcttgaac     480
atgtgtgttc tttgtggtga atgattggt ttacagatga ccacttacat ggtcgagttc      540
atgggcaatc gttatacaat gattatggcg ctttttcttt tgactgctta tattttatc      600
ctttactatt gcaagagttt agccatgatt gctgtaggac aaattctttc ggctatgcca     660
tggggttgct tccagagtct ggctgttacc tatgcttctg aagtttgccc cctggctttg     720
agatattaca tgaccagtta ctccaacatt tgttggttat ttggtcaaat ttttgcttct     780
ggaatcatga aaattctca ggagaatttg gagactccg acttgggtta caagttacca      840
ttcgccttac aatggatctg gcctgcaccc ttaattattg gtatcttctt cgctcctgag     900
tcgccatggt ggttagtaag aaagaataag atcgtggagg ccaaaaagtc tttgaacaga     960
attctgagtg gcactgctac cgagaaggag atacaagtgg atattacttt gaagcaaatt    1020
gaaatgacca ttgagaagga aagacttcgt gcatccgaat cggggtcatt tttcagctgt    1080
ttcaagggag ttgatggaag aagaacgaga cttgcgtgtt tgacttgggt tgctcagaac    1140
agtagtggtg cagttttact tggttattcg acctatttct ttgaaagagc aggcatggac    1200
actgacaagg ctttcacttt ctcgcttatt cagtactgtc ttggtttggc aggcactctt    1260
tgttcttggg taattctgg ccgtgttggt agatggacta tactgaccta tggtctttca    1320
ttccaaatgg tttgtctatt tatcattggc ggaatggggtt ttgcatccgg aagcagtgct    1380
agtaacgctg ctggtggcct actgcttgcg ttatcttttt tctataacgc gggtatcgga    1440
gctgtcgttt actgtattgt tgcagagatc ccatccgcgg aattaaggac caagactatt    1500
gtgctggctc gtatttgcta caatctaatg gccgtcttca atgctattct aacgccctat    1560
atgcttaacg tgagcgactg gaactgggt gccaaaactg gtctatattg gggtggcttc    1620
accgcactca ctctcgcttg ggtcattatt gatttgcccg agacaactgg cagaaccttt    1680
agcgaaatca tgaacttttt caatcaaggt gtccctgcta gaaaatttgc atctacagta    1740
gttgatcctt ttggaaagag cggggttaaag aatcttccgc aagttgatga cattattgac    1800
cggtcctcaa gcatgagtca gcaggcatta taa                                  1833
```

<210> SEQ ID NO 14
<211> LENGTH: 1851
<212> TYPE: DNA

<213> ORGANISM: Saccharomyces cerevisiae
<220> FEATURE:
<221> NAME/KEY: misc_feature
<222> LOCATION: (1)..(1851)
<223> OTHER INFORMATION: AGT1 from strain S288c

<400> SEQUENCE: 14

```
atgaaaaata tcatttcatt ggtaagcaag aagaaggctg cctcaaaaaa tgaggataaa      60
aacatttctg agtcttcaag agatattgta accaacagg aggttttcaa tactgaagat     120
tttgaagaag ggaaaaagga tagtgccttt gagctagacc acttagagtt caccaccaat    180
tcagcccagt taggagattc tgacgaagat aacgagaatg tgattaatga gatgaacgct    240
actgatgatg caaatgaagc taacagcgag gaaaaaagca tgactttgaa gcaggcgttg    300
ctaaaatatc aaaagcagc cctgtggtcc atattagtgt ctactaccct ggttatggaa    360
ggttatgata ccgcactact gagcgcactg tatgccctgc cagttttttca gagaaaattc    420
ggtactttga cggggagggg ttcttacgaa attacttccc aatggcagat tggtttaaac    480
atgtgtgtcc tttgtggtga gatgattggt ttgcaaatca cgacttatat ggttgaattt    540
atggggaatc gttatacgat gattacagca cttggtttgt taactgctta tatctttatc    600
ctctactact gtaaaagttt agctatgatt gctgtgggac aaattctctc agctatacca    660
tggggttgtt tccaaagttt ggctgttact tatgcttcgg aagtttgccc tttagcatta    720
agatattaca tgaccagtta ctccaacatt tgttggttat ttggtcaaat cttcgcctct    780
ggtattatga aaaactcaca agagaattta gggaactccg acttgggcta taaattgcca    840
tttgcttttac aatggatttg gcctgctcct ttaatgatcg gtatcttttt cgctcctgag    900
tcgccctggt ggttggtgag aaaggatagg gtcgctgagg caagaaaatc tttaagcaga    960
attttgagtg gtaaaggcgc cgagaaggac attcaagttg atcttacttt aaagcagatt   1020
gaattgacta ttgaaaaaga aagactttta gcatctaaat caggatcatt ctttaattgt   1080
ttcaagggag ttaatggaag aagaacgaga cttgcatgtt taacttgggt agctcaaaat   1140
agtagcggtg ccgttttact tggttactcg acatattttt ttgaaagagc aggtatggcc   1200
accgacaagg cgtttacttt ttctctaatt cagtactgtc ttgggttagc gggtacactt   1260
tgctcctggg taatatctgg ccgtgttggt agatggacaa tactgaccta tggtcttgca   1320
tttcaaatgg tctgcttatt tattattggt ggaatgggtt ttggttctgg aagcagcgct   1380
agtaatggtg ccggtggttt attgctggct ttatcattct tttacaatgc tggtatcggt   1440
gcagttgttt actgtatcgt tgctgaaatt ccatcagcgg agttgagaac taagactata   1500
gtgctggccc gtatttgcta caatctcatg gccgttatta cgctatatt aacgccctat   1560
atgctaaacg tgagcgattg gaactggggt gccaaaactg gtctatactg gggtggtttc   1620
acagcagtca ctttagcttg ggtcatcatc gatctgcctg agacaactgg tagaaccttc   1680
agtgaaatta tgaactttt caaccaaggg gttcctgcca gaaatttgc atctactgtg   1740
gttgatccat tcggaaaggg aaaaactcaa catgattcgc tagctgatga gagtatcagt   1800
cagtcctcaa gcataaaaca gcgagaatta aatgcagctg ataaatgtta a           1851
```

<210> SEQ ID NO 15
<211> LENGTH: 616
<212> TYPE: PRT
<213> ORGANISM: Unknown
<220> FEATURE:
<223> OTHER INFORMATION: yHAB47 lager hybrid scAGT1

<400> SEQUENCE: 15

```
Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asn Phe Glu Glu Gly Lys Lys Asp Ser
                35                  40                  45

Ala Phe Glu Leu Asp His Leu Glu Phe Thr Thr Asn Ser Ala Gln Leu
    50                  55                  60

Gly Asp Ser Asp Glu Asp Asn Glu Asn Met Ile Asn Glu Met Asn Ala
65                      70                  75                  80

Thr Asp Glu Ala Asn Glu Ala Asn Ser Glu Glu Lys Ser Met Thr Leu
                85                  90                  95

Lys Gln Ala Leu Leu Lys Tyr Pro Lys Ala Ala Leu Trp Ser Ile Leu
                100                 105                 110

Val Ser Thr Thr Leu Val Met Glu Gly Tyr Asp Thr Ala Leu Leu Asn
            115                 120                 125

Ala Leu Tyr Ala Leu Pro Val Phe Gln Arg Lys Phe Gly Thr Leu Asn
        130                 135                 140

Gly Glu Gly Ser Tyr Glu Ile Thr Ser Gln Trp Gln Ile Gly Leu Asn
145                 150                 155                 160

Met Cys Val Gln Cys Gly Glu Met Ile Gly Leu Gln Ile Thr Thr Tyr
                165                 170                 175

Met Val Glu Phe Met Gly Asn Arg Tyr Thr Met Ile Thr Ala Leu Gly
            180                 185                 190

Leu Leu Thr Ala Tyr Ile Phe Ile Leu Tyr Tyr Cys Lys Ser Leu Ala
        195                 200                 205

Met Ile Ala Val Gly Gln Val Leu Ser Ala Met Pro Trp Gly Cys Phe
    210                 215                 220

Gln Gly Leu Thr Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Asp Tyr Lys Leu Pro Phe Ala Leu Gln Trp Ile Trp Pro
    275                 280                 285

Ala Pro Leu Met Ile Gly Ile Phe Phe Ala Pro Glu Ser Pro Trp Trp
    290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Val Asp Leu Thr
                325                 330                 335

Leu Lys Gln Ile Glu Leu Thr Ile Glu Lys Glu Arg Leu Leu Ala Ser
            340                 345                 350

Lys Ser Gly Ser Phe Phe Asp Cys Phe Lys Gly Val Asn Gly Arg Arg
        355                 360                 365

Thr Arg Leu Ala Cys Leu Ala Trp Val Ala Gln Asn Thr Ser Gly Ala
    370                 375                 380

Cys Leu Leu Gly Tyr Ser Thr Tyr Phe Phe Glu Arg Ala Gly Met Ala
385                 390                 395                 400

Thr Asp Lys Ala Phe Thr Phe Ser Val Ile Gln Tyr Cys Leu Gly Leu
                405                 410                 415
```

Ala Gly Thr Leu Cys Ser Trp Val Ile Ser Gly Arg Val Gly Arg Trp
            420                 425                 430

Thr Ile Leu Thr Tyr Gly Leu Ala Phe Gln Met Val Cys Leu Phe Val
        435                 440                 445

Ile Gly Gly Met Gly Phe Gly Ser Gly Ser Gly Ala Ser Asn Gly Ala
    450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
            500                 505                 510

Ile Asn Ala Ile Leu Thr Pro Tyr Met Leu Asn Val Ser Asp Trp Asn
        515                 520                 525

Trp Gly Ala Lys Thr Gly Leu Tyr Trp Gly Gly Phe Thr Ala Val Thr
    530                 535                 540

Leu Ala Trp Val Ile Ile Asp Leu Pro Glu Thr Thr Gly Arg Thr Phe
545                 550                 555                 560

Ser Glu Ile Asn Glu Leu Phe Asn Gln Gly Val Pro Ala Arg Lys Phe
                565                 570                 575

Ala Ser Thr Val Val Asp Pro Phe Gly Lys Gly Lys Thr Gln His Asp
            580                 585                 590

Ser Leu Ala Asp Glu Ser Ile Ser Gln Ser Ser Ile Lys Gln Arg
        595                 600                 605

Glu Leu Asn Ala Ala Asp Lys Cys
    610                 615

<210> SEQ ID NO 16
<211> LENGTH: 1851
<212> TYPE: DNA
<213> ORGANISM: Unknown
<220> FEATURE:
<223> OTHER INFORMATION: yHAB47 lager hybrid scAGT1

<400> SEQUENCE: 16
atgaaaaata tcatttcatt ggtaagcaag aagaaggctg cctcaaaaaa tgaggataaa      60
aacatttctg agtcttcaag agatattgta aaccaacagg aggttttcaa tactgaaaat    120
tttgaagaag ggaaaaagga tagtgccttt gagctagacc acttagagtt caccaccaat    180
tcagcccagt taggagattc tgacgaagat aacgagaata tgattaatga gatgaacgct    240
actgatgaag caaatgaagc taacagcgag gaaaaaagca tgactttaaa gcaggcgttg    300
ctaaaatatc caaaagcagc cctgtggtcc atattagtgt ctactaccct ggttatggaa    360
ggttatgata ccgcactact gaacgcactg tatgccctgc cagtgtttca gaaaaattc    420 ggtactttga cggggaggg ttcttacgaa attacttccc aatggcagat tggtttaaac    480
atgtgtgtcc aatgtggtga gatgattggt ttgcaaatca cgactatat ggttgaattt    540 atggggaatc gttatacgat gattacagca cttggtttgt taactgctta tatctttatc    600
ctctactact gtaaaagttt agctatgatt gctgtgggac aagttctctc agctatgcca    660
tggggttgtt tccagggttt gactgttact tatgcttcgg aagtttgccc tttagcatta    720
agatattaca tgaccagtta ctccaacatt tgttggttat ttggtcaaat cttcgcctct    780
ggtattatga aaaactcaca agagaattta gggaactctg acttggacta taaattgcca    840
tttgctttac aatggatttg gcctgctcct ttaatgatcg gtatctttt cgctcctgag    900

```
tcgccctggt ggttggtgag aaaggatagg gtcgctgagg caagaaaatc tttaagcaga    960
attttgagtg gtaaaggcgc cgagaaggac attcaagttg atcttacttt aaagcagatt   1020
gaattgacta ttgaaaaaga aagactttta gcatctaaat caggatcatt ctttgattgt   1080
ttcaagggag ttaatggaag aagaacgaga cttgcatgtt tagcttgggt agctcaaaat   1140
actagcggtg cctgtttact tggttactcg acatatttt ttgaaagagc aggtatggcc    1200
accgacaagg cgtttacttt ttctgtaatt cagtactgtc ttgggttagc gggtacactt   1260
tgctcctggg taatatctgg ccgtgttggt agatggacaa tactgaccta tggtcttgca   1320
tttcaaatgg tctgcttatt tgttattggt ggaatgggtt ttggttctgg aagcggcgct   1380
agtaatggtg ccggtggttt attgctggct ttatcattct tttacaatgc tggtatcggt   1440
gcagttgttt actgtatcgt agctgaaatt ccatcagcgg agttgagaac taagactata   1500
gtgctggccc gtatttgcta caatctcatg gccgttatca acgctatatt aacgccctat   1560
atgctaaacg tgagcgattg gaactggggt gccaaaactg gtctatactg gggtggtttc   1620
acagcagtca ctttagcttg ggtcatcatc gatctgcctg agacaactgg tagaaccttc   1680
agtgaaatta atgaactttt caaccaaggg gttcctgcca gaaatttgc atctactgtg    1740 gttgatccat tcggaaaggg aaaaaactcaa catgattcgc tagctgatga gagtatcagt   1800
cagtcctcaa gcataaaaca gcgagaatta aatgcagctg ataaatgtta a             1851

<210> SEQ ID NO 17
<211> LENGTH: 60
<212> TYPE: DNA
<213> ORGANISM: Artificial Sequence
<220> FEATURE:
<223> OTHER INFORMATION: oHECPB75 primer

<400> SEQUENCE: 17
tatagacacg caaacacaaa tacacacact aaattaatga agggattatc ctcattaata    60

<210> SEQ ID NO 18
<211> LENGTH: 60
<212> TYPE: DNA
<213> ORGANISM: Artificial Sequence
<220> FEATURE:
<223> OTHER INFORMATION: oHECPB76 primer

<400> SEQUENCE: 18
tcaagaaatt cgcttattta gaagtggcgc gaattcacta tcatttgttc acaacagatg    60

<210> SEQ ID NO 19
<211> LENGTH: 60
<212> TYPE: DNA
<213> ORGANISM: Artificial Sequence
<220> FEATURE:
<223> OTHER INFORMATION: oHECPB77 primer

<400> SEQUENCE: 19
cacgcaaaca caaatacaca cactaaatta atgaaaaata tactttcgct ggtaggaaga    60

<210> SEQ ID NO 20
<211> LENGTH: 60
<212> TYPE: DNA
<213> ORGANISM: Artificial Sequence
<220> FEATURE:
<223> OTHER INFORMATION: oHECPB78 primer

<400> SEQUENCE: 20
caagaaattc gcttatttag aagtggcgcg aattcactat cataacgcct gttgactcgc    60
```

<210> SEQ ID NO 21
<211> LENGTH: 60
<212> TYPE: DNA
<213> ORGANISM: Artificial Sequence
<220> FEATURE:
<223> OTHER INFORMATION: oHECPB104 primer

<400> SEQUENCE: 21
acacgcaaac acaaatacac acactaaatt aatgaagaat atcatttcgc tggtaagaag    60

<210> SEQ ID NO 22
<211> LENGTH: 60
<212> TYPE: DNA
<213> ORGANISM: Artificial Sequence
<220> FEATURE:
<223> OTHER INFORMATION: oHECPB105 primer

<400> SEQUENCE: 22
gaaattcgct tatttagaag tggcgcgaat tcactattat aatgcctgct gactcatgct    60

<210> SEQ ID NO 23
<211> LENGTH: 20
<212> TYPE: DNA
<213> ORGANISM: Artificial Sequence
<220> FEATURE:
<223> OTHER INFORMATION: oHECPB124 primer

<400> SEQUENCE: 23
cctatgcttc tgaagtttgc                                                20

<210> SEQ ID NO 24
<211> LENGTH: 18
<212> TYPE: DNA
<213> ORGANISM: Artificial Sequence
<220> FEATURE:
<223> OTHER INFORMATION: oHECPB125 primer

<400> SEQUENCE: 24
cctgccaaac caagacag                                                  18

<210> SEQ ID NO 25
<211> LENGTH: 22
<212> TYPE: DNA
<213> ORGANISM: Artificial Sequence
<220> FEATURE:
<223> OTHER INFORMATION: oHECPB128 primer

<400> SEQUENCE: 25
gcttgtttat gttgggtcgg tc                                             22

<210> SEQ ID NO 26
<211> LENGTH: 22
<212> TYPE: DNA
<213> ORGANISM: Artificial Sequence
<220> FEATURE:
<223> OTHER INFORMATION: oHECPB129 primer

<400> SEQUENCE: 26
gaccgaccca acataaacaa gc                                             22

<210> SEQ ID NO 27
<211> LENGTH: 60
<212> TYPE: DNA
<213> ORGANISM: Artificial Sequence
<220> FEATURE:

```
<223> OTHER INFORMATION: oHECPB138 primer

<400> SEQUENCE: 27
acacgcaaac acaaatacac acactaaatt aatgaagggt ctatcctcaa tgataaatag      60

<210> SEQ ID NO 28
<211> LENGTH: 60
<212> TYPE: DNA
<213> ORGANISM: Artificial Sequence
<220> FEATURE:
<223> OTHER INFORMATION: oHECPB139 primer

<400> SEQUENCE: 28
cgcttattta gaagtggcgc gaattcacta tcaatccatt agagatgggg tgctttgctc      60

<210> SEQ ID NO 29
<211> LENGTH: 60
<212> TYPE: DNA
<213> ORGANISM: Artificial Sequence
<220> FEATURE:
<223> OTHER INFORMATION: oHECPB140 primer

<400> SEQUENCE: 29
cacgcaaaca caaatacaca cactaaatta atgaagggtc tatcttcaat attgaataga     60

<210> SEQ ID NO 30
<211> LENGTH: 60
<212> TYPE: DNA
<213> ORGANISM: Artificial Sequence
<220> FEATURE:
<223> OTHER INFORMATION: oHECPB141 primer

<400> SEQUENCE: 30
cgcttattta gaagtggcgc gaattcacta tcaaatcgta agagatgggg tagttaattc     60

<210> SEQ ID NO 31
<211> LENGTH: 60
<212> TYPE: DNA
<213> ORGANISM: Artificial Sequence
<220> FEATURE:
<223> OTHER INFORMATION: oHECPB142 primer

<400> SEQUENCE: 31
cacgcaaaca caaatacaca cactaaatta atgaagggct tatcctcact gataaacaga     60

<210> SEQ ID NO 32
<211> LENGTH: 60
<212> TYPE: DNA
<213> ORGANISM: Artificial Sequence
<220> FEATURE:
<223> OTHER INFORMATION: oHECPB143 primer

<400> SEQUENCE: 32
cgcttattta gaagtggcgc gaattcacta tcataaattc gtaatagatg gtgtgcttcg     60

<210> SEQ ID NO 33
<211> LENGTH: 26
<212> TYPE: DNA
<213> ORGANISM: Artificial Sequence
<220> FEATURE:
<223> OTHER INFORMATION: oHECPB156 primer

<400> SEQUENCE: 33
atattatggt agatatgacc tttacg                                          26
```

```
<210> SEQ ID NO 34
<211> LENGTH: 27
<212> TYPE: DNA
<213> ORGANISM: Artificial Sequence
<220> FEATURE:
<223> OTHER INFORMATION: oHECPB157 primer

<400> SEQUENCE: 34
ggttgatttc atcagagatt gctttgg                                              27

<210> SEQ ID NO 35
<211> LENGTH: 26
<212> TYPE: DNA
<213> ORGANISM: Artificial Sequence
<220> FEATURE:
<223> OTHER INFORMATION: oHECPB158 primer

<400> SEQUENCE: 35
cgtaaaggtc atatctacca taatat                                               26

<210> SEQ ID NO 36
<211> LENGTH: 27
<212> TYPE: DNA
<213> ORGANISM: Artificial Sequence
<220> FEATURE:
<223> OTHER INFORMATION: oHECPB159 primer

<400> SEQUENCE: 36
ccaatgtctg actgtgtctt atgcctc                                              27

<210> SEQ ID NO 37
<211> LENGTH: 27
<212> TYPE: DNA
<213> ORGANISM: Artificial Sequence
<220> FEATURE:
<223> OTHER INFORMATION: oHECPB160 primer

<400> SEQUENCE: 37
gaggcataag acacagtcag acattgg                                              27

<210> SEQ ID NO 38
<211> LENGTH: 18
<212> TYPE: DNA
<213> ORGANISM: Artificial Sequence
<220> FEATURE:
<223> OTHER INFORMATION: oHECPB161 primer

<400> SEQUENCE: 38
ctgtcttggt ttggcagg                                                        18

<210> SEQ ID NO 39
<211> LENGTH: 26
<212> TYPE: DNA
<213> ORGANISM: Artificial Sequence
<220> FEATURE:
<223> OTHER INFORMATION: oHECPB162 primer

<400> SEQUENCE: 39
ctgtgaaagt ttagggatga ttgcgg                                               26

<210> SEQ ID NO 40
<211> LENGTH: 26
<212> TYPE: DNA
<213> ORGANISM: Artificial Sequence
<220> FEATURE:
<223> OTHER INFORMATION: oHECPB163 primer
```

<400> SEQUENCE: 40
ccgcaatcat ccctaaactt tcacag                                    26

<210> SEQ ID NO 41
<211> LENGTH: 25
<212> TYPE: DNA
<213> ORGANISM: Artificial Sequence
<220> FEATURE:
<223> OTHER INFORMATION: oHECPB164 primer

<400> SEQUENCE: 41
cctgtatatg ttggatcggt caaac                                     25

<210> SEQ ID NO 42
<211> LENGTH: 25
<212> TYPE: DNA
<213> ORGANISM: Artificial Sequence
<220> FEATURE:
<223> OTHER INFORMATION: oHECPB165 primer

<400> SEQUENCE: 42
gtttgaccga tccaacatat acagg                                     25

<210> SEQ ID NO 43
<211> LENGTH: 22
<212> TYPE: DNA
<213> ORGANISM: Artificial Sequence
<220> FEATURE:
<223> OTHER INFORMATION: oHECPB166 primer

<400> SEQUENCE: 43
cctttggctt taagatacta cc                                        22

<210> SEQ ID NO 44
<211> LENGTH: 22
<212> TYPE: DNA
<213> ORGANISM: Artificial Sequence
<220> FEATURE:
<223> OTHER INFORMATION: oHECPB167 primer

<400> SEQUENCE: 44
ggtagtatct taaagccaaa gg                                        22

<210> SEQ ID NO 45
<211> LENGTH: 20
<212> TYPE: DNA
<213> ORGANISM: Artificial Sequence
<220> FEATURE:
<223> OTHER INFORMATION: oHECPB168 primer

<400> SEQUENCE: 45
ggatgctctg atactcacgg                                           20

<210> SEQ ID NO 46
<211> LENGTH: 20
<212> TYPE: DNA
<213> ORGANISM: Artificial Sequence
<220> FEATURE:
<223> OTHER INFORMATION: oHECPB169 primer

<400> SEQUENCE: 46
ccgtgagtat cagagcatcc                                           20

<210> SEQ ID NO 47
<211> LENGTH: 58

```
<212> TYPE: DNA
<213> ORGANISM: Artificial Sequence
<220> FEATURE:
<223> OTHER INFORMATION: oHECPB170 primer

<400> SEQUENCE: 47
ggaragtgat accttatcat ctgctgcgct aagagtcaag atctgtttag cttgcctt      58

<210> SEQ ID NO 48
<211> LENGTH: 56
<212> TYPE: DNA
<213> ORGANISM: Artificial Sequence
<220> FEATURE:
<223> OTHER INFORMATION: oHECPB171 primer

<400> SEQUENCE: 48
actcaaaaaa aattccaaaa gctattaggt aactgagctc gttttcgaca ctggat        56

<210> SEQ ID NO 49
<211> LENGTH: 23
<212> TYPE: DNA
<213> ORGANISM: Artificial Sequence
<220> FEATURE:
<223> OTHER INFORMATION: oHECPB172 primer

<400> SEQUENCE: 49
cgatatttcc gccgcagccc gag                                            23

<210> SEQ ID NO 50
<211> LENGTH: 24
<212> TYPE: DNA
<213> ORGANISM: Artificial Sequence
<220> FEATURE:
<223> OTHER INFORMATION: oHECPB173 primer

<400> SEQUENCE: 50
cttagtagca gcgacatatt caag                                           24

<210> SEQ ID NO 51
<211> LENGTH: 27
<212> TYPE: DNA
<213> ORGANISM: Artificial Sequence
<220> FEATURE:
<223> OTHER INFORMATION: oHCT770 primer

<400> SEQUENCE: 51
aactcttgtt ttcttctttt ctctaaa                                        27

<210> SEQ ID NO 52
<211> LENGTH: 22
<212> TYPE: DNA
<213> ORGANISM: Artificial Sequence
<220> FEATURE:
<223> OTHER INFORMATION: oHCT771 primer

<400> SEQUENCE: 52
gggacctaga cttcaggttg tc                                             22
```